(12) United States Patent
Katz

(10) Patent No.: US 10,918,670 B2
(45) Date of Patent: *Feb. 16, 2021

(54) OSTEOINDUCTIVE PUTTIES AND METHODS OF MAKING AND USING SUCH PUTTIES

(71) Applicant: RTI Surgical, Inc., Alachua, FL (US)

(72) Inventor: Jordan Katz, Short Hills, NJ (US)

(73) Assignee: RTI Surgical, Inc., Alachua, FL (US)

( * ) Notice: Subject to any disclaimer, the term of this patent is extended or adjusted under 35 U.S.C. 154(b) by 229 days.

This patent is subject to a terminal disclaimer.

(21) Appl. No.: 15/617,234

(22) Filed: Jun. 8, 2017

(65) Prior Publication Data

US 2017/0274020 A1 Sep. 28, 2017

Related U.S. Application Data

(63) Continuation of application No. 12/341,917, filed on Dec. 22, 2008, now Pat. No. 9,700,584.

(60) Provisional application No. 61/008,887, filed on Dec. 21, 2007.

(51) Int. Cl.
*A61K 35/32* (2015.01)
*A61L 27/24* (2006.01)

(52) U.S. Cl.
CPC .............. *A61K 35/32* (2013.01); *A61L 27/24* (2013.01); *A61L 2430/02* (2013.01)

(58) Field of Classification Search
CPC ...... A61L 27/24; A61L 2430/02; A61P 19/00; A61K 35/32
See application file for complete search history.

(56) References Cited

U.S. PATENT DOCUMENTS

| | | | |
|---|---|---|---|
| 4,002,739 A | 1/1977 | Turner et al. | |
| 4,627,982 A | 12/1986 | Seyedin et al. | |
| 4,971,954 A | 11/1990 | Brodsky et al. | |
| 5,236,456 A | 8/1993 | O'Leary et al. | |
| 5,244,577 A | 9/1993 | Notoya et al. | |
| 5,304,169 A | 4/1994 | Sand | |
| 5,371,191 A | 12/1994 | Poser et al. | |
| 5,405,390 A | 4/1995 | O'Leary et al. | |
| 5,413,791 A | 5/1995 | Rhee et al. | |
| 5,531,791 A | 7/1996 | Wolfinbarger | |
| 5,563,124 A | 10/1996 | Damien et al. | |
| 6,123,731 A | 9/2000 | Boyce et al. | |
| 6,180,605 B1 | 1/2001 | Chen et al. | |
| 6,576,249 B1 | 6/2003 | Gendler et al. | |
| 6,679,918 B1 | 1/2004 | Benedict et al. | |
| 7,132,110 B2 | 11/2006 | Kay et al. | |
| 7,241,813 B2 | 7/2007 | Kay et al. | |
| 8,652,503 B2 * | 2/2014 | Wironen | A61F 2/28 424/423 |
| 9,700,584 B2 * | 7/2017 | Katz | A61K 35/32 |
| 2002/0076429 A1 * | 6/2002 | Wironen | A61F 2/28 424/426 |
| 2003/0206937 A1 | 11/2003 | Gertzman et al. | |
| 2005/0084542 A1 | 4/2005 | Rosenberg et al. | |
| 2005/0118230 A1 | 6/2005 | Hill et al. | |
| 2006/0013857 A1 | 1/2006 | Kronenthal | |
| 2006/0039951 A1 | 2/2006 | Sapieszko et al. | |
| 2006/0083769 A1 | 4/2006 | Kumar et al. | |
| 2006/0280803 A1 | 12/2006 | Kumar et al. | |
| 2007/0178158 A1 | 8/2007 | Knaack et al. | |
| 2007/0202148 A1 | 8/2007 | Ringeisen et al. | |
| 2007/0202191 A1 | 8/2007 | Borden | |
| 2007/0231366 A1 | 10/2007 | Sawhney et al. | |
| 2008/0160085 A1 | 7/2008 | Boland et al. | |

FOREIGN PATENT DOCUMENTS

| | | |
|---|---|---|
| EP | 0171176 A2 | 2/1986 |
| EP | 2222348 B1 | 9/2009 |
| WO | 98/35653 A1 | 8/1998 |
| WO | 2009086305 A2 | 7/2009 |

OTHER PUBLICATIONS

Gomez-Guillen et al. (Functional and bioactive properties of collagen and gelatin from alternative sources: A review Food Hydrocolloids 25 (2011) 1813-1827). (Year: 2011).*
Djabourov et al., Structure and rheology of gelatin and collagen gels, Biorheology, 1993; 30(3-4): 191-205.
Mu et al., Temperature induced denaturation of collagen in acidic solutions, Biopolymers, 2007; 86(4): 282-287.
Berry et al., Degradation of bovine corneal collagen by alkali, Cornea, 1989; 8(2): 150-154.
Courts, Structural changes in collagen. The action of alkalis and acids in the conversion of collagen to eucollagen, Biochemical Journal, 1960; 74(2): 238-247.
Wang et al., Effects of collagen unwinding and cleavage on the mechanical Integrity of the collagen network in bone, Calcified Tissue International, 2002; 71(2); 186-192.
Weir, Effect of temperature on the volume of leather and collagen in water, US Department of Commerce. National Bureau of Standards, Research Paper RP1924. 1948; 41:279-285.
ASTM International, Standard guide for characterization of type1 collagen as starting material for surgical implants and substrates for tissue-engineered medical products (TEMPs). (Reapproved 2007) Designation: F2212-02 p. 1-9.

(Continued)

*Primary Examiner* — Kortney L. Klinkel
*Assistant Examiner* — William Y Lee
(74) *Attorney, Agent, or Firm* — McAndrews, Held & Malloy, Ltd.

(57) ABSTRACT

The present disclosure relates to osteoinductive putties and other implantable compositions for repair of bone defects and other medical uses. Specifically, the technology pertains to carriers for use in implantable compositions, such as osteoinductive putties. The osteoinductive putties are made entirely from donor tissue such as demineralized bone matrix, and the putties have excellent physical properties. The present disclosure relates to osteoinductive putties, carriers, compositions, implants, kits, methods of making and methods of using any of the foregoing.

9 Claims, 24 Drawing Sheets

(56) References Cited

OTHER PUBLICATIONS

Bank et al., Amino acid analysis by reverse-phase high-performance liquid chromatography: improved derivatization and detection conditions with 9-fluorenylmethyl chloroformate, Analytical Biochemistry, 1996; 240(2): 167-176.
Han et al., Effects of moisture and temperature on the osteoinductivity of demineralized bone matrix, Journal of Orthopaedic Research, 2005; 23(4):855-861.
Wright et al., Denaturation of Collagen via heating: an irreversible rate process, Annual Review of Biomedical Engineering, 2002, 4: 109-128.
Persikov et al., unstable molecules form stable tissues, Proceedings of National Academy of Science, 2002; 99(3): 1101-1103.
Puustjarvi et al., Do more highly organized collagen fibrils increase bone mechanical strength in loss of mineral density after one-year running training?, Journal of Bone and Mineral Research, 1999; 14(3): 321-329.
Lange et al., Improved determination of small amounts of free hydroxyproline in biological fluids, Clinical Chemistry, 1994; 40(9): 1735-1738.
Sundar-Raj et al., Structure and Biosynthesis of Rabbit Lens Capsule Collagen, Investigate Ophthalmology and Visual Science, 1982; 230: 743-756.
Ma et al., Experimental study on relationship between retinal vein occlusion and loss of vitreous gel mass, Molecular Vision, 2005; 11: 744-748.
Davis et al., Hysreresis in the triple helix-coil transition of type III collagen, Journal of Biological Chemistry, 1993; 268 (34): 25965-25972.
Bonadio J et al., Altered triple helical structure of type I procollagen in lethal perinatal osteogenesis imperfecta, Journal of Biological Chemistry, 1985; 260(3): 1734-1742.
Leikina et al., Type I collagen is thermally unstable at body temperature, Proceedings of the National Academy of Science. 2002; 99(3): 1314-1318.
Kotch et al., Self-assembly of synthetic collagen triple helices, Proceedings of the National Academy of Science, 2006; 103(9) 3028-3033.
Syftestad et al., Degradation of bone matrix morphogenic activity by pulverization, Clinical Orthopaedics and Related Resarch, 1979; 141: 281-285.
Rigby, Temperature relationships of poikilotherms and the melting temperature of molecular collagen, 1968; 135: 223-229.
Giruand-Guille, Liquid crystalline phases of sonicated type I collagen, Biology of the Cell, 1989; 67: 97-101.
Lee et al., Biolmedical applications of collagen, International Journal of Pharmaceutics, 2001;221: 1-22.
Parsons et al., Ascorbic acid-independent synthesis of collagen in mice, American Journal of Physiology, Endocrinology and Metabolism, 2006; 290(6); E1131-1139.
ASTM International, Standard specification for anorganic bone for surgical implants, Designation: F1581-99 p. 1-4.
Cole, Gelatin. Encyclopedia of Food Science and Technology, 2nd edition, 4 vols. Frederick J Francis, editor, New York: John Wiley & Sons, 2000. 1183-1188.
Urist et al., Bone morphogenesis in implants of insoluble bone gelatin, Proceedings of the National Academy of Science, 1973; 70(12): 3511-3515.
Mazzi et al., New marker of bone resorption: hydroxproline-containing peptide high-performance liquid chomatographic assay without hydrolysis as an alternative to hydroxproline determination: a preliminary report, Journal of Chromatography B: Biomedical Applications, 1996; 678(2); 165-172.
Miksik et al., Capillary electromigration methods of the study of collagen, Journal of Chromatography B, 2006; 841 (1-2): 3-13.
Lin et al., Comparison of physical-chemical properties of type I collagen different species, Food Chemistry, 2006, 99 (2): 244-251.
Pacaccio et al., Demineralized bone matrix: basic science and clinical application, Clinics in Podiatric Medicine and Surgery, 2005; 22(4): 599-606.
Friess, Collagen: biomaterial for drug delivery, European Journal of Pharmaceutics and Biopharmaceutics, 1998; 45: 113-136.
Brauer et al., Effect of dietary protein on muscle collagen, collagenase and shear force of farmed white shrimp (Litopenaeus vannamei), European Food research and Technology, 2003; 217(4): 277-280.
Miller at al., Determination of fibrosis from cryostat sections using high performance liquid chromatography: sketal muscle, The Histochemical Journal, 1999; 31(2): 89-94.
Yaegaki et al., Improved high-performance liquid chromatography method for quanitation of proline and hydroxyproline in biological materials, Journal of Chromatography, 1986; 356(1): 163-70.
International Search Report and Written Opinion corresponding to International Patent Application Serial No. PCT/US2008/88021, dated Apr. 16, 2009.
International Preliminary Report on Patentability corresponding to International Patent Application No. PCT/US2008/088021, dated Jul. 1, 2010.
European Patent Office, Communication with extended European search report, in European application No. 08868319 dated Oct. 21, 2011.
Canadian Intellectual Proerty Office, Office Action in Canadian Application No. 2,710,207 dated Nov. 21, 2013. (3 pages).
"Collagen, Type I solution from rat tail," Sigma-Aldrich, 2015, 3 pages.
"Collagen Solution, Type I from rat tail," Product Information, Sigma Aldrich, 2 pages.
Sujithra et al., "Isolation and Determination of Type I Collagen From Tilapia (*Oreochromis niloticus*) Waste," International Journal of Engineering and Technology (IJET), Jun.-Jul. 2013, vol. 5, No. 3, pp. 2181-2185.
Coulson et al., "Collagen and a Thermally Reversible Poloxamer Deliver Demineralized Bone Matrix (DBM) and Biologically Active Proteins to Sites of Bone Regeneration," Portland Bone Symposium, 1999, 8 pages.
Canadian Intellectual Property Office, Canadian Office Action dated Feb. 17, 2016 for Canadian Patent Application No. 2,710,207.
Government of Canada, Innovation, Science and Economic Development Canada, Canadian Company Capabilities, Citagenix Inc., DynaGraft II product description (5 pages).

\* cited by examiner

OSTEOINDUCTIVE PUTTIES AND METHODS OF MAKING AND USING SUCH PUTTIES

CROSS REFERENCE TO RELATED APPLICATIONS

This application is a continuation of U.S. patent application Ser. No. 12/341,917 (now allowed), which was filed Dec. 22, 2008. U.S. patent application Ser. No. 12/341,917 relates to and claims priority benefits from U.S. Provisional Patent Application Ser. No. 61/008,887, filed Dec. 21, 2007, entitled "Osteoinductive Putties and Methods of Making and Using Such Putties". These applications are hereby incorporated by reference in their entirety.

FIELD OF THE INVENTION

The technical field involves putties and other implantable compositions for repair of bone defects and other medical uses. Specifically, the technology pertains to an osteoinductive putty made entirely from donor tissue such as demineralized bone matrix and having desirable physical properties. The present disclosure relates to osteoinductive putties, carriers, compositions, implants, kits, methods of making and methods of using any of the foregoing.

BACKGROUND OF THE INVENTION

Various compositions have been used to repair bone defects and other damaged tissues. For example, compositions are available to promote or support new bone growth and/or to provide active agents that induce new bone growth. Demineralized bone matrix (DBM) and bone morphogenetic proteins (BMPs) are two agents that have been used to induce bone growth.

DBM is bone that has been demineralized at least partially. Bone can be demineralized in a variety of ways, such as by exposure to an acid, to remove at least some of its natural mineral content. DBM typically includes highly cross-linked collagen as well as other proteins, such as BMPs and other growth factors. DBM alone, or with one or more added BMPs, or other growth factors or with some combination thereof can be used to treat bone defects.

DBM and BMPs can be used in combination with carriers in order to create an implantable material. A number of different carriers have been used in the past with varying degrees of success. Previously used carriers include materials such as collagen sponges, glycerol, synthetic polymers and hydrogels (e.g., gelatin and chitosan).

As an example, GRAFTON® is a commercially available product comprising DBM suspended in a polyhydroxy compound (e.g. glycerol) or esters thereof, optionally including various other ingredients, such as gelatin.

BRIEF SUMMARY OF THE INVENTION

The present invention provides novel carriers for use in implantable compositions, such as in osteoinductive putties. The present carriers have excellent physical properties, such as excellent stability, cohesiveness, flowability, moldability, extrudability, resistance to irrigation, and/or cohesion in solution. In various embodiments, the carriers include a mixture of collagen fragments. In some embodiments, the carriers comprise a mixture of collagen fragments having a substantially uniform molecular weight distribution within the range of from about 45 kDa (kilodaltons) to about 66 kDa, and/or from about 29 kDa to about 97 kDa. Alternatively or additionally, the carriers comprise a mixture of collagen fragments having a sodium dodecyl sulfate polyacrylamide gel electrophoresis (SDS-PAGE) profile that does not include a banded region between about 45 kDa and about 66 kDa, and/or between about 29 kDa and about 97 kDa. Alternatively or additionally, the carriers comprise a mixture of collagen fragments having an SDS-PAGE profile substantially the same as shown in Lane C of any of FIGS. 2A through 2D. Alternatively or additionally, the carriers comprise a mixture of collagen fragments having an SDS-PAGE profile having a discrete band between about 15 kDa and about 20 kDa.

The present carriers have superior physical properties compared to other materials employed as carriers. Many of these properties are due to the fact that the carriers are not hydrogels or do not form a hydrogel even after the passage of time. In some embodiments, the carriers and putties do not have a measurable Bloom strength (are not a gelatin) and/or are provided as a viscous liquid.

The present invention also provides novel osteoinductive putties. The osteoinductive putties include a carrier, such as the carriers described above, and an osteoinductive substance, such as demineralized bone matrix or one or more bone morphogenetic proteins. The present invention provides osteoinductive putties comprising an osteoinductive substance, and a carrier comprising a mixture of collagen fragments, wherein the putty is extrudable, moldable, resistant to irrigation, and maintains cohesion in solution. The putty can be adapted for packing into a bone defect, such as a spinal or vertebral defect. Various embodiments of the osteoinductive putties can remain extrudable, moldable, resistant to irrigation and/or resistant to dissolution (cohesive in solution), and retain their osteoinductive properties, even following extrusion, forming, molding or shaping, and after terminal sterilization and extended storage (for example, sterilization by gamma irradiation followed by storage overnight or longer, or for at least one, two or three months, or up to six months or one year) in a sealed package. In some embodiments, the osteoinductive substance is demineralized bone matrix, and the demineralized bone matrix and the carrier are derived from the same donor and/or a single collagen source (such as an initial DBM sample), and/or the demineralized bone matrix and the carrier are both derived from cortical bone, cancellous bone, trabecular bone, or combinations thereof.

The present invention also provides novel methods of making a carrier for use in an implantable composition. The methods include the steps of providing a collagen source comprising collagen, such as fibrillar collagen, and combining the collagen source with a denaturing solution to create a collagen source mixture. For example, fibrillar collagen includes Type I collagen and Type II collagen. The collagen source mixture is heated to a temperature and for a time sufficient to produce a carrier having the desired molecular weight distribution and/or the desired physical properties as described herein. For example, the collagen source mixture can be heated at about 120° C. for about 90 minutes. The methods can also include drying and/or freezing the collagen source mixture (such as by lyophilization), so that a carrier is provided in dry form. The methods can also include the step of neutralizing (which encompasses partially neutralizing or fully neutralizing) the collagen source mixture after heating by adding a base or an acid.

The present invention also provides novel methods of making an osteoinductive putty. The methods include the steps of providing an osteoinductive substance, a liquid medium, and a collagen source, such as a collagen source comprising preferably Type I or Type II collagen. The methods also include combining the collagen source with a denaturing solution to create a collagen source mixture. The collagen source mixture is heated at a temperature and for a time sufficient to produce the desired carrier. The carrier is combined with the osteoinductive substance and the liquid medium in relative amounts sufficient to form a putty. After heating, the denatured collagen source mixture can be frozen and/or dried (such as by lyophilization) to form a dry carrier.

The present invention also provides novel kits comprising an osteoinductive putty in a package. The kits include an osteoinductive putty comprising an osteoinductive substance, a carrier comprising a mixture of collagen fragments, and a liquid medium. The kits also include a package, such as a syringe. In such kits, the osteoinductive substance and carrier are preferably sterilized after being sealed in the package, and the putty is ready to use (RTU) upon removal from the package. In various embodiments, the putty is stable in the sealed package for at least about one week, or at least about one month, or at least about six months, or at least about twelve months, or at least about 2 years, or at least about 3 years, or another length of time. Even after extended storage (for example, overnight or longer, or for at least one, two or three months, or up to six months or at least one, two or three years) in a package that is moisture resistant (e.g., hermetically sealed), preferred embodiments of the osteoinductive paste remain extrudable, moldable, resistant to irrigation and cohesive in solution, and/or capable of packing into a bone defect site, while retaining their osteoinductive properties.

The present invention also provides novel methods of treating a subject in need of treatment for a bone defect. The methods include implanting an osteoinductive putty into a bone defect, wherein the putty comprises an osteoinductive substance, a liquid medium, and a carrier as described herein. In some embodiments, the osteoinductive putty is directly injected from a syringe into the subject. The methods of treatment can also include the step of irrigating the bone defect after implanting the osteoinductive putty without washing away a substantial amount of the osteoinductive putty.

The present invention also provides novel implantable compositions suitable for use in making formed implants. The present implantable compositions have desirable physical properties, such as excellent handling and cohesion in solution. In various embodiments, the implantable compositions include a mixture of collagen fragments. The implantable compositions are produced by combining a collagen source with a denaturing solution to create a collagen source mixture. The collagen source mixture is heated to a temperature and for a time sufficient to produce an implantable composition suitable for making a formed implant. For example, the collagen source mixture can be heated at about 120° C. for about 60 minutes or at about 100° C. for about 90 minutes or longer.

The present invention also provides novel formed implants. The formed implants include an implantable composition, such as the implantable composition described above, and an osteoinductive substance. The formed implants are made by combining an osteoinductive substance, a liquid medium, and the implantable composition described above in relative amounts sufficient to form a formed implant.

These and other features of the present invention are discussed or apparent in the following detailed description.

DETAILED DESCRIPTION OF THE INVENTION

Figure 1A:
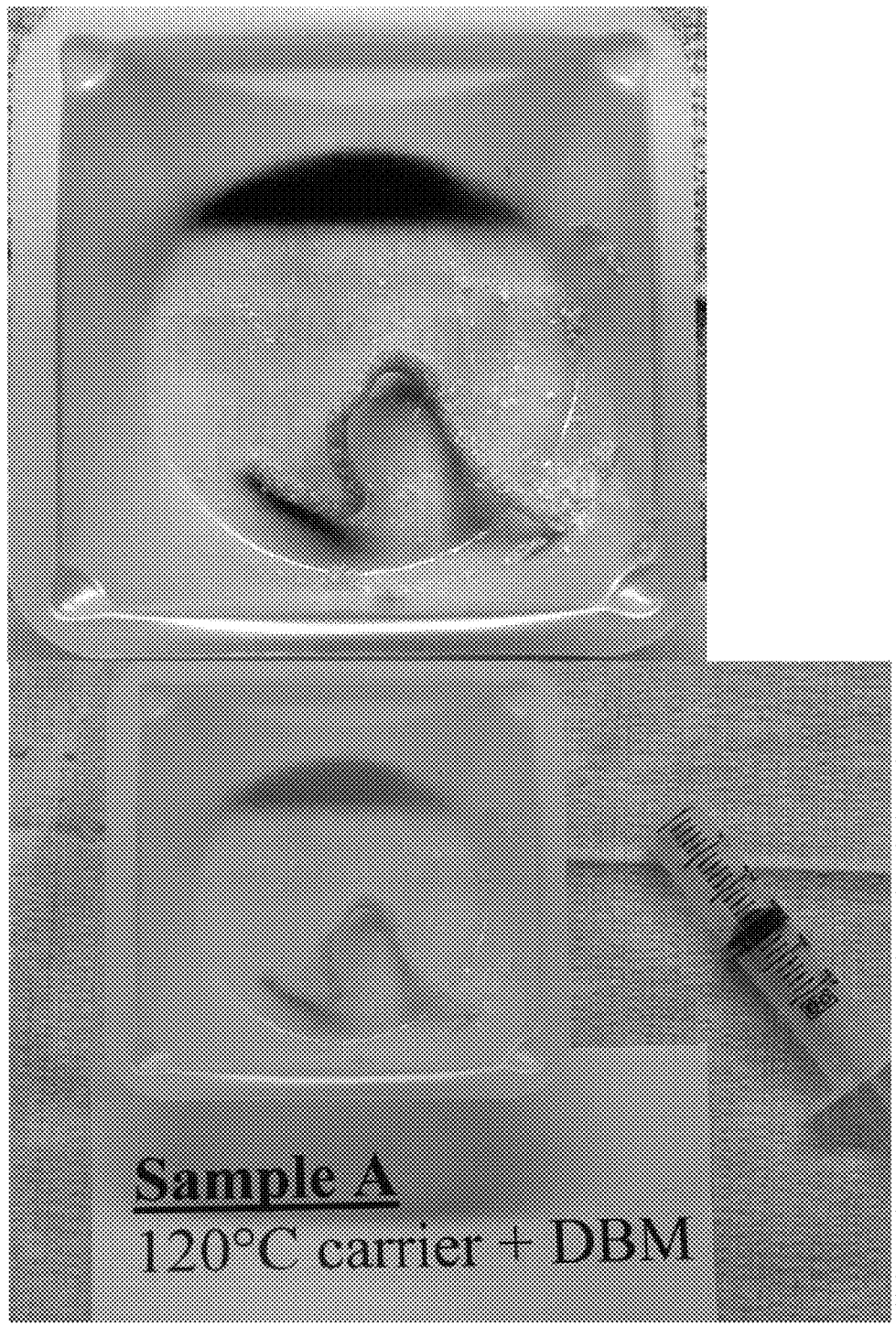
FIGS. 1A through 1C are photographs of putties that have been extruded from a syringe having a narrow tip. The different putties comprise carriers prepared from demineralized bone matrix at different processing temperatures.

The present disclosure relates to novel osteoinductive putties, carriers for such putties, compositions related to such putties, implants including such putties, kits for the use of such putties, and methods of making and using any of the foregoing. The osteoinductive putties comprise an osteoinductive substance, a liquid medium, and a carrier as described herein. The term putty includes pastes, gels, viscous suspensions, solutions, liquids, and mixtures, and generally refers to any material that is not completely solid. The present putties can be in the form of a viscous mixture or liquid, as described in more detail below. The present disclosure also relates to novel formed implants, implantable compositions for such implants, compositions related to such implants, kits for the use of such implants, and methods of making and using any of the foregoing. Although certain parameters are used as examples, the current disclosure should not be viewed as limited to such specifics.

An osteoinductive substance has at least some ability to promote or assist in bone growth, such as the ability to recruit and transform cells from the host which have the potential for repairing bone tissue. For example, demineralized bone matrix and osteoinductive proteins such as bone morphogenetic proteins (BMPs) are considered to be osteoinductive substances. Autograft, allograft, xenograft or recombinantly produced BMPs or other naturally produced or recombinant growth factors are also considered osteoinductive substances. Osteoinductive proteins include some of the proteins in the transforming growth factor-beta (TGF-beta) superfamily of proteins, which includes the bone morphogenetic proteins (BMPs), activins and inhibins.

The present osteoinductive putties and compositions can be osteoconductive as well as osteoinductive. When a substance is osteoconductive, it has at least some ability to provide support for the growth of new host bone. For example, demineralized bone matrix, intact bone allografts, calcium phosphate and hydroxyapatite are considered to be osteoconductive substances. The present osteoinductive putties and compositions can also be osteogenic as well as osteoinductive. When a substance is osteogenic, it includes cells such as osteoblasts that can form bone, or stem cells that can be turned into bone-forming cells. The present putties and compositions may also be provided in non-osteoinductive forms, and have utility as an inert osteoconductive carrier in a variety of applications. For example, a therapeutic non-osteoinductive putty may be implanted to promote healing at a bony site alone or in conjunction with other osteoinductive therapies, or in a non-bony site to promote, direct or control fibrous or cartilaginous healing, ingrowth or guided regeneration. Unless otherwise noted, all references to osteoinductive putties throughout this specification may also be applied to osteoconductive or inert non-inductive putties. The current putties may additionally be used or adapted for use in dental regeneration and cartilage regeneration applications.

Methods of Making Demineralized Bone Matrix

Demineralized bone matrix (DBM) is the product of removing at least some of the mineralized component from bone but retaining collagen and noncollagenous proteins, including growth factors. DBM can be made from a number of different starting materials, such as natural tissues or synthetic materials. For example, DBM can be made from human bone, non-human bone or a mixture thereof. DBM can be made from various types of bone, such as cortical, cancellous, trabecular, or mixtures thereof. DBM can take various physical forms. For example, DBM can be in the form of blocks, strips, cylinders, chips, cubes, shavings, particles or powders. When DBM is formed into chips, shavings, particles or powders, it is particularly desirable to combine the DBM with some sort of putty or other carrier to aid in handling and delivery to the desired treatment site.

Source materials for the DBM and/or collagen source can be autograft, allograft, xenograft, or transgenic materials. The use of autograft material (where the patient's own body provides the source for the material), allograft material (where another human provides the source material), xenograft material (where a different species provides the source) or transgenic material bone (where a transgenic species provides the source) is well known in both human and veterinary medicine. Xenograft or transgenic materials may require further treatments (e.g. chemical fixation) to minimize the level of immunogenicity in the material.

DBM is typically derived from bone from human donors. Alternatively, DBM is derived from bone from animal donors, such as porcine, ovine or bovine bone. Donated bone is removed and initially processed aseptically and/or treated to kill any infectious agents. The bone is then optionally particulated by milling or grinding and then the mineral component is extracted (e.g., by soaking the bone in an acidic solution). Alternatively, some or all of the calcium extraction may be performed prior to milling, grinding or shaping the bone, with the softening of the demineralized portion of the bone resulting in changes to stiffness and machineability. The remaining matrix is malleable when hydrated, and can be further processed and/or formed and shaped for implantation into a particular site in the recipient. The DBM can be processed into the form of blocks, strips, cylinders, chips, shavings, cubes, particles, or powders.

Tissue from a single donor (allograft or xenograft) is preferred due to favorable regulatory status as a minimally manipulated tissue product as well as reduced health risk and disease transmission risk as compared to tissue from multiple sources. Donor to donor variability exists in most forms of tissue implants, including DBM. Osteoinductivity and inflammatory response may vary from one donor to the next. Due to this variability, osteoinductivity testing is often a beneficial first step in selecting donor tissue for processing into any potentially osteoinductive composition.

Demineralized bone matrix prepared in this manner typically contains a variety of components including proteins, glycoproteins, growth factors, and proteoglycans. Following implantation, the presence of DBM induces cellular recruitment to the site of injury. The recruited cells may eventually differentiate into bone forming cells. Such recruitment of cells leads to an increase in the rate of healing and, therefore, to faster recovery for the patient. Accordingly DBM is considered to be an osteoinductive substance or material.

There are a number of different methods of producing DBM from the various starting materials. DBM is commonly prepared by acid extraction of bone, resulting in loss of most of the mineralized components but retention of collagen and noncollagenous proteins. Other methods include alkaline extraction of bone. Any process known to those familiar with the technology can be used. Some specific processes are discussed below merely for exemplary purposes.

In one method of demineralization, a section of source bone is treated to remove soft tissue, including marrow and blood, and is then perforated to form a multiplicity of holes of desired size, spacing, and depth. The perforated bone section is then immersed and demineralized in an acid bath (e.g., 0.6 Normal (N) hydrochloric acid (HCl)), and is further treated in a defatting solution to remove remaining marrow and intra-matrix cells. Following the perforating and defatting steps, the grafts can be freeze-dried and stored in sterile bags at conventional room temperature for periods of up to one year and perhaps longer prior to implantation or prior to use in the present methods of making a carrier, osteoinductive putty, or other implantable compositions.

In another method of making DBM, DBM is prepared by first removing all soft tissue and washing the bones in sterile deionized water. The cleansed bones are then extracted in a chloroform-methanol mixture, dried overnight, milled, sieved and decalcified in 0.6 N HCl for three to four hours. The resultant powder is rinsed with sterile deionized water to bring the pH to 3.5 or above and then lyophilized.

In yet another method of making DBM, DBM is prepared by soaking the bone segments for several minutes in a container with enough sterile ethanol to cover the tissue. The bone segments are milled and placed in a sieve. The milled bone material is cleaned with hydrogen peroxide, removed and rinsed with sterile water. The rinsed bone powder is added to sterile ethanol. The bone powder is then dried. The dried bone powder is transferred to the demineralization process. The bone powder is mixed with 0.6 N HCl until most of the mineral content is removed from the bone. The bone powder can be left for a longer period of time to fully demineralize the bone powder.

Other Osteoinductive Substances and Additives

In addition to or instead of DBM, other osteoinductive substances can be included in the present osteoinductive putties. Autograft, allograft, xenograft, transgenic or recombinantly produced osteoinductive substances can be employed. Preferably, natural (e.g., autograft, allograft or xenograft) osteoinductive substances can be employed, even more preferably those that are isolated or purified from natural tissues. BMPs or other naturally produced or recombinant growth factors and proteins, or fragments thereof having osteoinductive activity, can be included as the osteoinductive substance. Preferably, naturally produced growth factors and proteins or fragments thereof can be employed. Osteoinductive proteins include some of the proteins in the transforming growth factor-beta (TGF-beta) superfamily of proteins, which includes the bone morphogenetic proteins (BMPs), activins and inhibins. In some embodiments, the osteoinductive substance includes at least one growth factor selected from the BMPs which have osteoinductive activity, and other growth and differentiation type activities. These BMPs include BMP proteins BMP-2, BMP-3, BMP-4, BMP-5, BMP-6, BMP-7, BMP-9 (GDF-2), BMP-10, BMP-12, BMP-13, BMP-15, BMP-16, BMP-17, and BMP-18. BMPs may exist as dimers of the same monomeric polypeptides (homodimers) held together by hydrophobic interactions and/or one or more disulfide bonds or other molecular bonds. However, BMPs may also form heterodimers by combining different monomers (for example, a BMP-6 monomer associated with a BMP-2 or BMP-7 monomer). In the present putties and compositions, the osteoinductive substance can be a dimer (such as a homodimer or heterodimer) that comprises one or more of the foregoing BMPs or another osteoinductive protein, or a fragment thereof having osteoinductive activity. For example, BMPs can be provided in a mixture of homodimers and heterodimers. Alternatively recombinant heterodimeric BMP proteins can be employed. Heterodimeric BMP proteins are disclosed in U.S. Pat. Nos. 6,593,109 and 7,300,772 (Genetics Institute, Inc.) as being useful for treating bone defects, healing bone injuries and in wound healing in general. For example, the heterodimers may comprise a protein or fragment of any of the foregoing BMPs associated with a protein or fragment of another BMP. Other osteoinductive proteins include some of the proteins referred to as Growth and Differentiation Factors (GDFs), such as GDF-3, GDF-5, GDF-6, and GDF-10. Other osteoinductive substances are known to those familiar with the orthopedic field or those familiar with the mechanisms of bone growth, regeneration and healing. The osteoinductive putties can include other components. For example, one or more salts or ions can be included in the putties. Salts comprising calcium and/or phosphate can be included, such as calcium chloride, calcium sulfate, calcium phosphate, and calcium hydroxyapatite.

In addition to the osteoinductive substance, osteogenic substances and/or osteoconductive substances can also be added to the present osteoinductive putties. Examples of additional osteoconductive substances include allograft or xenograft bone (e.g. cortical cancellous chips), calcium phosphate and hydroxyapatite. Examples of additional osteogenic substances include osteoblasts, stem cells or multipotent adult progenitor cells (MAPCs) that can be turned into bone-forming cells.

Free radical scavengers can also be added to the DBM, osteoinductive substance, carrier, or osteoinductive putty in order to increase storage time. Free radical scavengers are thought to increase storage time by preventing or reducing oxidation. Examples of free radical scavengers include, but are not limited to, vitamin C, vitamin E and beta-carotene.

Methods for Making Carrier

For the present methods, the carrier can be produced from a collagen source. Collagen sources (e.g., tissues comprising fibrillar collagen, such as Type I or Type II collagen) include demineralized bone matrix (DBM), whole bone, bone chips, bone power, skin, tendons, ligaments, meniscus, and cartilage. Preferably the collagen source is or is derived from a natural tissue or otherwise naturally produced (e.g., from autograft, allograft or xenograft sources), but it is contemplated that the collagen source may be a synthetic material, such as collagen that is recombinantly produced. In some preferred embodiments, an amount of DBM is divided and a first portion is used to produce a collagen source and a second portion is used as the osteoinductive substance. Tissues comprising Type I collagen can be from human or non-human (autograft, allograft, transgenic and/or xenograft) sources, similar to the DBM. A mixture of various Type I collagen-containing tissues can also be used as the collagen source. Tissues comprising Type II collagen can be from human or non-human (autograft, allograft, transgenic and/or xenograft) sources, such as cartilage. A mixture of various Type II collagen-containing tissues can also be used as the collagen source. A mixture of various Type II and Type I collagen-containing tissues can also be used as the collagen source.

The collagen source can be in any physical form, such as bone shafts, whole or partial tendons, sections of dermis or other connective tissues, bone blocks, strips, cylinders, chips, cubes, shavings, fibers, particles, or powders. The use of smaller particles may result in higher dissolution of the collagen source during a denaturation process. The collagen source can optionally be mechanically processed to achieve a more uniform, consistent, or homogeneous makeup. The mechanical processing can occur prior to or after demineralization where the collagen source undergoes demineralization. If the collagen source is derived from bone, such as DBM, various types of bone can be used. For example, cortical, cancellous, trabecular or mixtures thereof can all be used.

In some embodiments, a carrier is made by subjecting DBM to a denaturation process at a suitable temperature, for example 120° C. or higher, for a suitable time period, for example 90 minutes or longer. It is theorized that the denaturation process yields a product in which a portion of the collagen in the DBM is denatured, a portion of the collagen in the DBM is fully intact and a portion of the collagen in the DBM is denatured and hydrolyzed. Collagen can be hydrolyzed to varying degrees by the denaturation processes described herein, providing collagen fragments of varying molecular weights.

Denaturing refers to separating strands of collagen. Collagen is the main protein of connective tissue in animals. The tropocollagen or collagen molecule subunit is made up of three polypeptide strands. There is some covalent crosslinking within the triple helices, and a variable amount of covalent crosslinking between tropocollagen helices, to form the different types of collagen found in different mature tissues. In bone, collagen triple helices lie in a parallel, staggered array. Collagen gives bone its elasticity and contributes to fracture resistance.

Hydrolyzing refers to breaking bonds between individual amino acids, which results in shorter strands. In various embodiments of the present methods, DBM subjected to a denaturation process undergoes at least some denaturation of the strands of the tropocollagen, and in some embodiments, hydrolyzation of bonds within some strands. Treating collagen under different conditions can lead to different compositions, with different degrees of denaturing and hydrolyzing leading to different mixtures of collagen fragments.

Various gelatins have previously been used as carriers for osteoinductive agents. Gelatin is formed from collagen which has been denatured and hydrolyzed to some extent. In general, the molecular weight of the fragments present in gelatins are similar in size. Due to their similarity of size, these particles can then line up to form an interconnective matrix of hydrogen bonds. Such a structure is typically considered a hydrogel.

In the present disclosure, denatured collagen refers to collagen in which the strands of the tropocollagen molecule are at least partially separated. Intact collagen refers to collagen in which the strands of the tropocollagen molecule are not separated. Hydrolyzed denatured collagen refers to collagen in which the strands of the tropocollagen molecule are at least partially separated and at least partially broken into shorter strands. In the present disclosure, hydrolyzed denatured collagen is not limited to particles that are similarly sized as in gelatin. The hydrolyzed denatured collagen of the present carriers will generally have some particles, fragments or strands that are smaller than those in a gelatin.

As one example of a denaturation process, a collagen source such as DBM is exposed to a denaturing solution. In the present disclosure, the term denaturing solution refers to the solution used in the processes described herein, and generally does not require that the solution independently cause denaturation outside the processes described herein. The denaturing solution can be selected from the group consisting of an acidic solution, a basic solution, or an enzymatic solution. The acid, base, or enzyme can be combined with water or a solution comprising water and some other component. For example, the other component could include a component normally found in animal blood serum (e.g., sodium chloride, potassium phosphate, sodium bicarbonate, or the like). The denaturing solution can be selected from solutions other than saline or water alone, though the denaturing solution can include water and/or sodium chloride in addition to an acid, a base or an enzyme. Alternatively or additionally, the denaturing solution can include an organic solvent such as ethylene glycol or glycerol. A potential advantage from using such a solvent is that the boiling temperature of the denaturing solution can be increased.

Suitable acidic denaturing solutions include hydrochloric acid (HCl), hydroiodic acid (HI), sulfuric acid ($H_2SO_4$), or another inorganic acid. Other acidic solutions can include acetic acid ($CH_3COOH$), aspartic acid ($HO_2CCH(NH_2)CH_2CO_2H$), lactic acid ($C_3H_6O_3$), fumaric acid ($HO_2CCH=CHCO_2H$), sorbic acid ($C_6H_8O_2$) and glutamic acid ($C_5H_9NO_4$), or another organic acid. A suitable concentration of acid can be selected. In some embodiments, the concentration of acid is from about 0.001 to about 5 N, alternatively from about 0.01 to about 1 N, alternatively from about 0.025 to about 0.1 N, or alternatively about 0.05 N. In some embodiments where an acidic HCl solution is used, the denaturing solution has a concentration from about 0.025 to about 0.1 N, or alternatively about 0.05 N. The concentration of acid may be selected based on the type of acid used and its dissociation constant.

Suitable basic denaturing solutions can include alkali metal base or alkali earth metal base, such as sodium hydroxide (NaOH), potassium hydroxide (KOH), zinc hydroxide ($Zn(OH)_2$) or calcium carbonate ($CaCO_3$). In some embodiments, the concentration of base is from about 0.001 to about 5 N, alternatively from about 0.01 to about 1 N, alternatively from about 0.025 to about 0.1 N, or alternatively about 0.05 N.

Suitable enzymatic denaturing solutions include bacterial collagenases (such as those collagenase preparations available from Worthington Biochemical Corporation, Lakewood, N.J.) and those mammalian matrix metalloproteinases that are active toward collagen (such as MMP-1). Enzymatic denaturing solutions are generally more expensive to purchase than acidic or basic denaturing solutions.

The collagen source is mixed with the denaturing solution to form a collagen source mixture. The collagen source can be allowed to swell for a period of time prior to heating. The time for which the collagen source is exposed to the denaturing solution can vary. For example, the time could be from about 1 minute to overnight, alternatively from about 2 to about 15 minutes, or alternatively about 10 minutes. When the denaturing solution is an enzymatic solution, it is preferred to maintain the collagen source mixture at ambient temperature or a temperature below about 55° C. for several hours or days before heating so that the enzymes can denature the collagen before being themselves denatured by heating.

The amount of denaturing solution added depends on the amount of collagen source used. The amount of solution should be sufficient to form a fairly dilute mixture. Preferably, the ratio of milliliters of denaturing solution to grams of collagen source is from about 20:1 to about 5:1, more preferably about 10:1. For example, in one embodiment about 10 milliliters (mL) of a 0.05 N HCl solution is added for each gram of collagen source. However, this ratio can be varied and still be effective. For example, 50 mL of 0.05 N HCl could be added to 4.5 grams (g) of DBM. Preferably the ratio of denaturing solution to collagen starting material is about 5:1 or higher, and/or 20:1 or lower, or 30:1 or lower. However the ratio can be lower than 5:1 or higher than 30:1. In general, the more denaturing solution that is added, the longer the drying or lyophilization process will take.

The collagen source is heated so that the collagen will be thermally denatured to a desired extent. It has been found that heating the collagen source mixture at 120° C. in an autoclave for 90 minutes produced a carrier having surprisingly good physical properties, such as extrudability, moldability, irrigation resistance, cohesion in solution, and adherence to glass and metal surfaces. However, it is also contemplated that other times and temperatures can be sufficient to provide a desired carrier. For example, it is contemplated that the collagen source mixture can be heated at a temperature greater than about 100° C. for 180 minutes or longer, to provide a desirable carrier. In other embodiments of the present methods, it is contemplated that it may be sufficient to heat the collagen source at a lower temperature, which in some circumstances may be sufficient to achieve the desired extent of thermal denaturation of collagen. For example, a lower temperature may be sufficient when the collagen source is a soft tissue such as a tendon, or the collagen source has been previously subjected to other processing such as enzymatic degradation.

In various embodiments, the present methods can include heating the collagen source to a temperature of at least about 65° C., alternatively at least about 70° C., alternatively at least about 75° C., alternatively at least about 80° C., alternatively at least about 85° C., alternatively at least about 90° C., alternatively at least about 95° C., alternatively at least about 100° C., alternatively at least about 101° C., alternatively at least about 102° C., alternatively at least about 103° C., alternatively at least about 104° C., alternatively at least about 105° C., alternatively at least about 106° C., alternatively at least about 107° C., alternatively at least about 108° C., alternatively at least about 109° C., alternatively at least about 110° C., alternatively at least about 111° C., alternatively at least about 112° C., alternatively at least about 113° C., alternatively at least about 114° C., alternatively at least about 115° C., alternatively at least about 116° C., alternatively at least about 117° C., alternatively at least about 118° C., alternatively at least about 119° C., alternatively at least about 120° C., alternatively at least about 121° C., alternatively at least about 122° C., alternatively at least about 123° C., alternatively at least about 124° C., alternatively at least about 125° C., alternatively at least about 126° C., alternatively at least about 127° C., alternatively at least about 128° C., alternatively at least about 129° C., alternatively at least about 130° C., alternatively at least about 131° C., alternatively at least about 132° C., alternatively at least about 133° C., alternatively at least about 134° C., alternatively at least about 135° C. The heating temperature can be at most about 240° C., alternatively at most about 220° C., alternatively at most about 200° C., alternatively at most about 180° C., alternatively at most about 160° C., alternatively at most about 155° C., alternatively at most about 150° C., alternatively at most about 145° C., alternatively at most about 140° C., alternatively at most about 139° C., alternatively at most about 138° C., alternatively at most about 137° C., alternatively at most about 136° C., alternatively at most about 135° C., alternatively at most about 134° C., alternatively at most about 133° C., alternatively at most about 132° C., alternatively at most about 131° C., alternatively at most about 130° C., alternatively at most about 129° C., alternatively at most about 128° C., alternatively at most about 127° C., alternatively at most about 126° C., alternatively at most about 125° C., alternatively at most about 124° C., alternatively at most about 123° C., alternatively at most about 122° C., alternatively at most about 121° C., alternatively at most about 120° C. The desired temperature can be one or more temperatures within a range, for example, between about 105° C. and about 135° C., alternatively between about 110° C. and about 125° C., or alternatively at about 120° C. Alternatively, any of the foregoing minimum temperatures or maximum temperatures can be combined to form a range, provided the selected maximum is higher than the selected minimum.

In various embodiments, the present methods can include heating the collagen source for a time of at least about 30 minutes, alternatively at least 60 minutes, alternatively at least 75 minutes, alternatively at least 80 minutes, alternatively at least 85 minutes, alternatively at least about 90 minutes, alternatively at least about 95 minutes, alternatively, at least about 100 minutes, alternatively at least about 105 minutes, alternatively at least about 120 minutes, alternatively at least about 135 minutes, alternatively at least about 150 minutes, alternatively at least about 165 minutes, alternatively at least about 180 minutes, alternatively at least about 195 minutes, alternatively at least about 210 minutes, alternatively at least about 225 minutes, alternatively at least about 240 minutes. The heating time can be at most about 72 hours, alternatively at most about 60 hours, alternatively at most about 48 hours, alternatively at most about 36 hours, alternatively at most about 24 hours, alternatively at most about 20 hours, alternatively at most about 18 hours, alternatively at most about 16 hours, alternatively at most about 14 hours, alternatively at most about 12 hours, alternatively at most about 10 hours, alternatively at most about 8 hours, alternatively at most about 6 hours, alternatively at most about 4 hours, alternatively at most about 2 hours. Alternatively, any of the foregoing minimum times or maximum times can be combined to form a range, provided the selected maximum is higher than the selected minimum.

The heating can be done using an autoclave, a hot plate or any other heater suitable for laboratory or industrial use. If an autoclave is used, the collagen source mixture comprising water can more readily be heated to a temperature of between about 100° C. and about 135° C., alternatively between about 110° C. and about 130° C., or alternatively at about 120° C. The autoclave pressure varies depending on the maximum temperature desired. For a given autoclave configuration and depending on the amount of collagen source mixture to be produced, the pressure within the autoclave unit may vary. For example, at 110° C., the autoclave pressure is at least about 8 pounds per square inch (PSI), alternatively at about 11-12 PSI at a temperature of 115° C., or alternatively at about 18 PSI while at 120° C. The heating is continued for a time between about 30 and about 180 minutes, alternatively between about 60 and about 120 minutes, or alternatively for about 90 minutes. During this heating process, the solution may become more viscous and achieve an amber/almond color. Additionally, the volume of the acidic solution may decrease. When a soft tissue is used as a collagen source, lower temperatures, for example between about 75° C. and about 100° C., may be suitable.

Alternatively, another heater could be used in the denaturation processes described herein. For example, a hotplate or burner could be used. If a hot plate is used, the collagen source mixture can be heated to a desired temperature, for example, between about 65° C. and about 120° C., alternatively between about 80° C. and about 110° C., or alternatively at about 100° C. When the denaturing solution comprises water, heating above 100° C. on a hot plate will generally result in some evaporation of the water. In the present methods, the heating can be continued until the volume of the collagen source mixture decreases by about 80%, which usually takes about 60 to about 90 minutes. The collagen source mixture will also become more viscous and will achieve an amber/almond color.

Dissolution of the collagen source can be enhanced during heating by the use of agitation and/or ultrasound. The dissolution can also be enhanced by use of pressure to raise the boiling point of the mixture. If the heated solution is subjected to an elevated pressure, allowing the development of elevated temperatures above 100° C., the collagen source is dissolved more readily.

After heating, the denatured collagen source mixture can then be allowed to cool. Cooling times can range from about 10 minutes to about 50 minutes, alternatively about 20 minutes to about 40 minutes or alternatively about 25 minutes to about 35 minutes. In general, it is sound practice to remove the denatured collagen source mixture from the autoclave within about 30 minutes after the conclusion of heating. The denaturing solution can be stirred during cooling in order to evenly distribute any material that has not dissolved. The cooling time can be varied and still be effective.

If the denaturing solution is acidic or basic, the denaturing solution can then be at least partially neutralized (rendered less acidic or less basic). When the denaturing solution is acidic, this can be done by testing the pH and adding a basic solution. When the denaturing solution is basic, an acidic solution can be added. The pH can be tested using a pH monitor, pH indicator strips or any other pH measuring method.

The neutralizing acidic or basic solution to be used can be chosen depending on the particular base or acid that was used in the denaturing solution. If hydrochloric acid was used in the denaturing solution, then suitable basic solutions for neutralizing the acid include sodium hydroxide (NaOH), potassium hydroxide (KOH), zinc hydroxide ($Zn(OH)_2$) or calcium carbonate ($CaCO_3$). If hydroiodic acid was used in the denaturing solution, then suitable bases include potassium iodide (KI) or sodium iodide (NaI) to neutralize the acid. If sulfuric acid ($H_2SO_4$) was used in the denaturing solution, then sodium hydroxide (NaOH) may be preferred to neutralize the solution. If acetic acid ($CH_3COOH$) was used in the denaturing solution, then zinc carbonate ($ZnCO_3$) may be preferred to neutralize the solution. If aspartic acid ($HO_2CCH(NH_2)CH_2CO_2H$) or lactic acid ($C_3H_6O_3$) was used in the denaturing solution, then calcium carbonate ($CaCO_3$) may be preferred to neutralize the solution. Other acids that can be used in the denaturing solution include stearic acid ($CH_3(CH_2)_{16}COOH$), fumaric acid ($HO_2CCH=CHCO_2H$), sorbic acid ($C_6H_8O_2$) and glutamic acid ($C_5H_9NO_4$). These acids can also be neutralized with sodium hydroxide (NaOH).

In some embodiments, a basic solution of sodium hydroxide (NaOH) is used to neutralize an acidic denaturing solution. Preferably the NaOH solution has a concentration ranging from about 1 to about 10 N, alternatively from about 4 to about 6 N, alternatively about 5 N. The amount of neutralizing base added depends on the type and molarity of the acid in the denaturing solution.

The neutralizing solution can be combined with water or a solution comprising water and some other component. For example, the other component could include a component normally found in animal blood serum (e.g., sodium chloride, potassium phosphate, sodium bicarbonate, or the like).

The neutralizing solution is added until the pH reaches a desired level, such as within about 4.0 to about 6.0, alternatively within about 4.0 to about 4.7, or alternatively about 4.4. The amount of neutralizing solution added can be selected based on various factors, including the amount of collagen source used, the amount of acid or base used in the denaturing solution, the pH level of the denatured collagen source mixture prior to neutralization, and the length of time that the denatured collagen source mixture cools outside of the autoclave. HCl has a relatively low vapor pressure and when it evaporates, the pH of the solution slowly increases. When the denaturing solution comprises 0.05 N HCl, it has been observed that if the denatured collagen source mixture is left for about 8 hours, the pH will increase to about 4.4 without the addition of a base.

The pH of the denatured collagen source mixture and osteoinductive putty can be carefully monitored and altered. The natural condition for blood plasma as well as synovial fluid, cerebrospinal fluid, aqueous humor (fluid within the globe of the eye) is a pH of about 7.3-7.4. However, the body has many mechanisms to maintain its biochemical balance. The blood pH can be adjusted by several means to its normal, physiologic pH. Hence the presence of a non-physiologic material at the site of a bleeding bone wound will eventually be overcome and any non-biocompatible condition will return to normal pH. It is recognized that osteoinductive substances such as BMPs may be stored at slightly acidic pH. A slightly acidic or basic pH is believed to improve processing as compared to a neutral or more nearly neutral pH by more easily maintaining the collagen source mixture in suspension or solution throughout processing.

The collagen source mixture after heating can be stored or further processed, such as by drying and/or freezing. For example, the neutralized mixture can then be dried. This can be done using a variety of methods, including freeze-drying, air drying at room temperature, drying in an oven or using a heater, or other desiccation techniques. For example, the carrier can be made by evaporating the liquid present in the collagen source mixture after heating. The liquid may be evaporated until the water content is reduced so as to provide a desired consistency for the carrier. If the drying is carried out under conditions wherein the denaturing solution is volatile, this may also allow for neutralization of an acidic or basic solution during drying.

If freeze-drying is carried out on the acidic, basic, or neutralized solution, the solution can be allocated into small portions, for example 5 mL portions. These portions can then be exposed to a temperature sufficient to freeze the mixture, for a time sufficient to freeze the mixture. For example, an acidic solution exposed to a temperature of about −80° C. for about 30 minutes will freeze.

After freezing, a solid carrier intermediate product is provided. The solid carrier intermediate product can then be lyophilized to provide a dry solid carrier. The solid carrier may be suitable for use as a carrier, though it may contain residual chemicals from the denaturing solution and/or neutralizing solution. Lyophilization can be done with a lyophilizing machine until the carrier is substantially free of moisture, as is well-known to those familiar with the technology. Lyophilization volatilizes off residual chemicals, produces a more stable intermediate for storage and handling in-process, and follows pharmaceutical industry processing standards. Typically lyophilization results in a residual moisture content of about 10 weight percent or less, alternatively about 6 weight percent or less, alternatively about 3 weight percent or less, alternatively about 2 weight percent or less, alternatively about 1 weight percent or less. After the denatured collagen source mixture is dried, it can be stored in a manner that prevents air moisture from rehydrating the carrier.

Physical Properties of Carriers

The present carriers can be prepared by one or more embodiments of the methods described above, or by other methods that yield a carrier having the same or similar physical properties. The osteoinductive putty of the present disclosure comprises an osteoinductive agent and a carrier. The carrier can be made as described above and comprises a mixture of collagen fragments. For example, the carrier can include a mixture of collagen fragments having a substantially uniform molecular weight distribution over a relatively wide range. In some embodiments, the carriers have a characteristic molecular weight distribution of collagen fragments, such as the molecular weight distribution shown in FIGS. 2A through 2D. Alternatively or additionally, the present carriers can have a mixture of collagen fragments having an SDS-PAGE profile that does not have a banded region within certain molecular weight ranges. For example, in some embodiments, the SDS-PAGE profile does not have a banded region between 29 kDa and 97 kDa, or between 39 kDa and 66 kDa, or between 45 kDa and 66 kDa. In some embodiments, the SDS-PAGE profile has a discrete band at a location between 15 kDa and 20 kDa, and/or a partially discrete band between 20 kDa and 25 kDa. Alternatively or additionally, the carrier can include a mixture of intact collagen, denatured collagen and denatured, hydrolyzed collagen.

By use of the phrase "does not have a banded region," the inventors intend to include the case where the present carriers may be measured against or compared to certain properties of known materials such as porcine gelatin, Type-I collagen, unprocessed collagen, or collagen processed at a different time and/or temperature than that of the present carriers. For example, it may be observed that in some embodiments the SDS-PAGE profile includes a region which exhibits a substantially reduced prominence of discrete, discernable, well defined, sharp, intense, narrow, or noticeable bands, banding or banded regions when compared to other samples including porcine gelatin, Type-I collagen, unprocessed collagen, or collagen processed at a different time and/or temperature than that of the present carriers. In contrast to porcine gelatin, Type-I collagen, unprocessed collagen, or collagen processed at a different time and/or temperature than that of the present carriers, the present carriers exhibit a relatively diffuse, smoother and broader region (without prominent, intense, or discernable bands in that region) of their SDS-PAGE profiles. Such a profile is intended to be encompassed by the phrase "does not have a banded region". This staining pattern indicates a region of substantially more uniform molecular weight distribution of collagen fragments. For example, in some embodiments, the SDS-PAGE profile displays a relatively diffuse and smoother region between 29 kDa and 97 kDa, or between 39 kDa and 66 kDa, or between 45 kDa and 66 kDa. In some embodiments, the SDS-PAGE profile has a relatively prominent discrete band at a location between 15 kDa and 20 kDa, and/or a partially discrete band between 20 kDa and 25 kDa, as compared to similarly processed stains of porcine gelatin, Type-I collagen, unprocessed collagen, or collagen processed at a different time and/or temperature than that of the present carriers.

The present carriers in wet form, such as when combined with a liquid medium, can be in the physical form of a putty, which includes pastes, gels, viscous suspensions, solutions, liquids, and mixtures, and generally refers to any material that is not completely solid. The present carriers have unexpectedly improved properties over previously used materials. Without being bound by theory, it is believed that the improved properties of the present carriers are attributable to its molecular weight distributions of collagen fragments. Surprisingly the molecular weight distributions identified for the present carriers result in the carriers having improved physical properties compared to the properties of other materials such as gelatin. For example, the present carriers do not gel like gelatins and do not form hydrogels.

In this regard, various embodiments of the present carrier are not gelatins but rather are entirely new materials in the form of a highly viscous liquid.

Collagen fragments are polypeptide chains having the same general sequence and proportion of amino acids that are present in collagen. Collagen fragments can be obtained by denaturing and hydrolyzing native collagen, such as the fragments resulting from treating collagen as described in the present methods. As another example, synthetic collagen fragments could be produced by using recombinant methods, by generating polypeptides of appropriate content and length.

Various embodiments of the present carriers contain a high proportion of collagen fragments that are smaller than the collagen fragments found in traditional gelatin. When various embodiments of the present carrier have collagen fragments of an appropriate molecular weight distribution, it is theorized that the carrier does not form a relatively rigid lattice structure at the molecular level. Accordingly, when placed in a mold at room temperature, the carrier will not maintain the shape of the mold under pressure after the mold is removed. The carrier will continue to flow as a highly viscous cohesive liquid. Furthermore, reducing the carrier's temperature below room temperature to a temperature above the freezing point of the liquid medium does not result in a rigid, latticed structure.

The present disclosure provides carriers that have a high hygroscopic capacity (i.e., capacity to take up water or other solutions). Once hydrated with an appropriate amount of water, such carriers form a viscous liquid which is highly resistant to irrigation and highly resistant to dissolution or break up when exposed to water, blood or other solutions. The present osteoinductive putties have a high cohesiveness in solution (e.g. when submerged in or irrigated with water or other media such as saline or blood). Various embodiments of the present carrier have a dissolution time of at least about 3 minutes, alternatively at least about 6 minutes. The dissolution time of various embodiments of the present carriers and putties were determined as described in Example 18. Various embodiments of the present carriers have an irrigation resistance time of at least about 5 minutes, alternatively at least about 10 minutes. The irrigation resistance times of various embodiments of the present carriers and putties were determined as described in Example 19. The present carriers perform well in surgical procedures because they tend not to swell and are not washed away by blood or by irrigation of the surgical site. Irrigation resistance and dissolution resistance can be measured in water or in other solutions such as blood or saline. Blood is typically believed to be a more challenging medium for irrigation resistance and for dissolution resistance.

The present disclosure provides carriers that have a creep viscosity between about 5000 Pas and 50000 Pas, alternatively about 10826.62 Pas. The present disclosure provides carriers that have a shear rate of about 0.0167 1/s. The present disclosure provides carriers that have a creep rate of about 0.00022 rad/s. The present disclosure provides carriers that have an elastic index of about 0.5586. Procedures for determining creep viscosity, shear rate, creep rate, and elastic index are discussed in Example 21.

Methods of Making an Osteoinductive Putty

The present osteoinductive putties comprise an osteoinductive substance and a carrier. The carrier comprises a mixture of collagen fragments and can be made as described above. The osteoinductive putty can be in the form of a paste, viscous suspension or another form. The present osteoinductive putties are shapeable, malleable, flowable, injectable and/or pourable. To form the desired osteoinductive putty, the carrier, an osteoinductive substance, and a liquid medium are combined to form a composition having the desired consistency or properties.

The carrier can be prepared in dry form as outlined above. The carrier can be dried as also outlined above. The dry carrier can be further prepared for inclusion in the putty by cutting, shaping or grinding into blocks, strips, cylinders, chips, shavings, cubes, particles, or powders. This can be done using a variety of cutting, shaping or grinding methods. For example, one could use hand tools, power tools, or machine tools such as a saw, a drill, a chisel, a rotary cutting tool, a mortar and pestle, a cryomill, a coffee grinder, a blender or do the grinding by hand. The carrier can then be run through a sieve to remove any residual chunks. In some embodiments, a 850 micro sieve is used. Residual pieces of carrier can then be reground until they pass through the sieve.

Particle size may affect performance. Larger particle size tends to weaken particle to particle interactions within the carrier or osteogenic substance, while smaller particle size tends to strengthen these particle to particle interactions. Particle size may be controlled in the source DBM prior to processing to form a carrier. Particle size may be independently controlled in the osteoinductive substance prior to mixing with the carrier to form a putty. Particle size may be independently controlled in the ground carrier used to mix the putty. Particle size may be controlled in the mixed dry carrier and osteoinductive substance together. In some embodiments, the osteoinductive substance has a maximum particle size of less than about 2 centimeters, alternatively less than about 1 centimeter, alternatively less than about 900 microns, alternatively less than about 850 microns, alternatively less than about 600 microns, or alternatively less than about 400 microns. In some embodiments, the osteoinductive substance has a minimum particle size of more than about 60 microns, alternatively more than about 100 microns, alternatively more than about 125 microns, alternatively more than about 250 microns, alternatively more than about 400 microns, alternatively more than about 600 microns, or alternatively more than about 850 microns. In some embodiments, the dry carrier has a maximum particle size of less than about 2 centimeters, alternatively less than about 1 centimeter, alternatively less than about 900 microns, alternatively less than about 850 microns, alternatively less than about 600 microns, or alternatively less than about 400 microns. In one embodiment, the dry carrier has a minimum particle size of more than about 60 microns, alternatively more than about 100 microns, alternatively more than about 125 microns, alternatively more than about 250 microns, alternatively more than about 400 microns, alternatively more than about 600 microns, or alternatively more than about 850 microns. Alternatively, any of the foregoing minimum and maximum values can be combined to form a range, provided the selected maximum is higher than the selected minimum.

The osteoinductive substance can be DBM, mineralized or demineralized whole bone, bone pieces, BMPs, growth factors or some combination thereof. The bone that is used (either as whole bone or bone pieces, or as the source material to make one of the other osteoinductive agents) could be human or non-human bone. The bone that is used can be demineralized (DBM) or non-demineralized bone, or a mixture thereof. The bone that is used can be cortical bone, trabecular bone, cancellous bone, or a mixture thereof. The osteoinductive substance can be in the physical form of bone shafts, blocks, strips, cylinders, chips, shavings, cubes, particles, or powder.

A liquid medium can be combined with the dry carrier to make a wet carrier, and/or can be combined with the dry carrier and osteoinductive substance to make an osteoinductive putty. In some embodiments the liquid medium is water. Distilled, deionized, or sterilized water could be used. The water can be sterile water for injection or sterile saline solution or can comprise other components, such as those normally found in blood. Soluble calcium can be attracted to the surgical site by using a sodium phosphate buffer. The liquid medium could alternatively be a buffered solution, such as one of the buffered solutions described in U.S. Pat. No. 6,679,918. Other liquid media for making a putty include phosphate buffered solution (PBS), low molecular weight alcohols such as ethanol and butanol, high molecular weight alcohols such as decanol, diols such as glycerol, and other liquid that can participate in hydrogen bonding. A phosphate buffer will attract calcium cations to the site from the surrounding healthy bone and create an equilibrium concentration of the calcium at the site of healing where it is most desirable to grow new bone.

The liquid medium can be at room temperature. Alternatively, the liquid medium could be heated before, during or after mixing to assist in dissolution of the dry carrier in the liquid medium. For example, the liquid medium could be heated to a temperature of about 55° C. or lower, alternatively about 37° C. or lower.

It is contemplated that other active agents can optionally be added to the carrier or implantable composition instead of or in addition to the osteoinductive substances. Other medically useful substances can be included in the present compositions by adding those substances to the carrier. Such substances include collagen and insoluble collagen derivatives, hydroxyapatite and soluble solids and/or liquids dissolved therein, and extracellular matrices such as those from the small intestine submucosa and urinary bladder. Other substances that can be included are antiviricides such as those effective against HIV and hepatitis; antimicrobial and/or antibiotics such as erythromycin, bacitracin, neomycin, penicillin, polymyxin B, tetracycline, viomycin, chloromycetin, streptomycin, cefazolin, ampicillin, azactam, tobramycin, vancomycin, clindamycin and gentamycin; antineoplastics; and anti-inflammatories such as steroids and non-steroidal anti-inflammatory drugs (NSAIDs). It is also envisioned that one or more of the following can be added to the present compositions: amino acids, peptides, proteins, small interfering RNAs, vitamins, co-factors for protein synthesis; hormones; endocrine tissue or tissue fragments; synthesizers; enzymes such as collagenase, peptidases, oxidases; polymer cell scaffolds with parenchymal cells; angiogenic drugs and polymeric carriers containing such drugs; collagen lattices; biocompatible surface active agents, antigenic agents; cytoskeletal agents; cartilage fragments; living cells such as chondrocytes, bone marrow cells, mesenchymal stem cells or multipotent adult progenitor cells (MAPCs); natural extracts; tissue transplants; bioadhesives; transforming growth factor (TGF-beta); insulin-like growth factor (IGF-1); growth hormones such as somatotropin; bone digestors; antitumor agents; fibronectin; cellular attractants and attachment agents; immuno-suppressants; permeation enhancers, e.g. fatty acid esters such as laureate, myristate and stearate monoesters of polyethylene glycol, enamine derivatives, alpha-keto aldehydes.

The osteoinductive putties can include other components. For example, one or more salts or ions can be included in the putties. Salts comprising calcium and/or phosphate can be included, such as calcium chloride, calcium sulfate, calcium phosphate, calcium hydroxyapatite, sodium phosphate, and others.

The relative amounts of carrier, osteoinductive substance, and liquid medium used to form an osteoinductive putty or other implantable composition vary based on the temperature of the heating process used during carrier formation. Higher heat treatment process temperatures and longer heat treatment process times generally correlate to lower water requirements to create a finished putty. For a carrier that was autoclaved at 120° C., one possible mixture of DBM, carrier, and water is 29 weight percent, 37 weight percent, and 34 weight percent respectively. Another possible mixture of DBM carrier and water is 32 weight percent, 24 weight percent, and 44 weight percent, respectively. If a temperature other than 120° C. is used when autoclaving the carrier, then the proportions of the DBM, carrier and water need to be varied to achieve the desired consistency. The proportions of DBM, carrier and water may also vary where other heating elements are used.

Lower water content is regarded as beneficial to allow a higher concentration of active DBM in the putty. The present carriers and putties may be hydrated with small amounts of water and still produce a flowable, highly viscous fluid with desirable handling properties. In some cases as little as 10%, alternatively 20%, alternatively 30%, water may be used to hydrate an osteoinductive putty or carrier. Lower hydration states may require more careful and complete mixing and may be more susceptible to drying out and other effects over time with storage, handling and use. Therefore, it is desirable and beneficial in some cases to add a greater amount of water for ease of manufacture, distribution, storage, handling and use during surgery. In some cases 30 weight percent, alternatively 40 weight percent, alternatively 50 weight percent, alternatively 60 weight percent, alternatively 70 weight percent, alternatively 80 weight percent, alternatively 90 weight percent may be used to hydrate an osteoinductive putty or carrier.

The handling properties of the carrier or osteoinductive putty may be influenced by the amount of water or other fluid added for hydration. The present putties provide excellent handling characteristics, including robust consistency, strong cohesive properties, self-adhesion (the ability to stick to themselves more readily than they stick to other objects such as latex or nitrile gloves), moldability (ability to accept and hold a formed shape), dissolution resistance (ability to maintain shape, even when exposed to blood or water), and extrudability under reasonable manual force from typical syringes or storage devices. The present putties are also remarkable in that in some embodiments they form a viscous liquid which retains properties of self-adhesion, moldability, irrigation resistance, and dissolution resistance even after being extruded through a syringe or manually manipulated or formed into shape. Alternatively, certain embodiments of the present putties form a viscous liquid which retains properties of self-adhesion, moldability, irrigation resistance, and dissolution resistance even after being extruded through a syringe, manually manipulated into a formed shape such as a ball or bead, then extruded again through a syringe one or more times.

For the temperatures discussed above, the amount of osteoinductive substance that is added to form the final product usually will be from about 5 to about 50 percent by weight, based on the total weight of the suspension, alternatively from about 15 to about 35 percent, or alternatively from about 20 to about 29 percent. The amount of carrier that is added to form the osteoinductive putty usually will be from about 5 to about 50 percent by weight, based on the total weight of the suspension, alternatively from about 20 to about 42 percent, or alternatively from about 27 to about 38 percent. The amount of liquid medium that is added to form the osteoinductive putty usually will be from about 10 to about 55 percent by weight, based on the total weight of the suspension, alternatively from about 20 to about 54 percent, or alternatively from about 29 to about 53 percent.

Another advantage of the present carriers is the ability to form a putty with a relatively small amount of liquid medium. More particularly, it has been found that osteoinductive putties having excellent physical properties can be made with a relatively small amount of water. Hence, embodiments of the present osteoinductive putties can be made which comprise water in an amount less than about 60%, alternatively less than 58%, alternatively less than 56%, alternatively less than 54%, alternatively less than 52%, alternatively less than 50%, alternatively less than 49%, alternatively less than 48%, alternatively less than 47%, alternatively less than 46%, alternatively less than 45%, alternatively less than 44%, alternatively less than 43%, alternatively less than 42%, alternatively less than 41%, alternatively less than 40%, alternatively less than 39%, alternatively less than 38%, alternatively less than 37%, alternatively less than 36%, alternatively less than 35%, alternatively less than 34%, alternatively less than 33%, alternatively less than 32%, alternatively less than 31%, alternatively less than 30%, alternatively less than 29%, alternatively less than 28%, alternatively less than 27%, alternatively less than 26%, alternatively less than 25% of the putty or composition.

The carrier can be mixed with the osteoinductive substance prior to adding the liquid medium. Alternatively, the carrier can be mixed with the liquid medium prior to adding the osteoinductive substance. Alternatively, the osteoinductive substance can be mixed with the liquid medium prior to adding the carrier. As the carrier is added to the liquid medium, the mixture will become viscous. At some point, a viscous suspension will be formed from the mixture of carrier, liquid medium and osteoinductive substance. More osteoinductive substance can be added or the swelling time can be increased in order to achieve a desired level of viscosity (e.g. paste-like or putty-like texture). Alternatively, carrier alone can be mixed with a suitable liquid medium to make a non-inductive viscous liquid carrier or manufacturing intermediate suitable for the formation of other various finished products.

The osteoinductive putty can then be loaded into syringes or other packaging for storage and use. Preferably the packaging is well suited for use in a medical and/or clinical environment. For example it can be durable, flexible and easy to handle. The packaging can also be barrier resistant to chemicals, grease, moisture, viruses and bacteria. The package could be sterile. In preferred embodiments the package is sealed, for example, it is sealed so that it is moisture resistant. As another example, a hermetically sealed package is sealed in an airtight manner. Examples of suitable materials for packaging and sealing the putty include thermoplastic films, polyester films, polyethylene fibers, para-aramid fibers and combinations thereof. For surgical applications the packaging could be a double pouch. The double pouch could be made up of an inner package and an outer package. The inner package can be made of a polyester film, such as Mylar®, and a polyethylene film, such as Tyvek® (both available from DuPont). The outer package can be made of a moisture resistant foil bag made of aluminum and transparent plastic with a Tyvek® Header pouch.

In embodiments where syringes are used, the syringes can be stored in such a manner as to keep them sterile. For example they can be irradiated and stored in vacuum packed bags. The moisture barrier properties of the syringe or package can have an impact on the stability and other properties of the osteoinductive putty. If the putty in placed in a package that has some degree of permeability to water, the putty may gain or lose moisture (water content), which may affect extrudability, cohesiveness and other properties.

Accordingly, another aspect of the present disclosure is a kit comprising the osteoinductive putty disposed in a suitable package, such as a syringe or a dual chamber package. In some embodiments, the osteoinductive putty is hermetically sealed in the package.

In certain embodiments where a syringe is used, the syringe barrel, plunger tip, plunger, or cap may each be made of polypropylene, polycarbonate, silicone, neoprene, santoprene, or any other suitable engineered thermoplastic or other resin commonly used in the medical device industry. In some embodiments, the package comprises a syringe having an opening at a first end and a plunger at a second end, wherein the putty is disposed inside the syringe, a removable cap attached to the opening of the syringe so as to form a seal. In some embodiments of the present kits, the putty can be extruded from a typical medical product delivery device or package such as a polypropylene syringe by pressure on the plunger of about 15 to 150 Newtons or higher. The type and configuration of the syringe may influence the specific force required to extrude a given putty.

The pH of the final putty can be in the range of about 4 to about 8, alternatively from about 4 to about 7. The pH of the final putty can be tested using a flat surface electrode if desired. If water was used as the liquid medium, the pH will be from about 4.0 to about 4.7.

Methods of Using an Osteoinductive Putty

Bone defects are generally viewed as being an imperfection or void in a bone tissue, which is of sufficient physical dimensions as to not heal spontaneously within a desired time period. Bone defects can include fractures, cracks, and osteosarcomas (bone cancer lesions), among others. Bone compositions in the form of putties, gels or pastes are utilized clinically to aid or improve healing of the osseous defect.

Bone compositions are also used to correct surgical bone defects that can be caused by trauma, pathological disease, surgical intervention or other situations where defects need to be managed in osseous surgery. Bone compositions are also commonly used to augment healing in the treatment of a broad range of musculoskeletal disorders. Bone compositions have been effective in reconstruction or replacement of bone defects, to augment fracture repair, to strengthen arthrodeses and to fill defects after treatment of tumors.

Those familiar with the technology will recognize the many orthopedic applications of the osteoinductive putties of this disclosure. However, by way of illustration rather than limitation, for purposes of arthrodesis of the spine, one mode of using this composition would be at an early stage of vertebral disk degeneration or subsequent to trauma. Diagnosis of trauma or degeneration is followed by formation of a small orifice, or a plurality of small orifices in the intervertebral cartilage at the site of degeneration. The osteoinductive putty is then injected into the intervertebral space to aid in inducing arthrodesis. A similar procedure could be used with other joints or bone damage.

The osteoinductive putties of this disclosure can be applied to a bone defect in a variety of ways. It is desirable to have the bone defect filler in the form of a stable, viscous putty or paste to facilitate the placement of the bone growth medium into the surgical site which is usually uneven in shape and depth. The surgeon can then pack the composition into the bone defect. The surgeon can take the putty on a spatula or other instrument and trowel it into the site. The surgeon can also use his/her fingers to shape the osteoinductive putty into the proper configuration to fit the site being corrected. The present osteoinductive putty is particularly advantageous for implantation by hand because there is little loss of material when handled by latex gloves.

The osteoinductive putty can be placed into a syringe or other package for easy storage and application. Preferably, the osteoinductive putty is placed into the syringe or package soon after the liquid medium is added to the other materials, since exposure to open air may result in moisture loss over time. It may be desirable to have the packages ready for loading before the liquid medium is combined with the other materials. In order to ensure that the putty has the desirable consistency, a small portion of the putty is placed into the rear of the syringe. The plunger is then inserted into the rear of the syringe and placed in an upright position with the ejection end of the syringe putting downwards. A reasonable manual force (such as between about 50 and about 300 Newtons) is then applied to the plunger. If the putty in the syringe is extruded, the putty has the desired density and physical properties. The syringes can be irradiated and stored for later use. The syringe or other package can be hermetically sealed to prevent or reduce the loss of moisture from the putty or loss of sterility. Sealing the package using moisture resistant packaging allows for extended storage of the putty in a ready to use form. Such packaging allows for the putty to remain in a hydrated form. The syringes can be sealed in a clear foil pouch, and the syringes and pouches can be sterilized, such as by low dose gamma irradiation.

The surgeon can later inject the osteoinductive putty into the affected area of the bone. This is done by injecting the syringe into the area of the bone defect and applying pressure to the plunger. Sufficient pressure is supplied to the plunger to eject the desired amount of osteoinductive putty. The amount of osteoinductive putty desired and the required force will vary depending on the size and shape of the affected area of the bone. The putty can be further manipulated after ejection from the syringe either by hand or with a spatula or other instrument.

In some embodiments, the osteoinductive putty components (the carrier and osteoinductive substance) and means for applying the osteoinductive putty (for example, syringe or spatula) can be provided in a unitary kit. In other embodiments, the osteoinductive substance and the carrier can be prepared under sterile conditions and stored separately, or mixed and stored together, for later use. To facilitate clinical usage of the present putties, carriers, and compositions, the osteoinductive substance and the carrier can be packaged separately and combined at the time of usage. In other embodiments, the components can be combined to produce an osteoinductive putty or other implantable composition, which is then packaged, in a premixed formulation.

A premixed osteoinductive putty provides the advantage of requiring very little preparation by the individual clinician at the time of usage. In some embodiments, the osteoinductive putty can be stored in an implantation device, such as a syringe, which will be used to apply the composition to a bone defect site. The osteoinductive putty can, for example, be stored in a 1 to 10 cc syringe (such as a 1 cc, 3 cc, or 5 cc syringe) that is capable of being coupled to a large gauge delivery tube/needle of appropriate length and inside diameter. In this regard, a delivery tube with an inside diameter of not less than 13 gauge is appropriate for the injection delivery into an implant site.

For on-site preparation, the carrier and osteoinductive substance can be provided in freeze-dried aliquots that are mixed and rehydrated just prior to being combined for use in clinical applications, in some embodiments. On-site preparation has the advantage of increasing the ability to vary the concentrations and quantities of the carrier and osteoinductive substance used in preparation of the osteoinductive putty. Furthermore, on-site preparation permits the addition of optional components at the discretion of the clinician.

Physical Properties of Osteoinductive Putty

The osteoinductive putty of the present disclosure comprises an osteoinductive substance and a carrier. The carrier can be made as described above and comprises a mixture of collagen fragments. For example, the carrier can include a mixture of collagen fragments having a substantially uniform molecular weight distribution over a relatively wide range. As other examples, the mixture of collagen fragments can have an SDS-PAGE profile that does not have a banded region within certain molecular weight ranges. As another example, the carrier can include a mixture of intact Type I collagen, denatured Type I collagen and denatured, hydrolyzed Type I collagen. It has been found that the particular mixture of collagen fragments can have a significant effect on physical properties (such as extrudibility, moldability, solubility, cohesivity, and others), and the present disclosure identifies carriers having novel mixtures of collagen fragments, which results in carriers having excellent physical properties.

Bloom strength is a measure of gel strength. As discussed in Example 20, some embodiments of the present osteoinductive putties do not have a measurable Bloom strength, because they fail to trigger the initial 4 g probe resistance force required to measure Bloom strength.

The present osteoinductive putties also have excellent physical properties and are generally superior to many previously used materials. For example, various embodiments of the osteoinductive putties are resistant to irrigation. In some embodiments, the putties are formulated with relative amounts of carrier, osteoinductive substance, and liquid medium such that the putties do not wash away under the pressure of a surgical lavage (about 150 mm Hg). As another example, the putties are not carried away by body fluids at the surgical site. As yet another example of their physical properties, various embodiments of the osteoinductive putties can adhere to metals, which can be useful to the manufacturer of the putty as well as to clinician. This can be particularly useful when attempting to apply the bone graft at an interface between bone and a metal implant. Various embodiments of the osteoinductive putties do not leave a substantial residue on latex or nitrile gloves, and can be manipulated without easily falling apart in a wet environment such as a surgical site. The present putties can be handled and shaped by a surgeon to form a desired shape or fit a desired surgical site.

Various embodiments of the present osteoinductive putties are highly resistant to taking up water or other solutions and are resistant to irrigation. The present osteoinductive putties have a high cohesiveness in solution (e.g. water or other media such as saline), making them less likely to leave the site of implantation. The high cohesiveness in solution is demonstrated by a high cohesion time in solution. Specifically, the present osteoinductive putties have a cohesion time of about 3 minutes or longer, or alternatively of about 6 minutes or longer, and/or an irrigation resistance time of about 5 minutes or longer or alternatively of about 10 minutes or longer. This allows the osteoinductive putties to be irrigated or completely submerged in a solution and subsequently handled without loss of physical properties.

The present osteoinductive putties also have excellent extrusion properties. The present osteoinductive putties retain good moldability and cohesiveness after extrusion. This allows for desirable surgical performance, in that the putty can be molded to fit a surgical site following extrusion from a syringe or other delivery device. The present osteoinductive putties exhibit consistent and reliable extrusion of a smooth continuous or semi-continuous bead of putty, with a reasonable extrusion force even following exposure to air. The putties can be extruded, such as in use of a syringe, with a moderate manual force (for example, about 2 to about 200 Newtons). Surprisingly, after the putty has been extruded, the putty can be loaded back into a syringe and extruded again without showing a loss of cohesiveness, such as crumbling or shredding. The putties can be extruded at least two, three or four times without exhibiting substantial loss of cohesiveness. In some embodiments and with some syringe configurations the putties may have higher extrusion force requirements (for example, about 50 to about 500 Newtons).

The present disclosure provides osteoinductive putties that have a creep viscosity between about 11000 Pas and about 48000 Pas, alternatively about 38428.102 Pas. The present disclosure provides carriers that have a shear rate of about 0.0047 1/s. The present disclosure provides carriers that have a creep rate of about 0.00006 rad/s. The present disclosure provides carriers that have an elastic index of about 0.531. Procedures for determining creep viscosity, shear rate, creep rate, and elastic index are discussed in Example 21.

Methods for Making a Formed Implant

In some embodiments, an implantable composition suitable for making, or for use as, a formed implant is made by subjecting a collagen source to a denaturation process at a suitable temperature for a suitable time. Formed implants may form a hydrogel, or partial hydrogel through at least some of their volume under various conditions of temperature and hydration. Formed implants are therefore not necessarily extrudable or moldable following extended storage to the same extent as osteoinductive putties. The present disclosure, however, provides formed implants with a controlled degree of hydrogel formation and with retention of some viscous liquid properties, and which remain extrudable, moldable, resistant to irrigation and/or resistant to dissolution (cohesion in solution), and retain their osteoinductive properties, even following extrusion, forming, molding or shaping, and after terminal sterilization and extended storage (for example, sterilization by gamma irradiation followed by storage overnight or longer, or for at least one, two or three months, or up to six months or one year) in a sealed package.

It has been found that heating the collagen source mixture at 120° C. in an autoclave for 60 minutes produced an implantable composition having surprisingly good physical properties suitable for a formed implant, such as handling, irrigation resistance and cohesion in solution. It has also been found that heating a collagen source mixture at about 100° C. for a time between about 90 and 180 minutes produced an implantable composition having surprisingly good physical properties suitable for a formed implant. Various embodiments of these implantable compositions and formed implants are not extrudable and they do not flow, and they form or comprise gels. These embodiments are shapeable, rubbery and/or malleable. Various embodiments of the present formed implants are highly cohesive in water and resistant to irrigation, making them less likely to leave the site of implantation. This allows the resulting formed implants to be irrigated or completely submerged in a saline solution and subsequently handled without loss of physical properties. The high water resistance also ensures that the formed implant is not carried away by body fluids at the surgical site.

Formed implants may encompass shapes such as a ball, rod, capsule, pellet, oval, egg, sphere, sheet, film or membrane. Such formed implants may be extruded, rolled, compressed, stretched, pulled or otherwise manipulated by a machine or simple mechanical device, or created by hand, either intraoperatively or preoperatively and at the surgery site, at the recovery site, or at a discrete processing location or facility.

As an example of a denaturation process for making an implantable composition suitable for use in a formed implant, a collagen source, such as demineralized bone matrix, is exposed to a denaturing solution. The DBM is then heated so that the collagen will be thermally denatured. The heating can be done using an autoclave or other heater as described above. The collagen source can heated be at 120° C. for 60 minutes, or at about 100° C. for a time between about 90 and 180 minutes. After heating, the denatured collagen source mixture is then allowed to cool. If the denaturing solution is acidic or base, the denaturing solution can then be neutralized as described above. The implantable composition can then be dried and/or frozen. The present implantable compositions can be the product of the foregoing denaturation process, or of other methods that yield an implantable composition having the same or similar physical properties. Alternatively or additionally, the implantable composition comprises a mixture of collagen fragments having an SDS-PAGE profile substantially the same as shown in Lane I of any of FIGS. 2A through 2D.

The formed implant or implantable composition can further include an osteoinductive substance, and a liquid medium. Other agents and substances, such as an osteogenic substance or other medically useful substance, can be included.

The following examples further illustrate the present invention but should not be construed as limiting its scope in any way.

EXAMPLE 1

This example demonstrates a novel method of making a carrier for use in an implantable composition, such as an osteoinductive putty. 67 g of DBM was added to 670 mL of a denaturing solution. In this example, the denaturing solution was a very dilute aqueous solution of hydrochloric acid (e.g., 0.05 N). Then the mixture was placed in an autoclave and held at 120° C. for 90 minutes. After autoclaving, the denatured collagen source mixture was allowed to cool for 15 to 30 minutes, and then was mixed by hand using a spoonula. The pH of the mixture was then tested using pH strips and brought to a pH within the range of 4.0 to 6.0 using an appropriate volume of an aqueous NaOH solution (5 N). The mixture was then pipetted into Petri dishes and frozen at −80° C. for at least 30 minutes. The frozen mixture was then lyophilized, and the Petri dishes were covered in parafilm and stored at room temperature until the dry carrier was to be used for preparing an implantable composition.

EXAMPLE 2

This example demonstrates a novel method of making a carrier for use in an implantable composition, such as an osteoinductive putty. 67 g of DBM is added to 670 mL of a denaturing solution. In this example, the denaturing solution is a dilute aqueous solution of sodium hydroxide (e.g. 0.05 N). Then the mixture is placed in an autoclave and held at 120° C. for 90 minutes. After autoclaving, the denatured collagen source mixture is allowed to cool for 15 to 30 minutes, and then is mixed by hand using a spoonula. The pH of the mixture is then tested using pH strips and brought to a pH within the range of 4.0 to 6.0 using an appropriate volume of an aqueous HCl solution (5 N). The mixture is then pipetted into Petri dishes and frozen at −80° C. for at least 30 minutes. The frozen mixture is then lyophilized, and the Petri dishes are covered in parafilm and stored at room temperature until the dry carrier is to be used for preparing an implantable composition.

EXAMPLE 3

This example demonstrates a novel method of making a carrier for use in an implantable composition, such as an osteoinductive putty. 10 g of DBM is added to 100 mL of a denaturing solution. In this example, the denaturing solution is a very dilute aqueous solution of hydrochloric acid (e.g., 0.05 N). Then the mixture is placed on a heater (such as a hot plate) and brought to a boil, between 60 and 100° C. The mixture is boiled for 180 minutes or until the volume of liquid is reduced by 80%. After boiling, the mixture is allowed to cool for 15-30 minutes, then is mixed by hand using a spoonula. The pH of the mixture is then tested using pH strips and brought to a pH within the range of 4.0 to 6.0 using an appropriate volume of an aqueous basic solution, such as 5 N NaOH. The mixture is then pipetted into Petri dishes and frozen at −80° C. for at least 30 minutes. The frozen mixture is then lyophilized, and the Petri dishes are covered in parafilm and stored at room temperature until the dry carrier is to be used for preparing an implantable composition.

EXAMPLE 4

This example demonstrates a novel method of making a carrier for an implantable composition, such as an osteoinductive putty, from a collagen source other than DBM. In this example, the collagen source is a section or entire piece of sterilized human cortical bone that has not been demineralized. The bone is added to a denaturing solution such as 0.05 N HCl. The volume of denaturing solution in mL should be 10 times the bone's weight in grams. The denaturing solution and bone form a collagen source mixture, which is heated using an autoclave as detailed in Examples 1 and 2. Since the bone is mineralized, a higher temperature is used for thermal denaturation, such as a temperature of 140° C. or higher. After heating, the mixture is allowed to cool for 15-30 minutes, then is mixed by hand. The mixture can be subjected to grinding either before or after denaturing to reduce the particle size of any residual bone. The pH of the mixture is then tested and brought to a pH within the range of 4.0 to 6.0 using an appropriate volume of a neutralizing solution, such as an aqueous basic solution (5 N NaOH). The mixture is then pipetted into Petri dishes and frozen at −80° C. for at least 30 minutes. The frozen mixture is then lyophilized, and the Petri dishes are covered in parafilm and stored at room temperature until the dry carrier is to be used for preparing an implantable composition.

EXAMPLE 5

This example demonstrates a novel method of making a xenogenic carrier for an implantable composition, such as an osteoinductive putty. The xenogenic carrier is made from an animal collagen source, such as a porcine, ovine or bovine collagen source. It is contemplated that the high temperatures used for thermal denaturation of the collagen source will also reduce the immunogenicity of the xenogenic carrier. 67 g of bovine, ovine, or porcine demineralized bone matrix (DBM) is added to 670 mL of 0.05 N HCl or another denaturing solution. The mixture is either heated using an autoclave as detailed in Examples 1 and 2 or using other heaters as detailed in Example 3. After heating, the collagen source mixture is allowed to cool for 15-30 minutes, and then is mixed by hand using a spoonula. The pH of the mixture is then tested using pH strips and brought to a pH within the range of 4.0 to 6.0 using an appropriate volume of a neutralizing solution, such as 5 N NaOH. The mixture is then pipetted into Petri dishes and frozen at −80° C. for at least 30 minutes. The frozen mixture is then lyophilized, and the Petri dishes are covered in parafilm and stored at room temperature until the dry carrier is to be used for preparing an implantable composition.

EXAMPLE 6

This example demonstrates a novel method of making a xenogenic carrier for use in an implantable composition, such as an osteoinductive putty, from a collagen source other than DBM. In this example, the collagen source is a section or entire piece of sterilized bovine, ovine, or porcine cortical bone that has not been demineralized. The bone is added to a denaturing solution such as 0.05 N HCl. The volume of denaturing solution in mL should be 10 times the bone's weight in grams. The denaturing solution and bone form a collagen source mixture, which is heated using an autoclave as detailed in Examples 1 and 2. Since the bone is mineralized, a higher temperature is used for thermal denaturation, such as a temperature of 140° C. or higher. After heating, the denatured collagen source mixture is allowed to cool for 15-30 minutes, then is mixed by hand. The pH of the mixture is then tested using pH strips and brought to a pH within the range of 4.0 to 6.0 using an appropriate volume of neutralizing solution, such as 5 N NaOH. The mixture is then pipetted into Petri dishes and frozen at −80° C. for at least 30 minutes. The frozen mixture is then lyophilized, and the Petri dishes are covered in parafilm and stored at room temperature until the dry carrier is to be used for preparing an implantable composition.

EXAMPLE 7

This example demonstrates a novel method of making a carrier for producing an osteoinductive putty. In this example, a soft tissue is used as the collagen source. A human tendon is selected for use as a starting material in this example. The tendon is ground and lyophilized to form a powder. A denaturing solution, such as 0.05 N HCl, is added to the tendon powder such that the volume of denaturing solution in mL is ten times the tendon powder's weight in grams. This collagen source mixture is either heated using an autoclave as detailed in Examples 1-2 or using other heaters as detailed in Example 3. When a soft tissue is used as the collagen source, it is contemplated that lower temperatures, such as about 75° C. or about 100° C. may be suitable. After heating, the mixture is allowed to cool for 15-30 minutes, then is mixed by hand. The pH of the mixture then tested using pH strips and brought to a pH within the range of 4.0 to 6.0 using an appropriate volume of neutralizing solution, such as 5 N NaOH. The mixture is then pipetted into Petri dishes and frozen at −80° C. for at least 30 minutes. The frozen mixture is then lyophilized, and the Petri dishes are covered in parafilm and stored at room temperature until the dry carrier is ready to be used for preparing an implantable composition.

EXAMPLE 8

This example demonstrates a novel method of making an osteoinductive putty. This process begins with a carrier produced according to Examples 1-7. The carrier is ground to a fine powder using a blender. The ground material is then sieved through an 850 micron sieve to remove any residual non-powdered chunks of carrier. Residual pieces of carrier cakes are then re-ground until they pass through the sieve.

To prepare the putty, the dry powdered carrier is first mixed with a suitable amount of an osteoinductive substance (dry DBM). Then a suitable amount of room temperature sterile distilled deionized water (ddH$_2$O) is added to form a putty. If a temperature of 120° C. was used when autoclaving the carrier, a mixture of DBM, carrier, and water is 29% (by weight), 37% (by weight), and 34% (by weight) respectively.

The putty can then be loaded into a syringe for use. The pH of the final putty can be tested by using a flat surface electrode if desired (see, e.g. U.S. Pat. No. 6,679,918). The pH should be about 4.0 to about 6.0.

EXAMPLE 9

A series of putties are made according to the process of Example 8 and having a variety of consistencies. Table 1 shows the amounts (in grams) of carrier, osteoinductive substance, and water (in mL) combined to make the putties.

TABLE 1

Formulations for Osteoinductive Putties

| Sample | (grams) Carrier | (grams) DBM | Total Powder (g) | Water (mL) | Total (g) | (% by weight) % DBM | (% by weight) % carrier | (% by weight) % water | yield cc |
|---|---|---|---|---|---|---|---|---|---|
| 9A | 0.35 | 0.27 | 0.62 | 0.7 | 1.32 | 20 | 27 | 53 | 1.00 |
| 9B | 1.75 | 1.35 | 3.10 | 3.5 | 6.60 | 20 | 27 | 53 | 5.00 |
| 9C | 3.5 | 2.7 | 6.20 | 7 | 13.20 | 20 | 27 | 53 | 10.00 |
| 9D | 0.35 | 0.27 | 0.62 | 0.6 | 1.22 | 22 | 29 | 49 | 0.92 |
| 9E | 1.75 | 1.35 | 3.10 | 3 | 6.10 | 22 | 29 | 29 | 4.62 |
| 9F | 3.5 | 2.7 | 6.20 | 6 | 12.20 | 22 | 29 | 49 | 9.24 |
| 9G | 0.35 | 0.27 | 0.62 | 0.5 | 1.12 | 24 | 31 | 45 | 0.85 |
| 9H | 1.75 | 1.35 | 3.10 | 2.5 | 5.60 | 24 | 31 | 45 | 4.24 |
| 9I | 3.5 | 2.7 | 6.20 | 5 | 11.20 | 24 | 31 | 45 | 8.48 |
| 9J | 0.35 | 0.27 | 0.62 | 0.4 | 1.02 | 26 | 34 | 39 | 0.77 |
| 9K | 1.75 | 1.35 | 3.10 | 2 | 5.10 | 26 | 34 | 39 | 3.86 |
| 9L | 3.5 | 2.7 | 6.20 | 4 | 10.20 | 26 | 34 | 39 | 7.73 |
| 9M | 0.35 | 0.27 | 0.62 | 0.35 | 0.97 | 28 | 36 | 36 | 0.73 |
| 9N | 1.75 | 1.35 | 3.10 | 1.75 | 4.85 | 28 | 36 | 36 | 3.67 |
| 9O | 3.5 | 2.7 | 6.20 | 3.5 | 9.70 | 28 | 36 | 36 | 7.35 |
| 9P | 0.35 | 0.27 | 0.62 | 0.3 | 0.92 | 29 | 38 | 33 | 0.70 |
| 9Q | 1.75 | 1.35 | 3.10 | 1.5 | 4.60 | 29 | 38 | 33 | 3.48 |
| 9R | 3.5 | 2.7 | 6.20 | 3 | 9.20 | 29 | 38 | 33 | 6.97 |

EXAMPLE 10

In this example, the extrudability of an embodiment of the present osteoinductive putty is compared to a putty comprising porcine gelatin as a carrier. An embodiment of the present osteoinductive putty was prepared according to Example 8. Another composition was prepared by combining 4.23 g of DBM, 2.67 g of porcine gelatin, and 14 mL water. Both samples were extruded through a Beckton Dickinson 5 mL slip tip syringe reference number 301603. Although the porcine gelatin composition was extrudable if used as recommended, such as within 20 minutes, it was not extrudable following wet storage for a longer period of time. When the porcine gelatin based composition was left overnight, it was not extrudable through the syringe.

EXAMPLE 11

This example demonstrates a novel method of making osteoinductive putties. A carrier produced according to one of Examples 1-7 is provided. The carrier is ground to a fine powder using a blender. The ground material is then sieved through an 850 micron sieve to remove any residual non-powdered chunks of carrier. Residual pieces of carrier cakes are then re-ground until they pass through the sieve without being forced.

To prepare the putty, the powdered dry carrier is first mixed with a suitable amount of dry DBM. Then a suitable amount of sterile distilled deionized water (ddH$_2$O) at 90° C. is added to form a putty. If a temperature of 120° C. was used when autoclaving the carrier, a mixture comprises 29% (by weight) DBM, 37% (by weight) carrier, and 34% (by weight) water.

The putty can then be loaded into a syringe for use. The pH of the final putty can be tested, such as by using a flat surface electrode. The pH can be between about 4.0 and about 6.0.

EXAMPLE 12

This example demonstrates a novel method of making an osteoinductive putty. A carrier produced according to one of Examples 1-7 is provided. The carrier is ground to a fine powder using a blender. The ground material is then sieved through an 850 micron sieve to remove any residual non-powdered chunks of carrier. Residual pieces of carrier cakes are then re-ground until they pass through the sieve.

To prepare the putty, the dry powdered carrier is first mixed with a suitable amount of whole bone. Then a suitable amount of room temperature sterile distilled deionized water (ddH$_2$O) is added to form a putty. If a temperature of 120° C. was used when autoclaving the carrier, a mixture of whole bone, carrier, and water is 29% (by weight), 37% (by weight), and 34% (by weight) respectively.

The putty can then be loaded into a syringe for use. The pH of the final putty can be tested, such as by using a flat surface electrode. The pH can be between about 4.0 and about 6.0.

EXAMPLE 13

This example demonstrates a novel method of making an osteoinductive putty. This process begins with the carrier produced according to Examples 1-7. The carrier is ground to a fine powder using a blender. The ground material is then sieved through an 850 micron sieve to remove any residual non-powdered chunks of carrier. Residual pieces of carrier cakes are then re-ground until they pass through the sieve.

To prepare the putty, the dry powdered carrier is first mixed with a suitable amount of a combination of BMPs and growth factors. Then a suitable amount of room temperature sterile distilled deionized water (ddH$_2$O) is added to form a putty. If a temperature of 120° C. was used when autoclaving the carrier, a mixture of the combined BMPs and growth factors, the carrier, and water is 29% (by weight), 37% (by weight), and 34% (by weight) respectively.

The putty can then be loaded into a syringe for use. The pH of the final putty can be tested, such as by using a flat surface electrode. The pH can be between about 4.0 and 6.0.

EXAMPLE 14

Figure 1B:
Figure 1C:
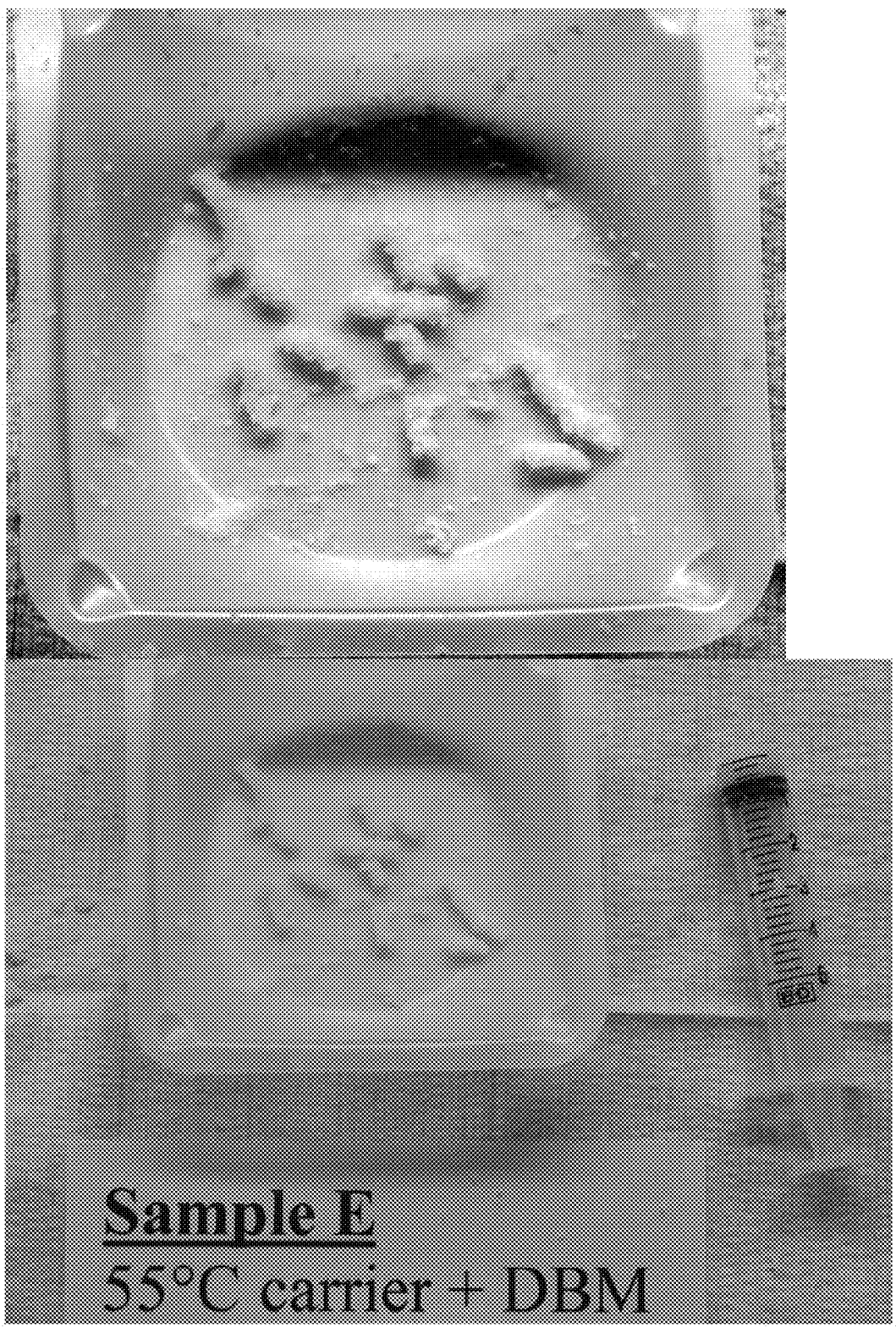
Figure 1D:
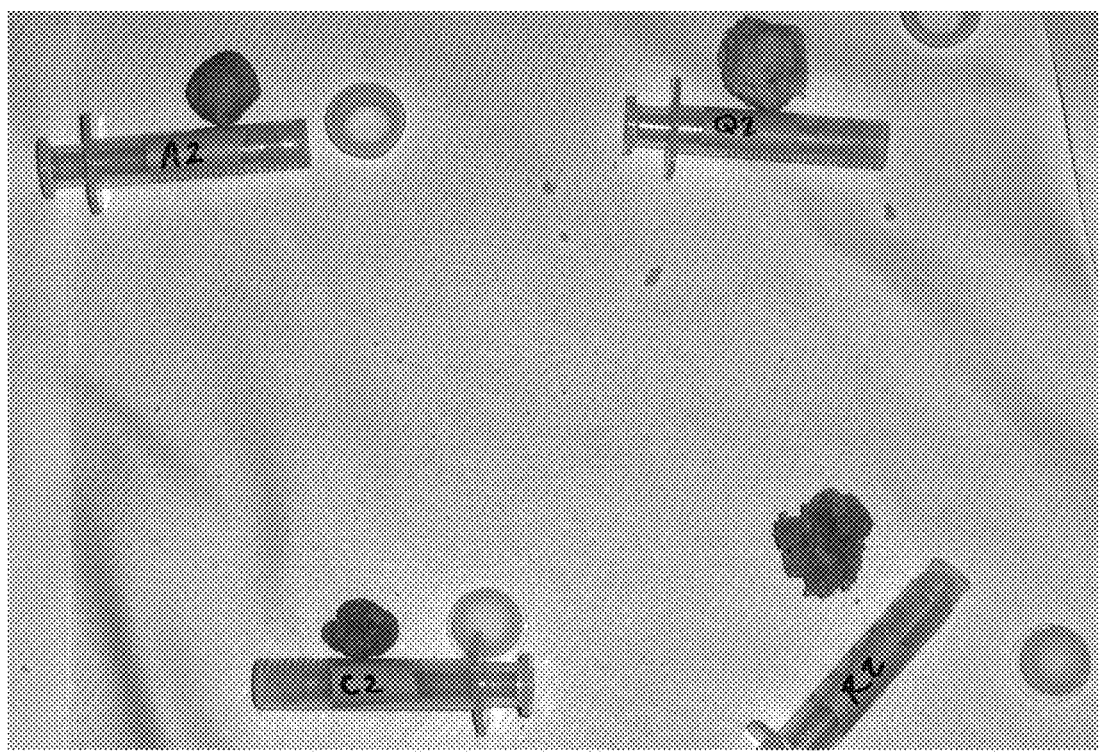
FIGS. 1D and 1E are photographs of putties that have been extruded from a syringe having a wide tip, and molded by hand into a rough sphere. The different putties comprise carriers prepared from demineralized bone matrix at different processing temperatures and different processing times.
Figure 1E:
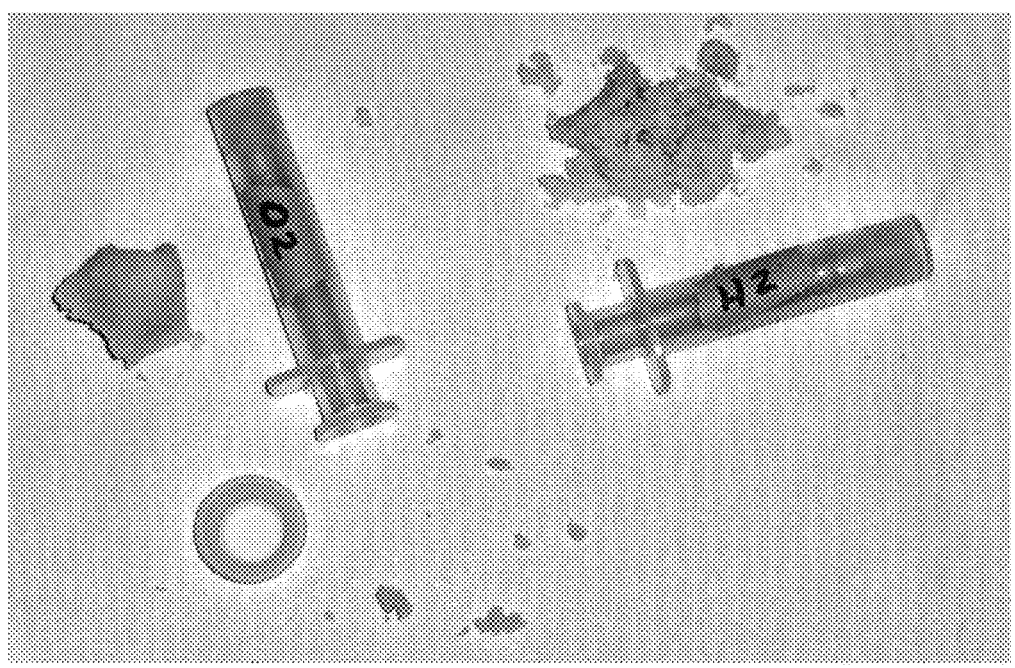
Figure 1F:
FIG. 1F is a photograph of a putty made from demineralized bone matrix heated to 120° C. temperature for 90 minutes, mixed with active demineralized bone matrix and water, then extruded and molded by hand into a ball shape.
Figure 1G:
FIG. 1G is a photograph of a putty made from demineralized bone matrix heated to 120° C. for 90 minutes, mixed with active demineralized bone matrix and water, then extruded and placed on a glass slide to be tested for irrigation resistance.
Figure 1H:
FIG. 1H is a photograph of a putty made from demineralized bone matrix heated to 120° C. for 75 minutes, mixed with active demineralized bone matrix and water, then extruded and molded by hand into a ball shape.
Figure 1I:
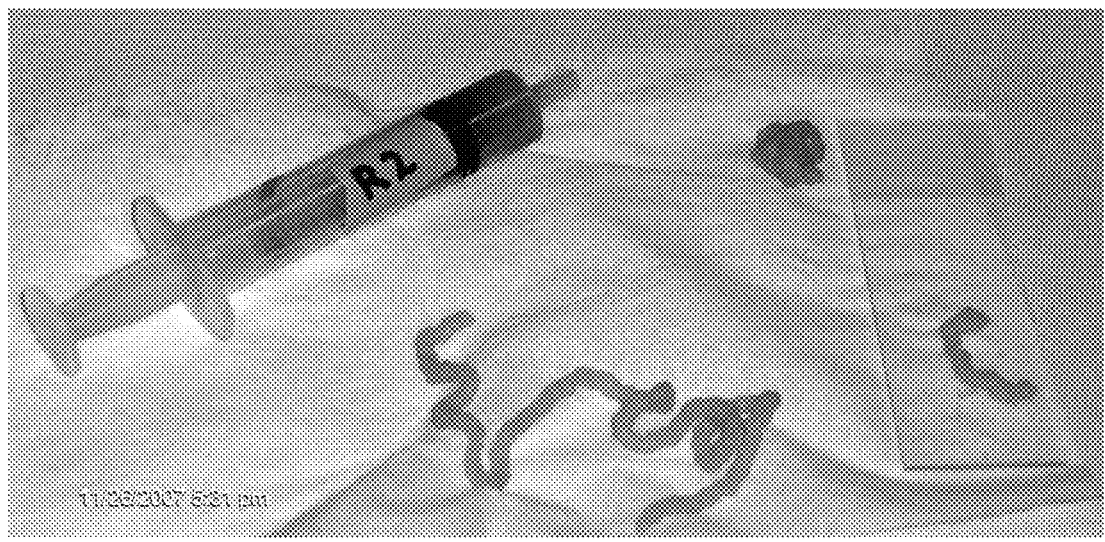
FIG. 1I is a photograph of a putty made from demineralized bone matrix heated to 120° C. for 75 minutes, mixed with active demineralized bone matrix and water, then extruded and placed on a glass slide to be tested for irrigation resistance.
Figure 1J:
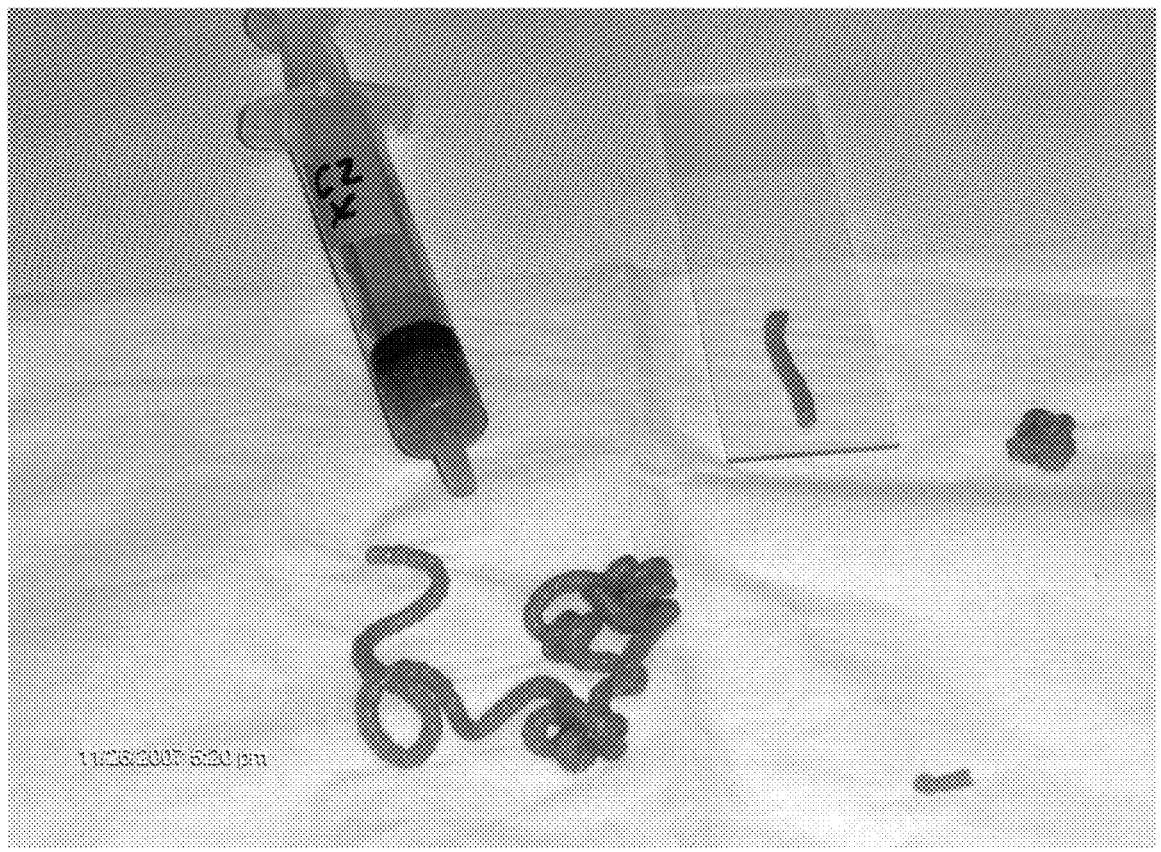
FIG. 1J is a photograph of a putty made from demineralized bone matrix heated to 120° C. for 90 minutes, mixed with active demineralized bone matrix and water, then extruded and molded by hand into ball shape, as well as placed on a glass slide to be tested for irrigation resistance.
Figure 1K:
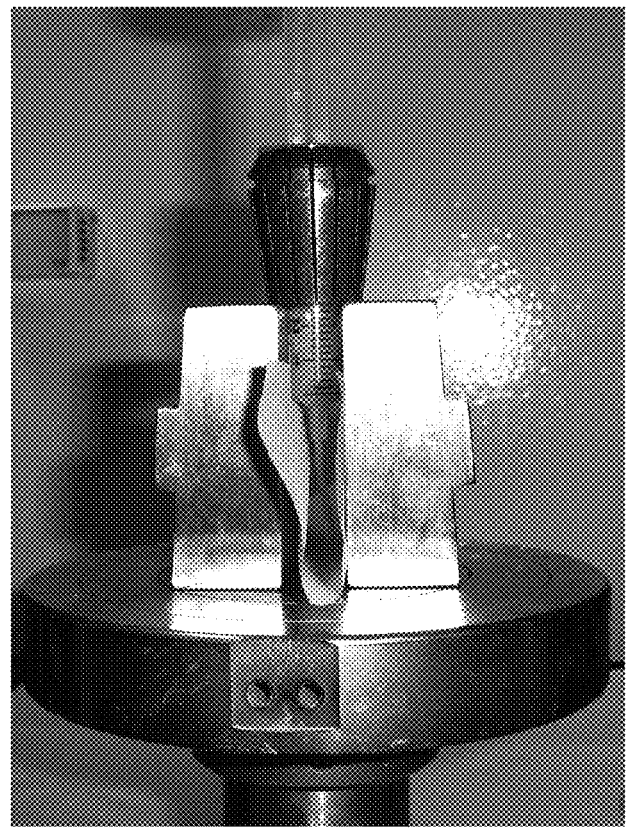
FIG. 1K is a photograph of a syringe loaded with putty that has been set up for an extrusion test in the Instron force testing machine.
Figure 1L:
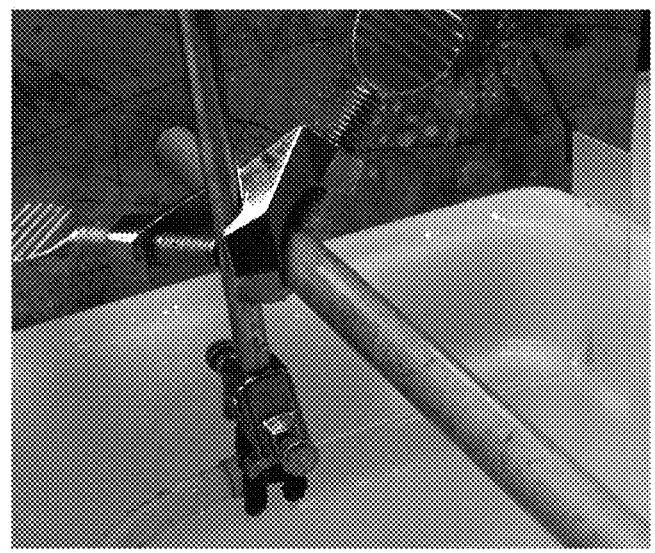
FIG. 1L is a photograph of the apparatus used to test extruded putty for irrigation resistance, wherein a lavage pump is set to impinge upon a microscope slide, directly adjacent to the adhering putty sample.
Figure 1M:
FIG. 1M is a photograph of the front view of the water bath and apparatus used to test extruded putty for cohesion in solution (dissolution).
Figure 1N:
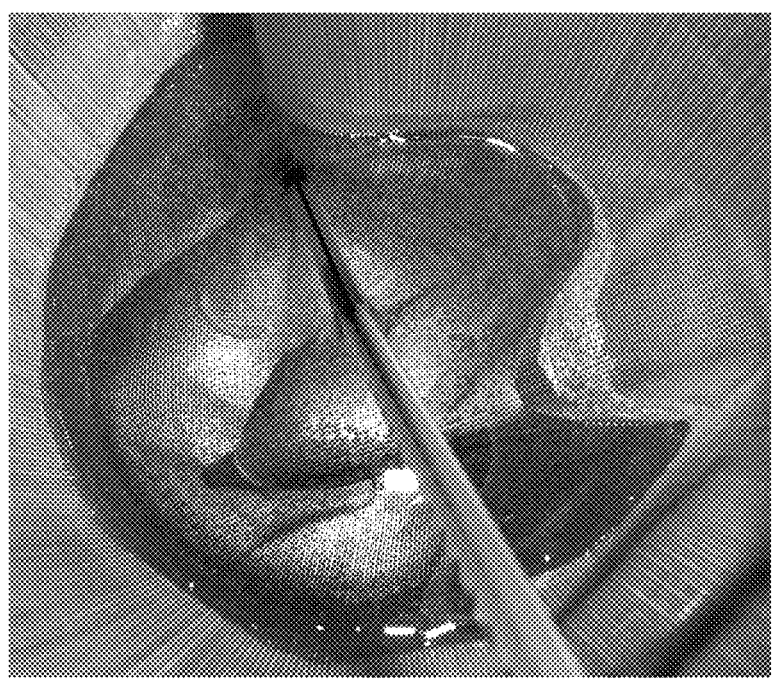
FIG. 1N is a photograph of the top view of the water bath and apparatus used to test extruded putty for cohesion in solution.
Figure 1O:
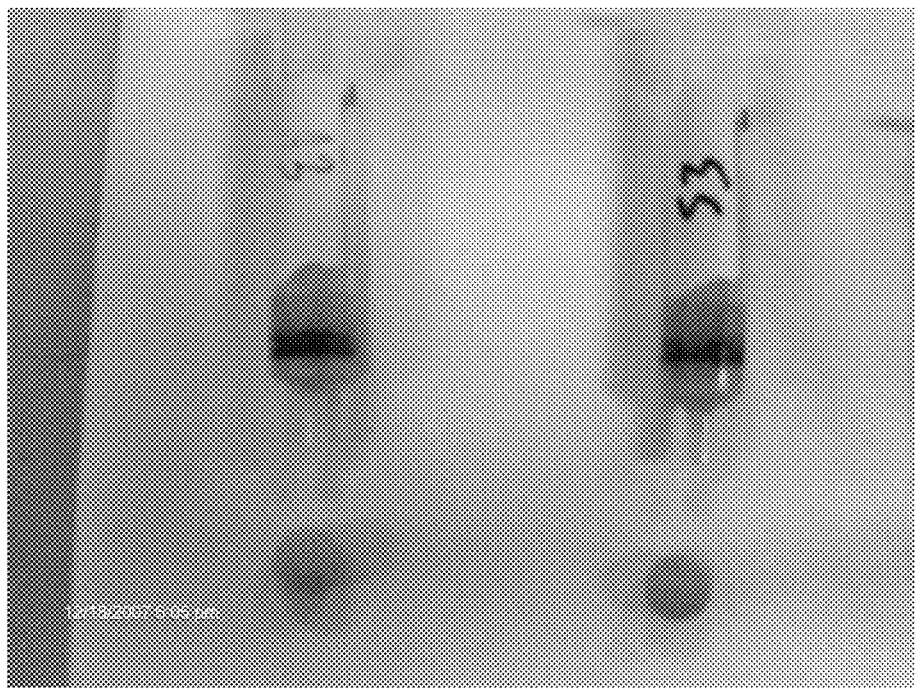
FIG. 1O is a photograph of one putty made from demineralized bone matrix heated to 120° C. for 90 minutes, mixed with active DBM and water, then extruded and molded by hand into ball shape (labeled A3 in the photograph), and another putty made from demineralized bone matrix heated to 135° C. for 90 minutes, mixed with active DBM and water, then extruded and molded by hand into ball shape (labeled S3 in the photograph).
Figure 1P:
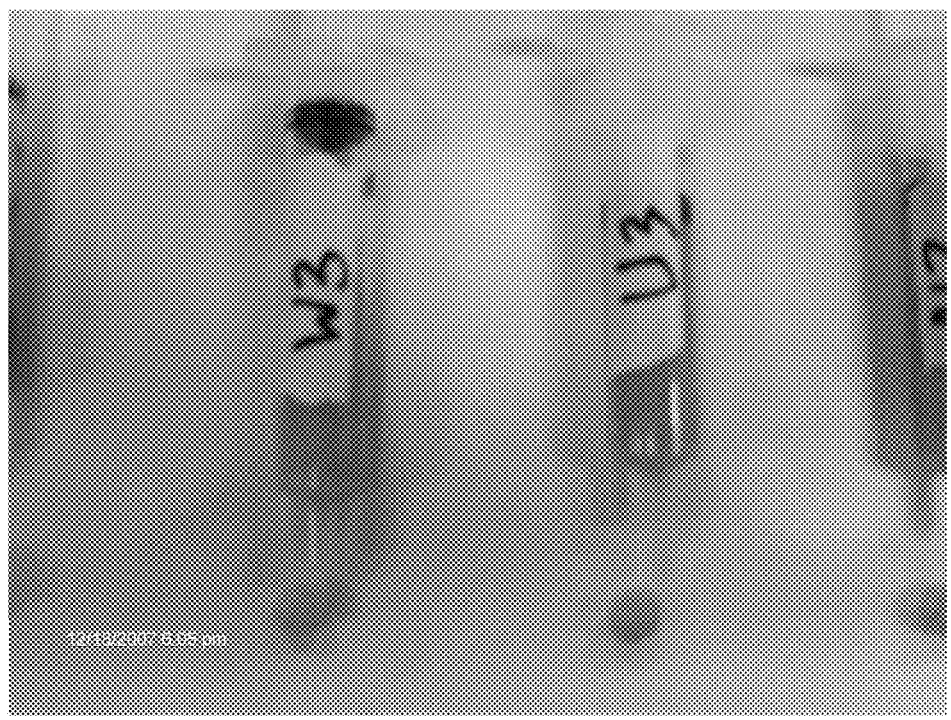
FIG. 1P is a photograph of one putty made from demineralized bone matrix heated to 118° C. for 90 minutes, mixed with active DBM and water, then extruded and molded by hand into ball shape (labeled W3 in the photograph), and another putty made from demineralized bone matrix heated to 120° C. for 180 minutes, mixed with active DBM and water, then extruded and molded by hand into ball shape (labeled U3 in the photograph).
Figure 1Q:
FIG. 1Q is a photograph of one putty made from demineralized bone matrix heated to 118° C. for 90 minutes, mixed with active DBM and water (containing 50% more water than the putty shown in FIG. 1P), then extruded and molded by hand into a ball shape (labeled W3X in the photograph), a second putty made from demineralized bone matrix heated to 135° C. for 75 minutes, mixed with active DBM and water, then extruded and molded by hand into ball shape (labeled T3 in the photograph), and a third putty made from demineralized bone matrix heated to 115° C. for 90 minutes, mixed with active DBM and water (containing 50% more water than the putty shown in FIG. 1R), then extruded and molded by hand into ball shape (labeled V3X in the photograph).
Figure 1R:
FIG. 1R is a photograph of one putty made from demineralized bone matrix heated to 115° C. for 90 minutes, mixed with active DBM and water, then extruded and molded by hand into ball shape (labeled V3 in the photograph), and another putty made from demineralized bone matrix heated to 100° C. for 90 minutes, mixed with active DBM and water, then loaded in a syringe, which failed to extrude from the syringe (labeled I3 in the photograph).
Figure 1S:
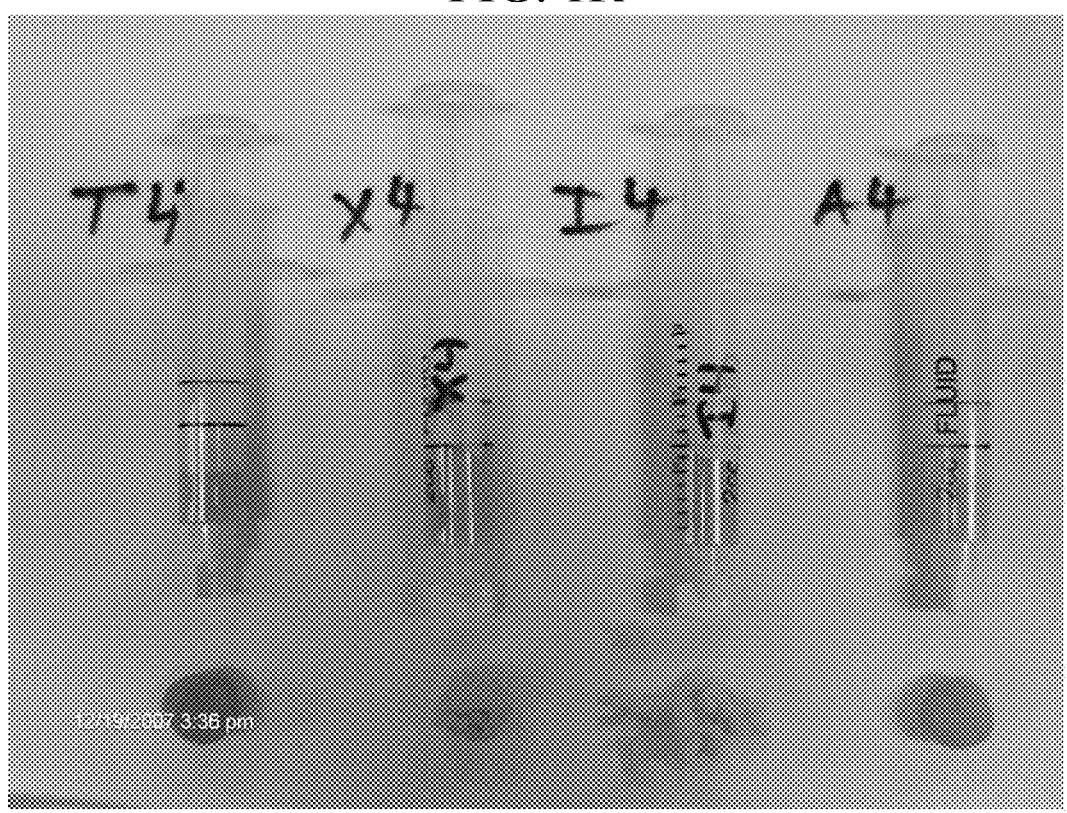
FIG. 1S is a photograph of four putties, each processed for 90 minutes at a different temperature, and each mixed with a higher concentration of water (about 32% more water than the putties shown in previous Figures). The first is a putty made from demineralized bone matrix heated to 100° C. for 90 minutes, mixed with active DBM and water, then extruded and molded by hand into ball shape (labeled I4 in the photograph). The second is a putty made from demineralized bone matrix heated to 110° C. for 90 minutes, mixed with active DBM and water, then extruded and molded by hand into ball shape (labeled X4 in the photograph). The third is a putty made from demineralized bone matrix heated to 120° C. for 90 minutes, mixed with active DBM and water, then extruded and molded by hand into ball shape (labeled A4 in the photograph). The fourth is a putty made from demineralized bone matrix heated to 135° C. for 90 minutes, mixed with active DBM and water, then extruded and molded by hand into ball shape (labeled T4 in the photograph). It was noted following completion of testing that the sample labeled as T4 in FIG. 1S was actually labeled and tested as S4 in Examples 17, 18, and 19.

FIGS. 1A through 1C are photographs of putties that have been extruded from a syringe. The different putties comprise carriers prepared from demineralized bone matrix at different temperatures. Each of the putties was made with 5.18 g of carrier, 4.0 g of DBM, and 4.71 mL of sterilized distilled deionized water, resulting in a putty that was about 37% carrier, about 29% DBM, and about 34% water. FIG. 1A shows a putty containing a carrier made by heating a collagen source mixture comprising a 1:10 (g:mL) ratio of DBM and 0.05 N HCl in an autoclave at a temperature of 120° C. for 90 minutes. The putty comprised 5.18 g carrier, 4.0 g DBM and 4.71 mL ddH2O. This putty exhibited excellent extrudability from the syringe, and it retained good moldability and cohesiveness after extrusion. FIG. 1B shows a putty containing a carrier made by heating a collagen source mixture comprising a 1:10 ratio of DBM and 0.05 N HCl in an autoclave at a temperature of 100° C. for 90 minutes. The putty comprised 5.18 g carrier, 4.0 g DBM and 4.71 mL ddH2O. This putty was crumbly and had poor consistency and cohesiveness, and it did not extrude easily. FIG. 1C shows a putty containing a carrier made by heating a collagen source mixture comprising a 1:10 ratio of DBM and 0.05 N HCl in an autoclave at a temperature of 55° C. for 90 minutes. This putty was also crumbly and had poor consistency and cohesiveness, and it did not extrude easily. For this example, Beckton Dickinson 5 mL slip tip syringes reference number 301603 were modified by cutting off the nozzle, leaving a wider opening at the end opposite the plunger. The syringes were modified in this manner because the putty shown in FIGS. 1B and 1C could not be extruded through the normal syringe.

EXAMPLE 15

In this example, a variety of samples were analyzed to determine whether there were differences between the present carriers and other materials, such as gelatins and collagen sources processed under different procedures. The present example shows differences in the molecular weight distributions and SDS-PAGE profiles of the collagen fragments in the present carriers compared to other materials. In this example, Sample A was a putty made from 5.18 g of carrier, 4.0 g of active DBM, and 4.71 mL of water. The carrier was made by mixing a 1:10 (g:mL) ratio of DBM and 0.05 N HCl, and heating the mixture at 120° C. in an autoclave for 90 minutes. Sample B was a putty made from 5.18 g of carrier, 4.0 g of active DBM, and 4.71 mL of water. The carrier was made by mixing a 1:10 ratio of DBM and 0.05 N HCl, and heating the mixture at 55° C. in an autoclave for 90 minutes. Sample C was a wet carrier made from 9.18 g of carrier and 4.71 mL of water. The carrier was made by mixing a 1:10 ratio of DBM and 0.05 N HCl, and heating the mixture at 120° C. in an autoclave for 90 minutes. Sample D was a wet carrier made from 9.18 g of carrier and 4.71 mL of water. The carrier was made by mixing a 1:10 ratio (g:mL) of DBM and 0.05 N HCl, and heating the mixture at 55° C. in an autoclave for 90 minutes. Sample E was a putty made from 2.67 g of carrier, 4.23 g of active DBM, and 14 mL of water. The carrier was a commercially available fine porcine gelatin carrier. Sample F was a putty made from 2.67 g of carrier, 4.23 g of active DBM, and 14 mL of water. The carrier was a commercially available coarse porcine gelatin carrier. Sample G was a wet carrier made from 6.9 g of carrier and 14 mL of water. The carrier was a commercially available fine porcine gelatin carrier. Sample H was a putty made from 5.18 g of carrier, 4.0 g of active DBM, and 4.71 mL of water. The carrier was made by mixing a 1:10 ratio of DBM and 0.05 N HCl, and heating the mixture at 100° C. in an autoclave for 90 minutes. Sample I was a wet carrier made from 9.18 g of carrier and 4.71 mL of water. The carrier was made by mixing a 1:10 ratio of DBM and 0.05 N HCl, and heating the mixture at 100° C. in an autoclave for 90 minutes.

The molecular weight distribution of any of the foregoing carriers is analyzed by SDS-PAGE (Western Blot). FIGS. 2A through 2H set forth SDS-PAGE profiles (shown by Western blot analyses) of the products resulting from various treatments of collagen sources. The experiments were carried out as follows: One mL of 0.1N acetic acid was added to 1.5 mL Eppendorf tubes that contain approximately 50 mg of sample. The liquid in tubes was first mixed using 1 mL pipette and then mixed vigorously for 30 seconds using a vortexer (concentration was approximately 50 mg/mL including insoluble material). One hundred microliters (or approximately 1/10 amount for sample that was solid) of the sample in the tube was transferred to a new Eppendorf tube and an additional 900 microliter of 0.1N acetic acid was added (approximately 5 mg/mL including insoluble material). Tubes were then vortexed again for 30 seconds. Two hundred microliters of solution (contains insoluble pellet) were transferred to a new 1.5 mL Eppendorf tube and 100 microliters of three times (3×) concentrated SDS-PAGE sample buffer (final concentration was 1× after mixing with two volume of the sample) without 2-mercaptoethanol (2-ME). Concentration of sample was approximately 3.34 mg/mL, however, the amount of insoluble material at the end was not determined. All samples had some amount of precipitate at the end. Tubes were vortexed for 30 seconds and boiled for 3 min in water bath. Tubes were then microcentrifuged at 12,000 rpm for 1 min to remove large aggregate. Supernatant was used for SDS-PAGE. Gels were 12 lanes 8-16% gradient pre-made gels for Mini protean II gel electrophoresis set from Bio-rad.

Type I collagen (1 mg/mL) from Rockland Immunochemicals, Inc. was used as a control. This was in 0.1N acetic acid and no precipitate was seen in the tube. Two hundred microliter of the Type I collagen was mixed with 100 microliter of 3× sample buffer like other samples. Thus, final concentration of the control Type I collagen was 0.67 mg/mL.

20 microliter of each sample was loaded onto wells of SDS-PAGE. Amount of control Type I collagen in the lane (20 microliter) is 13.4 microgram (0.67 microgram/microliter×20). Amount of other samples in each lane is 68 microgram (0.34 microgram/microliter×20 microliter), however, actual amount of proteins is not known since all samples had insoluble material at the end of preparation of samples for SDS-PAGE.

SDS-PAGE was performed at constant voltage (100 V) for 2.5 h using Bio-rad Mini Protean II electrophoresis set. Proteins in the gels were transferred to nitrocellulose filter using a standard semi-dry protein transfer system (Bio-rad) for 45 min at constant voltage (15 V). After transfer, nitrocellulose filter was stained with 0.1% ponceau red to confirm protein transfer and mark the position of molecular weight markers.

Western blotting Nitrocellulose filters were blocked in 0.5% bovine serum albumin (BSA) in NET/NP40 (150 mM NaCl, 2 mM EDTA, 50 mM Tris-HCl pH 7.5, 0.3% NP40) for 30 min at 22° C. Filters were then incubated with rabbit anti-Type I collagen antibodies (Rockland Immunochemicals, Inc, 1:4,000 dilution, total volume 40 mL of 0.5% BSA NET/NP40) for 45 min at 22° C. in a plastic box on a shaker. Filters were washed three times using ~40 mL of NET/NP40, 5 min each on a shaker. Filters were then incubated with horse-radish peroxidase-conjugated goat anti-rabbit IgG antibodies (Southern Biotechnology, 1:7,000 dilution, total volume of 40 mL in 0.5% BSA NET/NP40) for 45 min at 22° C. in a plastic box on a shaker. Filters were washed three times using ~40 mL of NET/NP40, 5 min each on a shaker, then washed twice using ~40 mL of phosphate buffered saline. Filters were then placed on a clean sheet of plastic wrap after removing extra liquid using paper towel. Four mL/filter of developer (Pierce, Supersignal Westpico) was overlayed on a filter and incubated for 5 min in a dark. Filters were placed between clear folder after removing extra liquid. Images were obtained by exposing x-ray films (Kodak, BioMax MR) to nitrocellulose filters in a clear folder for 10 seconds to 4 min. FIGS. 2A through 2H show films at various exposure times. Films were developed after exposure. X-ray films were scanned and data were organized using Photoshop 7.0 and Canvas 9.01 software. No adjustment of contrast, brightness, or other parameters was performed for the figures.

Samples C, D, F and I were selected for further analysis. The characteristic of sample C was quite different from other samples when 0.1N acetic acid was added to dried powder in the tubes. When 1 mL of 0.1N acetic acid was added to ~50 mg of dried powder, sample C was highly soluble with very small amount (approximately 5% in volume) of precipitates. Sample D was mostly insoluble with ~80% volume of insoluble precipitates. Sample F appeared to absorb liquid and formed a solid gel. Sample I was soluble but formed very thick liquid. After the initial ponceau red staining, sample C was diluted 1:5, sample D was used as it was, and samples F and I were diluted 1:10 to normalize the amount of proteins per lane. Based on this the amount of protein is as follows: C,14 microgram; D, 68 microgram; F and I, 7 microgram. These values are approximate.

As can be seen from these results, the main differences of Type I collagen (I-C) in sample C compared with others when analyzed by SDS-PAGE and Western blotting appeared to be 1) lack of distinct bands, 2) predominance of low molecular weight (smaller than 200 kD) I-C, and 3) presence of very low molecular weight (smaller than 20 kD and 25 kD) I-C. The I-C in sample C shows diffuse distribution without forming distinct bands like all other samples. There are some differences in size and distribution of bands between samples, however, all samples except sample C has 20-30 distinct bands whereas sample C shows diffusely distributed I-C. Also, it appears that more than 90% of I-C in sample C is smaller than 200 kD, in striking contrast to other samples. Lastly, presence of very low molecular weight (smaller than 20 kD and 25 kD) I-C is seen almost exclusively in sample C.

As discussed above, the phrase "does not have a banded region," is intended to include the case where the present carriers may be measured against or compared to certain properties of known materials such as porcine gelatin, Type-I collagen, unprocessed collagen, or collagen processed at a different time and/or temperature than that of the present carriers. For example, it may be observed that the SDS-PAGE profile for Sample C includes a region which exhibits a substantially reduced prominence of discrete, discernable, well defined, sharp, intense, narrow, or noticeable bands, banding or banded regions when compared to the other samples. In contrast to the other samples, the present carriers exhibit a relatively diffuse, smoother and broader region (without prominent, intense, or discernable bands in that region) of their SDS-PAGE profiles. Such a profile is intended to be encompassed by the phrase "does not have a banded region".

Figure 2A:
FIGS. 2A through 2H set forth SDS-PAGE profiles (shown by Western blot analyses) of several putties and carriers. Some of the carriers were gelatins while other carriers were putties made from DBM at different temperatures.
Figure 2B:
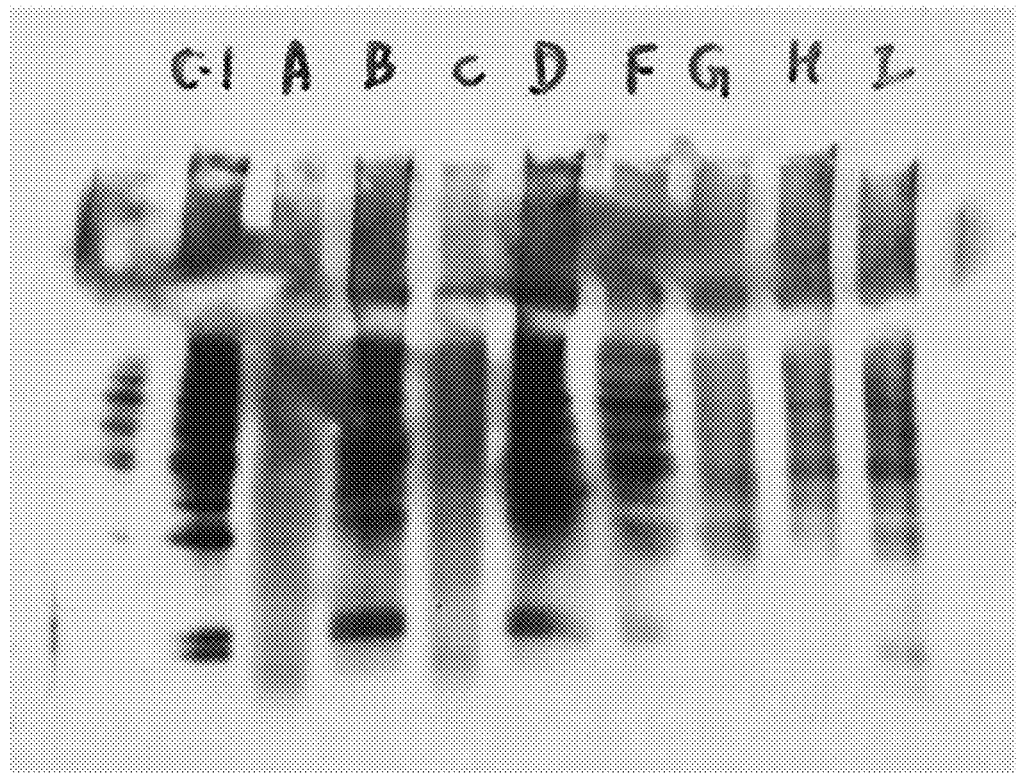
Figure 2C:
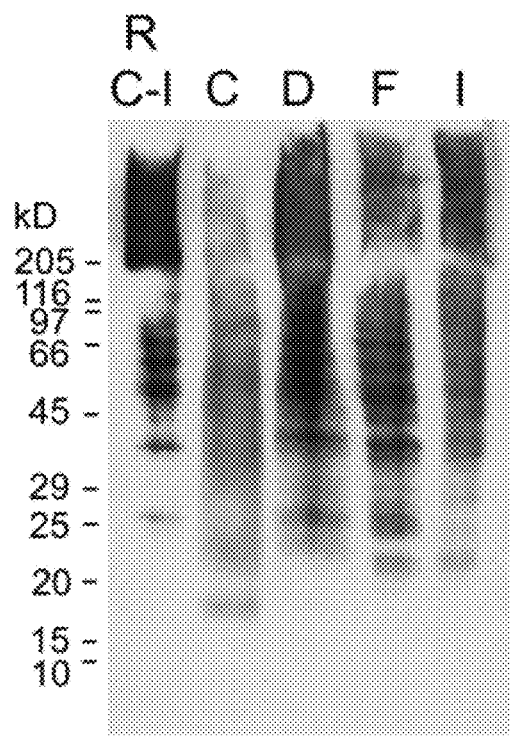
Figure 2D:
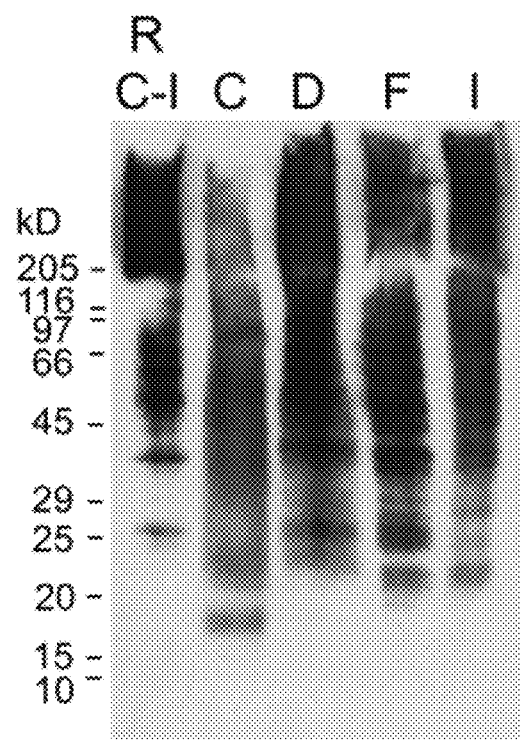
Figure 2E:
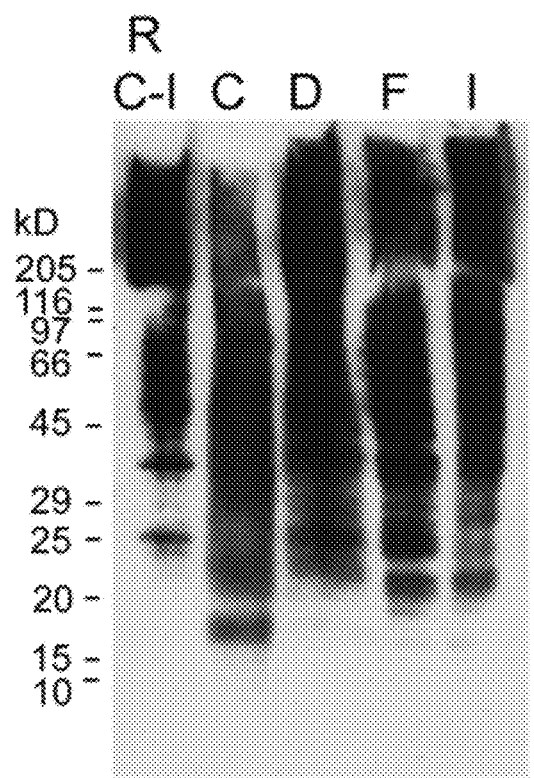
Figure 2F:
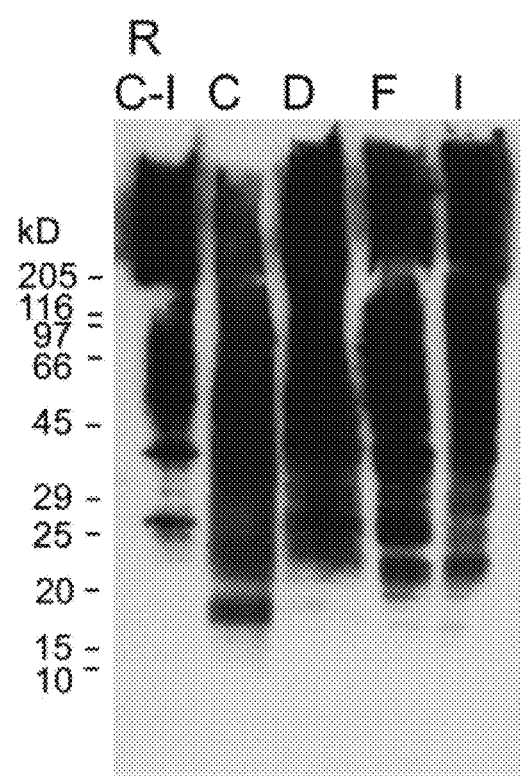
Figure 2G:
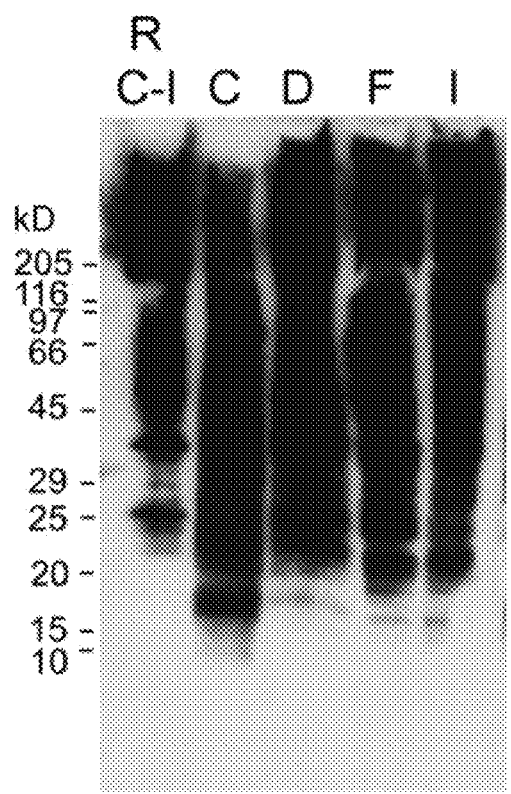
Figure 2H:
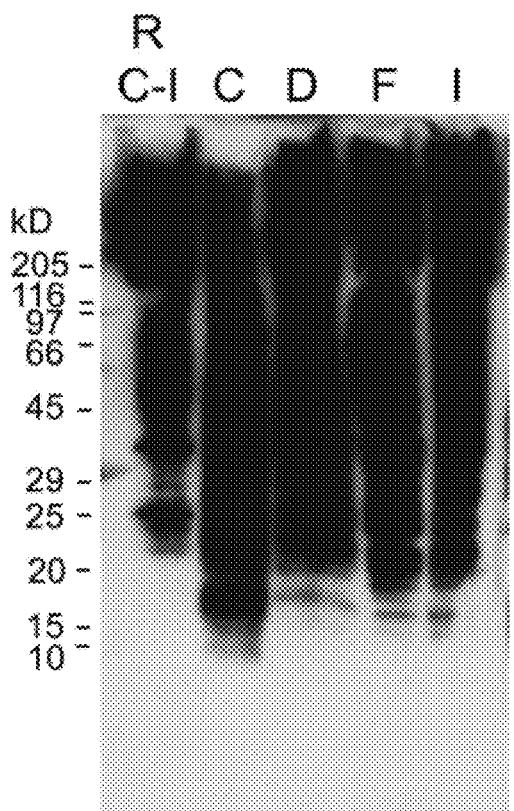

FIG. 2A shows the Western blot without 2-mercaptoethanol as a reducing agent. FIG. 2B shows the Western blot of the same samples with 2-mercaptoethanol as a reducing agent. FIG. 2C shows the Western blot from an exposure time of 10 seconds. FIG. 2D shows the Western blot from an exposure time of 20 seconds. FIG. 2E shows the Western blot from an exposure time of 30 seconds. FIG. 2F shows the Western blot from an exposure time of one minute. FIG. 2G shows the Western blot from an exposure time of two minutes. FIG. 2H shows the Western blot from an exposure time of four minutes.

FIGS. 2A through 2D show that the carrier of Sample C had a substantially uniform molecular weight distribution within the range of from about 45 kDa to about 66 kDa and within other ranges, including from about 29 kDa to about 97 kDa, from about 29 kDa to about 66 kDa, from about 45 kDa to about 97 kDa. Sample C also has a sodium dodecyl sulfate polyacrylamide gel electrophoresis (SDS-PAGE) profile, and its SDS-PAGE profile did not have a banded region between about 45 kDa and about 66 kDa, or a banded region between about 29 kDa and about 97 kDa. The SDS-PAGE profile of Sample C did include a discrete band between about 15 kDa and about 20 kDa, whereas the SDS-PAGE profiles of the other samples did not include a discrete band in that region.

As discussed above, the phrase "does not have a banded region," is intended to include the case where the present carriers may be measured against or compared to certain properties of known materials such as porcine gelatin, Type-I collagen, unprocessed collagen, or collagen processed at a different time and/or temperature than that of the present carriers. For example, it may be observed that the SDS-PAGE profile for Sample C displays a relatively diffuse and smoother region between 29 kDa and 97 kDa or between 45 kDa and 66 kDa when compared to the other samples. As another example, it may be observed that the SDS-PAGE profile for Sample C has a relatively prominent discrete band at a location between 15 kDa and 20 kDa, as compared to the other samples.

EXAMPLE 16

In this example, a variety of samples were analyzed to determine whether there were differences between the present carriers and other materials, such as gelatins and collagen sources processed under different procedures. The present example shows differences in the HPLC chromatograms of the collagen fragments in the present carriers compared to other materials. The test was carried out as follows: 1 mg of collagen was suspended in 1 mL Tris-HCl buffer (0.1 mol/L, pH 7.8, containing 0.1 mol/L NaCl) and denatured at 60° C. for 3 hours. 500 uL of this sample was added to a new tube then 100 uL of a freshly made 0.1 mg/mL tyrosine solution was added. The samples were then heated at 37° C. for an additional 4 hours. The samples were then filtered using a polytetraflorsethylene (PTFE) syringeless filter and injected for High Performance Liquid Chromatography (HPLC) analysis. HPLC was run using an Agilent 1100 series binary pump, a Phenomenex Synergi 4u Hydro-RP 80A (2×150 mm; 4 um; S/N=106273-5) plus C18 guard column (2 mm×4 mm), a manual Rheodyne 7125, 25 uL injection loop, and an Agilent 1100 G1314A UV/Vis detector. The mobile phase A component is 0.2% Acetic acid in H2O. The mobile phase B component is 0.2% Acetic acid in acetonitrile/The gradient at 0.15 mL/min is A:B(min)=100:0(0-5)=>5:95(50-65)=>100:0(75-95). The injection volume is 20 mL. The wavelength is 220 nm.

FIGS. 3A through 3F set forth HPLC analyses of the products resulting from various treatments of collagen sources. Sample 3A was a wet carrier made from 6.9 g of commercially available food quality Knox gelatin and 14 mL of water. Sample 3B was a wet carrier made from 6.9 g of carrier and 14 mL of water. The carrier was a commercially available fine porcine gelatin carrier. Sample 3C was a putty made from 5.18 g of carrier, 4.0 g of active DBM, and 4.71 mL of water. The carrier was made by mixing carrier DBM and 0.05 N HCl in a 1:10 ratio (g:mL), and heating the mixture at 55° C. in an autoclave for 90 minutes. Sample 3D was a wet carrier made from 6.9 g of carrier and 14 mL of water. The carrier was a commercially available course porcine gelatin carrier. Sample 3E was a putty made from 5.18 g of carrier, 4.0 g of active DBM, and 4.71 mL of water. The carrier was made by mixing carrier DBM and 0.05 N HCl in a 1:10 ratio (g:mL), and heating the mixture at 120° C. in an autoclave for 90 minutes. Sample 3F was a putty made from 5.18 g of carrier, 4.0 g of active DBM, and 4.71 mL of water. The carrier was made by mixing carrier DBM and 0.05 N HCl in a 1:10 ratio (g:mL), and heating the mixture at 100° C. in an autoclave for 90 minutes.

Figure 3A:
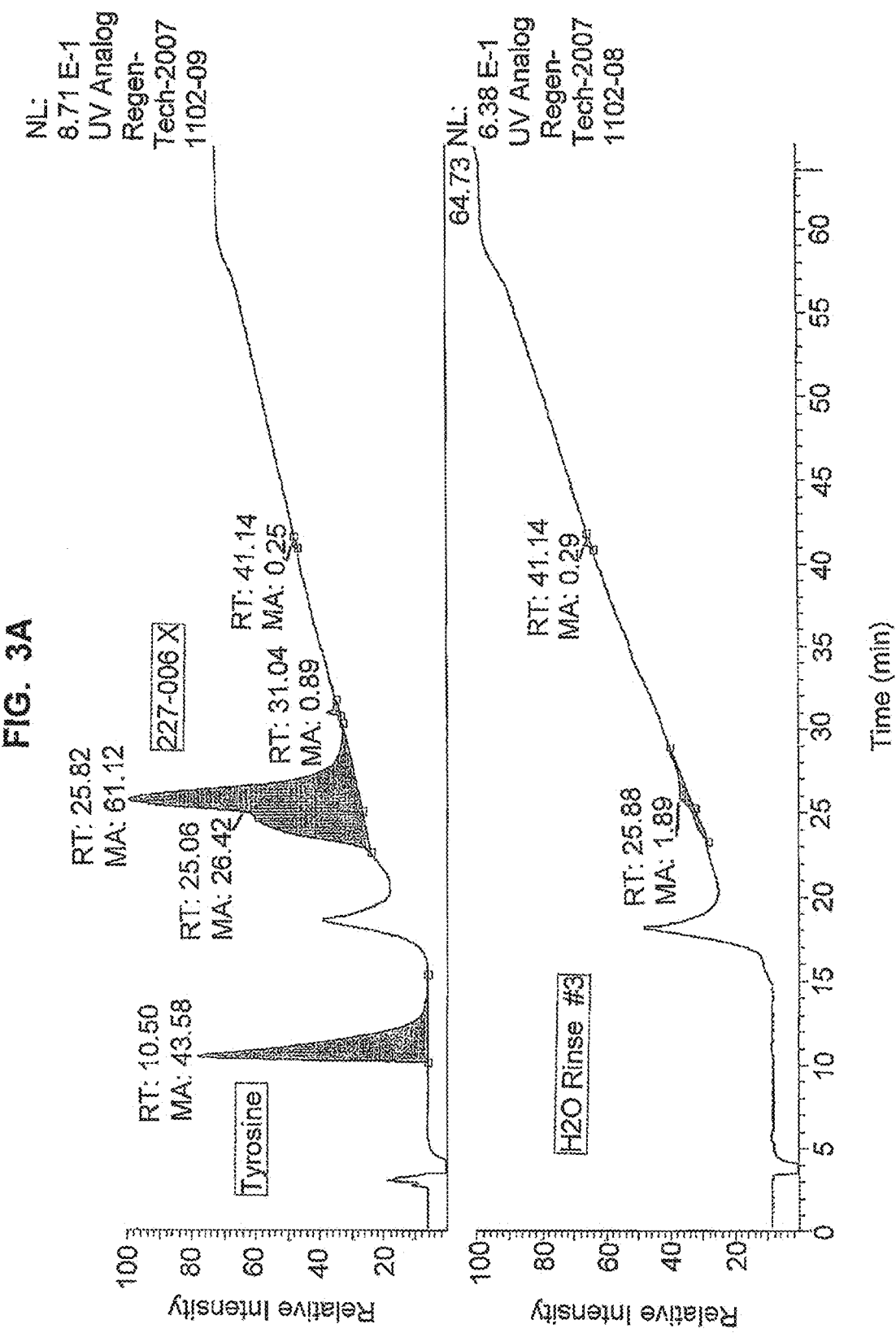
FIGS. 3A through 3F set forth High Performance Liquid Chromatography (HPLC) analyses of several putties and carriers. Some of the carriers were gelatins while other carriers were made from DBM at different temperatures.
Figure 3B:
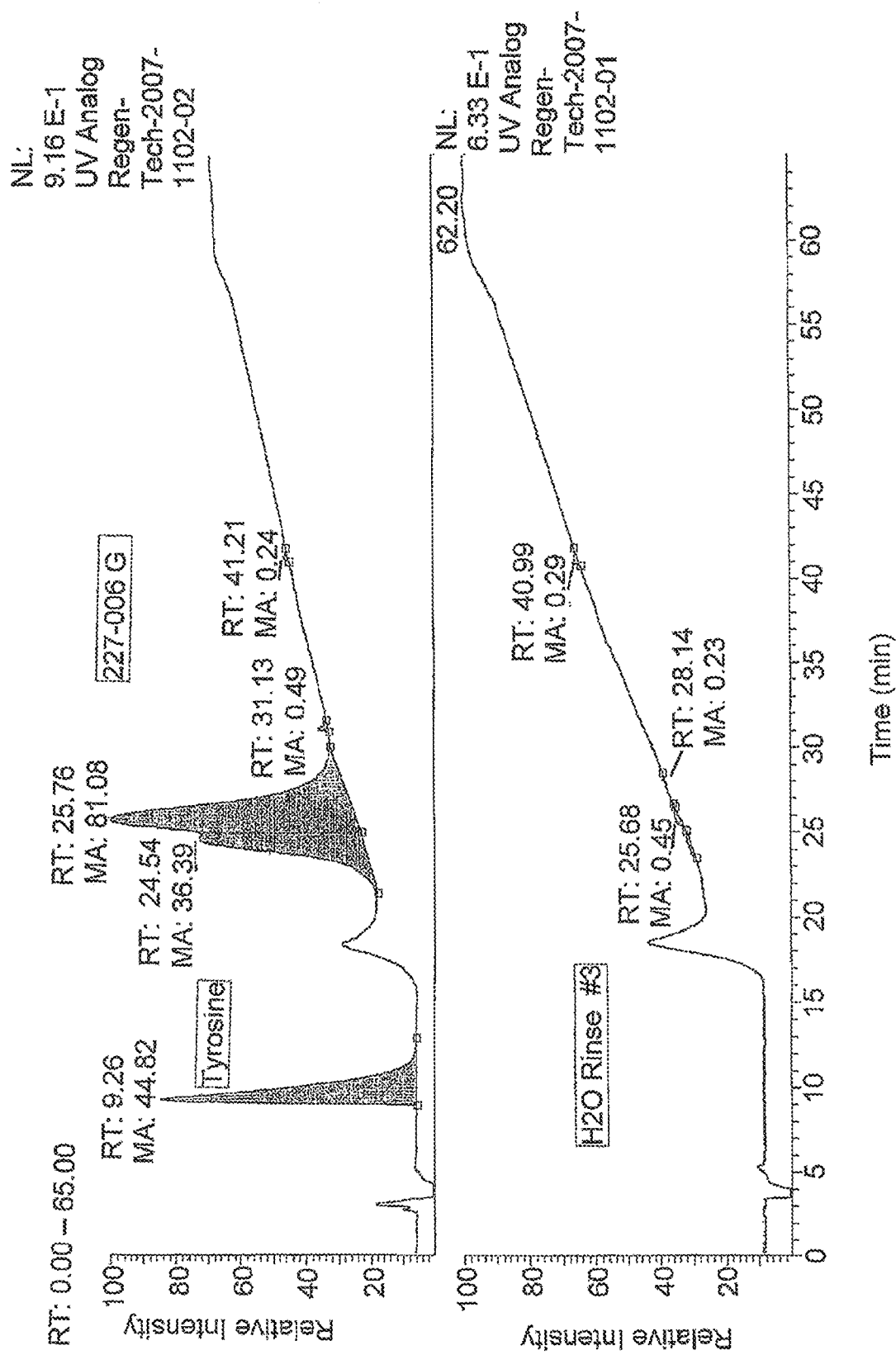
Figure 3C:
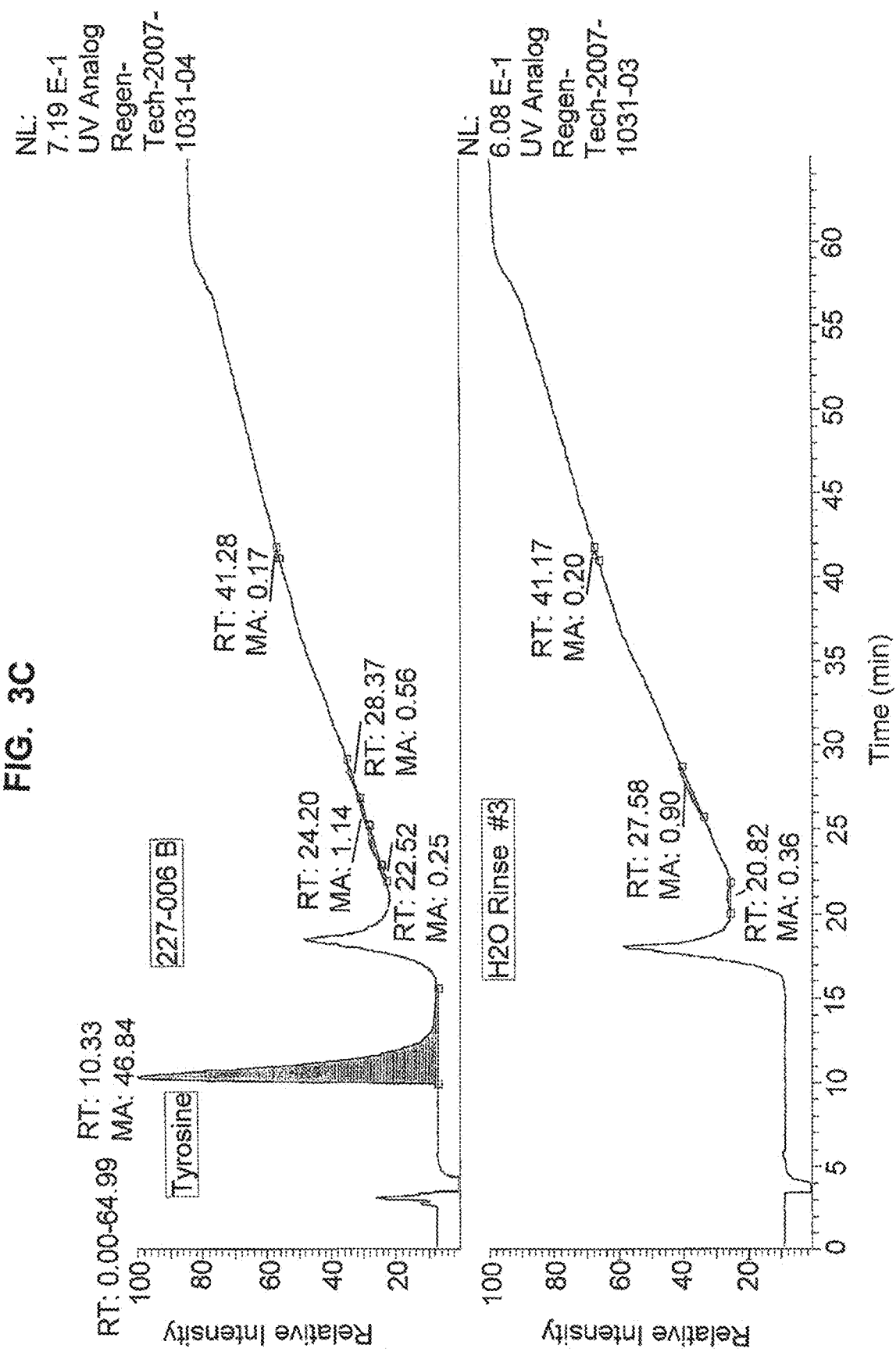
Figure 3D:
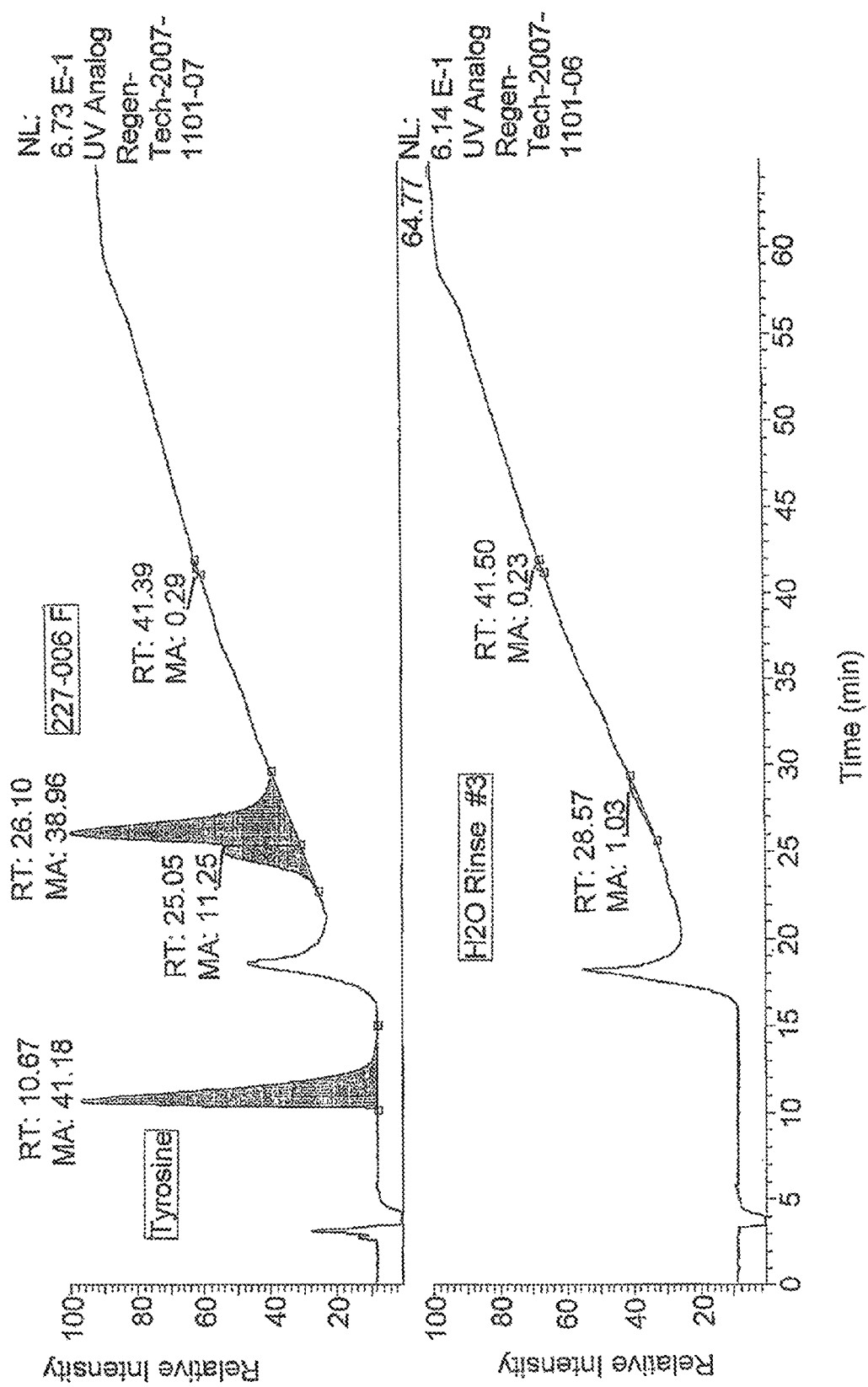
Figure 3E:
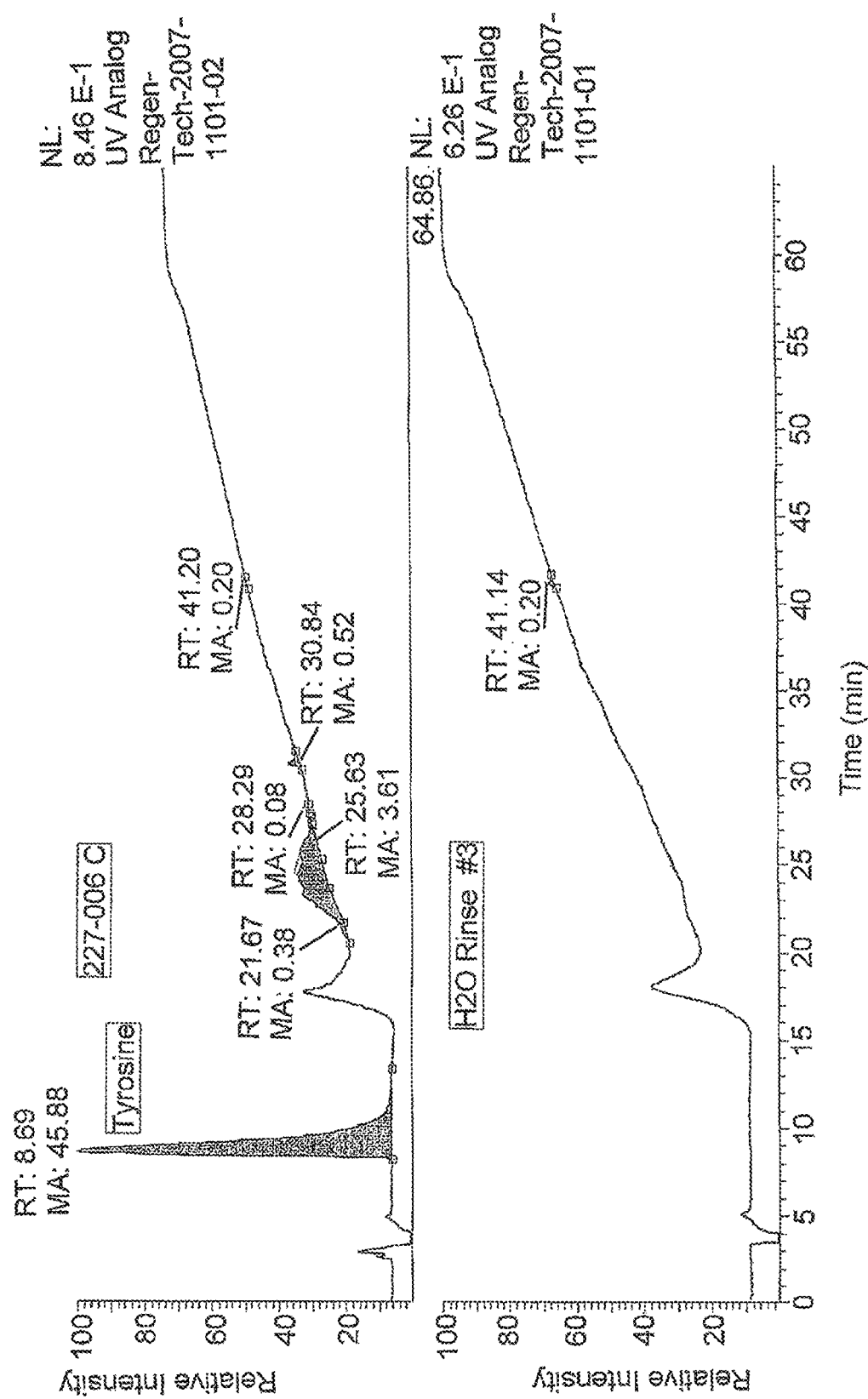
Figure 3F:
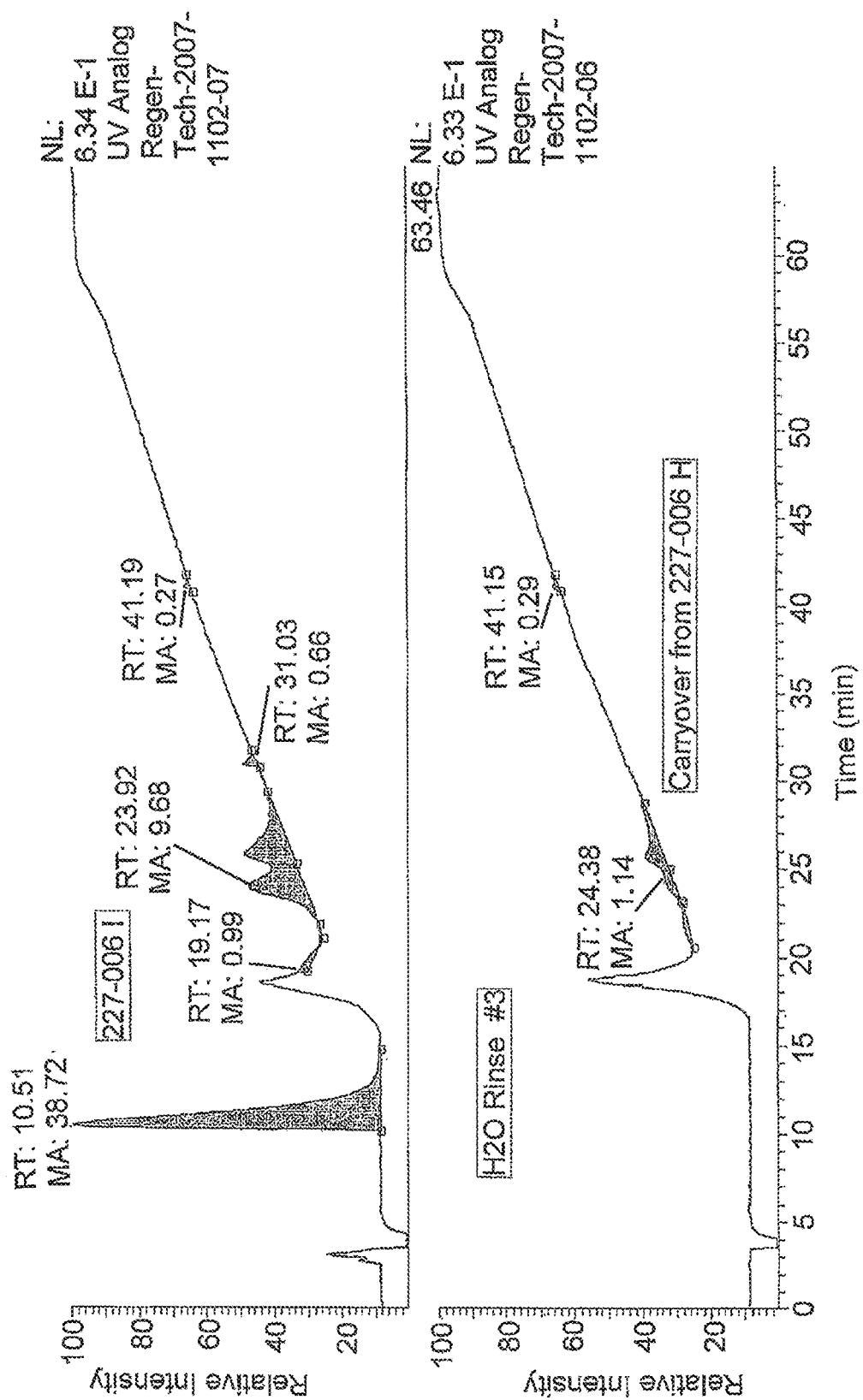

FIG. 3A is the HPLC profile of a commercially available food quality KNOX® gelatin sample. FIG. 3B is the HPLC profile of a fine porcine gelatin sample. FIG. 3C is the HPLC profile of DBM processed at 55° C. and mixed with DBM particles. FIG. 3D is the HPLC profile of a coarse porcine gelatin sample. FIG. 3E is the HPLC profile of DBM processed at 120° C. FIG. 3F is the HPLC profile of DBM processed at 100° C. As can be seen from these results, the gelatin samples had a characteristic double peak which is not present in FIG. 3E. This is consistent with this sample comprising a carrier that is not a gelatin.

EXAMPLE 17

In this example, the extrudability of a variety of carrier and putty samples were analyzed to determine whether there were differences in how the samples performed upon extrusion from a syringe. The test was carried out as follows: A total of 47 samples of carrier, putty, or gelatin were mixed, packed into syringes and sealed in bags for storage. All carrier and active DBM was selected from a store of pooled (multiple donor) DBM.

Samples 17A, 17A2, and 17A3 were putties made from 5.18 g of carrier, 4.0 g of active DBM, and 4.71 mL of water. The carriers were made in batches by mixing 1 part carrier DBM in mg to 10 parts 0.05 N HCl in mL, and heating the mixture at 120° C. in an autoclave for 90 minutes. Sample 17A4 was a putty made from 5.19 g of carrier, 4.0 g of active DBM, and 6.22 mL of water. The carrier was made in batches by mixing 1 part carrier DBM in mg to 10 parts 0.05 N HCl in mL, and heating the mixture at 120° C. in an autoclave for 90 minutes.

Sample 17B was a putty made from 5.18 g of carrier, 4.0 g of active DBM, and 4.71 mL of water. The carrier was made in batches by mixing 1 part carrier DBM in mg to 10 parts 0.05 N HCl in mL, and heating the mixture at 55° C. in an autoclave for 90 minutes. Sample 17BX was a putty made from 5.18 g of carrier, 4.0 g of active DBM, and 8.71 mL of water. The carrier was made in batches by mixing 1 part carrier DBM in mg to 10 parts 0.05 N HCl in mL, and heating the mixture at 55° C. in an autoclave for 90 minutes.

Samples 17C and 17C2 were wet carriers made from 9.18 g of carrier and 4.71 mL of water. The carriers were made in batches by mixing 1 part carrier DBM in mg to 10 parts 0.05 N HCl in mL, and heating the mixture at 120° C. in an autoclave for 90 minutes.

Sample 17D was a wet carrier made from 9.18 g of carrier and 4.71 mL of water. The carrier was made in batches by mixing 1 part carrier DBM in mg to 10 parts 0.05 N HCl in mL, and heating the mixture at 55° C. in an autoclave for 90 minutes. Sample 17DX was a putty made from 5.18 g of carrier, 4.0 g of active DBM, and 5.71 mL of water. The carrier was made in batches by mixing 1 part carrier DBM in mg to 10 parts 0.05 N HCl in mL, and heating the mixture at 55° C. in an autoclave for 90 minutes.

Samples 17E and 17E2 were putties made from 2.67 g of carrier, 4.23 g of active DBM, and 14 mL of water. The carriers were a commercially available fine porcine gelatin carrier. Samples 17F and 17N were putties made from 2.67 g of carrier, 4.23 g of active DBM, and 14 mL of water. The carriers were a commercially available coarse porcine gelatin carrier. Samples 17G and 17G2 were wet carriers made from 6.9 g of carrier and 14 mL of water. The carriers were a commercially available fine porcine gelatin carrier.

Samples 17H and 17H2 were putties made from 5.18 g of carrier, 4.0 g of active DBM, and 4.71 mL of water. The carriers were made in batches by mixing 1 part carrier DBM in mg to 10 parts 0.05 N HCl in mL, and heating the mixture at 100° C. in an autoclave for 90 minutes. Sample 17HX was a putty made from 5.18 g of carrier, 4.0 g of active DBM, and 6.71 mL of water. The carrier was made in batches by mixing 1 part carrier DBM in mg to 10 parts 0.05 N HCl in mL, and heating the mixture at 100° C. in an autoclave for 90 minutes.

Samples 17I and 17IX were wet carriers made from 9.18 g of carrier and 4.71 mL of water. The carriers were made in batches by mixing 1 part carrier DBM in mg to 10 parts 0.05 N HCl in mL, and heating the mixture at 100° C. in an autoclave for 90 minutes. Samples 17I3 and 17I4 were putties made from 5.19 g of carrier, 4.0 g of active DBM, and 6.22 mL of water. The carriers were made in batches by mixing 1 part carrier DBM in mg to 10 parts 0.05 N HCl in mL, and heating the mixture at 100° C. in an autoclave for 90 minutes.

Sample 17J was a wet carrier made from 9.18 g of carrier and 4.71 mL of water. The carrier was made in batches by mixing 1 part carrier DBM in mg to 10 parts 0.05 N HCl in mL, and heating the mixture at 100° C. in an autoclave for 180 minutes.

Samples 17K and 17KX were wet carriers made from 9.18 g of carrier and 4.71 mL of water. The carriers were made in batches by mixing 1 part carrier DBM in mg to 10 parts 0.05 N HCl in mL, and heating the mixture at 120° C. in an autoclave for 60 minutes.

Samples 17L and 17LX were putties made from 5.18 g of carrier, 4.0 g of active DBM, and 4.71 mL of water. The carriers were made in batches by mixing 1 part carrier DBM in mg to 10 parts 0.05 N HCl in mL, and heating the mixture at 100° C. in an autoclave for 180 minutes.

Samples 17M and 17MX1 were putties made from 5.18 g of carrier, 4.0 g of active DBM, and 4.71 mL of water. The carriers were made in batches by mixing 1 part carrier DBM in mg to 10 parts 0.05 N HCl in mL, and heating the mixture at 120° C. in an autoclave for 60 minutes. Sample 17MX2 was a putty made from 5.18 g of carrier, 4.0 g of active DBM, and greater than 4.71 mL of water. The carrier was made in batches by mixing 1 part carrier DBM in mg to 10 parts 0.05 N HCl in mL, and heating the mixture at 120° C. in an autoclave for 60 minutes.

Samples 17O and 17O2 were putties made from 5.18 g of carrier, 4.0 g of active DBM, and 20.71 mL of water. The carriers were made in batches by mixing 1 part carrier DBM in mg to 10 parts 0.05 N HCl in mL, and heating the mixture at 100° C. in an autoclave for 90 minutes.

Sample 17P was a putty made from 5.18 g of carrier, 4.0 g of active DBM, and 20.71 mL of water. The carrier was made in batches by mixing 1 part carrier DBM in mg to 10 parts 0.05 N HCl in mL, and heating the mixture at 120° C. in an autoclave for 60 minutes.

Sample 17C2X was a wet carrier made from 9.18 g of carrier and 5.71 mL of water. The carrier was made in batches by mixing 1 part carrier DBM in mg to 10 parts 0.05 N HCl in mL, and heating the mixture at 120° C. in an autoclave for 90 minutes.

Sample 17Q2 and 17R2 were putties made from 5.18 g of carrier, 4.0 g of active DBM, and 20.71 mL of water. The carriers were made in batches by mixing 1 part carrier DBM in mg to 10 parts 0.05 N HCl in mL, and heating the mixture at 120° C. in an autoclave for 75 minutes.

Sample 17S3 was a putty made from 5.18 g of carrier, 4.0 g of active DBM, and 4.71 mL of water. The carrier was made in batches by mixing 1 part carrier DBM in mg to 10 parts 0.05 N HCl in mL, and heating the mixture at 135° C. in an autoclave for 90 minutes. Sample 17S4 was a putty made from 5.19 g of carrier, 4.0 g of active DBM, and 6.22 mL of water. The carrier was made in batches by mixing 1 part carrier DBM in mg to 10 parts 0.05 N HCl in mL, and heating the mixture at 135° C. in an autoclave for 90 minutes.

Sample 17T3 was a putty made from 5.18 g of carrier, 4.0 g of active DBM, and 4.71 mL of water. The carrier was made in batches by mixing 1 part carrier DBM in mg to 10 parts 0.05 N HCl in mL, and heating the mixture at 135° C. in an autoclave for 75 minutes.

Sample 17U3 was a putty made from 5.18 g of carrier, 4.0 g of active DBM, and 4.71 mL of water. The carrier was made in batches by mixing 1 part carrier DBM in mg to 10 parts 0.05 N HCl in mL, and heating the mixture at 120° C. in an autoclave for 180 minutes.

Sample 17V3 was a putty made from 5.18 g of carrier, 4.0 g of active DBM, and 4.71 mL of water. The carrier was made in batches by mixing 1 part carrier DBM in mg to 10 parts 0.05 N HCl in mL, and heating the mixture at 115° C. in an autoclave for 90 minutes. Sample 17V3X was a putty made from 5.18 g of carrier, 4.0 g of active DBM, and 7.07 mL of water. The carrier was made in batches by mixing 1 part carrier DBM in mg to 10 parts 0.05 N HCl in mL, and heating the mixture at 115° C. in an autoclave for 90 minutes.

Sample 17W3 was a putty made from 5.18 g of carrier, 4.0 g of active DBM, and 4.71 mL of water. The carrier was made in batches by mixing 1 part carrier DBM in mg to 10 parts 0.05 N HCl in mL, and heating the mixture at 118° C. in an autoclave for 90 minutes. Sample 17W3X was a putty made from 5.18 g of carrier, 4.0 g of active DBM, and 7.07 mL of water. The carrier was made in batches by mixing 1 part carrier DBM in mg to 10 parts 0.05 N HCl in mL, and heating the mixture at 118° C. in an autoclave for 90 minutes.

Sample 17X4 was a putty made from 5.19 g of carrier, 4.0 g of active DBM, and 6.22 mL of water. The carrier was made in batches by mixing 1 part carrier DBM in mg to 10 parts 0.05 N HCl in mL, and heating the mixture at 110° C. in an autoclave for 90 minutes.

Where the material in a given sample was noted to be especially stiff or dry, extra samples were mixed with additional water (as indicated in Table 2) and stored either in a Becton Dickinson 5 mL slip tip syringe (reference number 301603), having a nominal 12 millimeter bore inside diameter, nominal 2 millimeter extrusion tip inside diameter and nominal 9 millimeter extrusion tip length plus a nominal 3 millimeter sloped funnel or transition zone between the bore and the extrusion tip, or placed directly in a poly bag, as noted. Samples 17A, 17B, 17BX, 17C, 17D, 17DX, 17E, 17F, 17G, 17H, 17HX, 17I, 17IX, 17J, 17K, 17KX, 17L, 17LX, 17M, 17MX1 17MX2, 17N, 17O, and 17P were then stored for 48-72 hours. After these samples were prepared, it was recognized that the Beckton Dickinson 5 mL slip tip syringes are not as moisture resistant as might be desirable. Accordingly, Samples 17A2, 17C2, 17C2X, 17E2, 17G2, 17H2, 17O2, 17Q2, and 17R2 were prepared and stored for only 1-3 hours in the same Becton Dickinson 5 mL slip tip syringes. Additional putty or carrier material from some samples were prepared for non-extruded handling and moldability testing, this additional material was loaded into a custom Oratech 5 mL storage device, featuring a nominal 10 millimeter bore inside diameter, nominal 10 millimeter extrusion tip inside diameter, with only a minor step or lip between the inside bore diameter and the inside tip diameter (to prevent over travel of the plunger). This storage device features an ejection plunger and an airtight silicone cap covering the free end. This storage time was estimated to be long enough to allow any potential gelatinous setup to occur, but short enough to avoid excessive moisture loss.

After these samples were tested, alternative processing conditions within a defined range of times at various temperatures were tested and the carrier or putty was evaluated. Accordingly, samples 17A3, 17S3, 17T3, 17U3, 17V3, 17V3X, 17W3, and 17W3X and 17I3 were prepared and stored for 1-3 hours, again in the same Beckton Dickinson 5 mL slip tip syringes. After these samples were tested, a spectrum of putty performance was explored across varying processing temperatures for a given processing time (and also across varying processing times for a given temperature). It was also recognized that the Becton Dickinson syringes might be the limiting factor in extrusion force testing, due to their deformation under extrusion loads, their small tip size and large bore size (low extrusion area to bore area ratio). It was further recognized that alternative ratios of dry carrier, DBM, and water might be used to produce a carrier or putty of the present invention. Accordingly, samples 17A4, 17I4, 17S4 and 17X4 were prepared using a higher concentration of water, and then stored for 1-3 hours in Oratech syringes (Oratech/Ultradent; South Jordan, Utah; part number 3310), having a 10 millimeter nominal bore inside diameter and a 2.5 millimeter nominal extrusion tip inside diameter, and nominal 7 millimeter extrusion tip length with a flat barrel end, showing no noticeable funnel or transition region between the bore and the extrusion tip. The Oratech syringes were selected due to their lower deformation under extrusion loads, their larger tip inside diameter, smaller bore inside diameter (higher extrusion area to bore area ratio), more rigid mechanical construction, and their twist-on locking cap feature.

After the storage time, the bags were opened and the syringes containing the samples were retrieved for testing. Each syringe was mounted in a cylindrical collett and supported in a test fixture on an Instron force testing machine (Loadcell model #2525805, Serial #UK1178; Frame 5865 Series; System Serial #001167, System ID #5865P4532). The Instron load cell was centered atop the syringe plunger and brought into contact to an initial load of about 0.01 kN. A test profile was then executed, commanding a downward motion of 10 mm over a period of 10 seconds. At the conclusion of the test profile, the load cell released to an idle load of about 0.01 kN, before repeating the profile for a second time, releasing the load cell again, then repeating the profile for a third time. For each syringe, three motions of 10 mm each were attempted unless syringe failure occurred prior to the third motion. Such syringe failure is referred to as No Extrusion, and is indicated as "NE" in Table 2. Maximum reaction force was observed from the computer control screen for each 10 mm motion, and force-deflection data was logged to an output file at each motion. The presence or absence of any putty behind the plunger tip was noted as "blow-by" on the data sheet. Color and physical condition of the syringe and extrudate was also recorded for each syringe tested. Where there was no extrusion after all three motions, this was also noted as "No Extrusion" (NE).

Results are shown in Table 2 below. As can be seen from these results, the putties made by heating DBM at a temperature of 120° C. for 90 minutes had better extrudability, as indicated by consistent and reliable extrusion of a smooth continuous or semi-continuous bead of putty, with a reasonable extrusion force, even following overnight storage in an uncapped syringe. Further testing of samples 17A4, 17I4, 17S4, and 17X4 with the Oratech syringes demonstrated a clear decreasing trend in extrusion force with increasing processing temperature for a given processing time and putty composition. Extrusion force data is not available for samples 17A3, 17S3, 17T3, 17U3, 17V3, 17V3X, 17W3, and 17W3X and 17I3 because the data did not appear to be reliable.

EXAMPLE 18

In this example, the cohesion in solution ("dissolution time") of a variety of carrier and putty samples were analyzed to determine whether there were differences in cohesiveness. The test was carried out as follows: The samples from Example 17 were formed into a bead of approximately 1 millimeter in diameter and approximately 10 to 20 millimeters in length. Where the material in a given sample was noted to be especially stiff or dry, extra samples were mixed with the same or more water and stored either in a syringe or directly in a poly bag, as noted. After the storage time, the bags were opened and syringes retrieved for testing. The extrudate from Example 17, above, was used when available. For those samples where the syringe failed prior to producing any extrudate, material was taken from the extra, bagged material or other storage device produced at syringe filling. The sample (approximately 10 to 20 millimeter length of extrudate, or roughly equivalent amount of bagged/non-extruded material) was placed into a beaker of water at 37° C. with visual observation of cohesion/dissolution over time as recorded with a manual stopwatch. Dissolution was considered to have occurred when the sample visibly lost shape and fell apart, either spontaneously, or with occasionally mild agitation after 1 minute in the water. Results are shown in Table 2 below. As can be seen from these results, the putties made by heating DBM at a temperature of 120° C. for 90 minutes had higher cohesiveness, as indicated by higher dissolution times of 3:00 minutes (sample A) and 6:00 minutes (sample C). Samples 17KX and 17IX also exhibited good dissolution times of 5:00 minutes each. For samples 17A3, 17S3, 17T3, 17U3, 17V3, 17V3X, 17W3, and 17W3X, extrudate or excess material was rolled by hand into a ball prior to testing, and dissolution times above 2 minutes were not recorded, as indicated by a "+" sign in the table. For samples 17A4, 17I4, 17S4 and 17X4, dissolution times were not tested.

EXAMPLE 19

In this example, the "irrigation resistance time" of a variety of carrier and putty samples were analyzed to determine whether there were differences in resistance to irrigation. The test was carried out as follows: The samples from Example 17 were formed into a bead of approximately 1 millimeter in diameter and approximately 10 to 20 millimeters in length. Where the material in a given sample was noted to be especially stiff or dry, extra samples were mixed with the same or more water and stored either in a syringe or directly in a poly bag, as noted. After the storage time, the bags were opened and syringes retrieved for testing. The extrudate from Example 17, above, was used when available. For those samples where the syringe failed prior to producing any extrudate, material was taken from the extra, bagged material produced at syringe filling. The sample (approximately 10 to 20 millimeters length of extrudate, or roughly equivalent amount of bagged/non-extruded material) was placed on a glass microscope slide, applying light to moderate finger pressure to promote adherence of the sample to the slide while maintaining the basic shape of the sample where possible. Results are shown in Table 2 below. Where the sample did not stick to the microscope slide it was noted as "did not stick" (DNS). As can be seen from these results, the putties made by heating DBM at a temperature of 120° C. for 90 minutes had better irrigation resistance, as indicated by higher irrigation resistance times of 4 minutes and 55 seconds (sample A) and more than 10 minutes (sample C). For samples 17A3, 17S3, 17T3, 17U3, 17V3, 17V3X, 17W3, and 17W3X, irrigation times above 5 minutes were not recorded, as indicated by a "+" sign in the table. For samples 17A4, 17I4, 17S4 and 17X4, irrigation times were not tested.

TABLE 2

| # | Sample Description | DBM | Observations | Syringe Blow By | Moldable | Extrusion Load (N) | Dissolution Time (m · ss) | Irr. Time (m · ss) |
|---|---|---|---|---|---|---|---|---|
| 17A | DBM, water and carrier made at 120° C. for 90 minutes | x | golden brown/honey color paste in syringe; light tan, smooth strong-semi-continuous bead; 2nd syringe ears yielded | y | | 400 | 3.00 | 4.55 |
| 17B | DBM, water and carrier made at 55° C. for 90 minutes | x | v. light tan dense paste in syringe; no extrusion (NE); extra sample bag tested for diss/irr | n | | NE | 0.00 | 0.00 |
| 17BX | DBM, water and carrier made at 55° C. for 90 minutes with additional 4 mL water | | off-white-tan spongy paste in syr; fluffy white broken beads extr | n | | N/A | 0.00 | 0.04 |
| 17C | Carrier made at 120° C. at 90 minutes | | dark brown/honey color paste in syringe; med tan, smooth strong-fully-continuous bead; IRR test stopped at 10 minutes, still holding strong | y | | 480 | 6.00 | 10+ |
| 17D | Carrier made at 55° C. at 90 minutes | | v. light tan dense paste in syringe; no extr.; | n | | 550 NE | n/a | n/a |
| 17DX | DBM, water and carrier made at 55° C. for 90 minutes with additional 1 mL water | x | v. light tan dense paste in syringe; no extr.; extra sample bag w/dense spongy crumbs tested for diss/irr | n | | 500 NE | 0.10 | 0.05 |
| 17E | DBM, water and fine porcine gelatin carrier | x | blotch/mottled off-whie & yellow stiff spongy paste in syr; rough, open-cell, highly broken tubes extr. | n | | 160 | 0.01 | 0.05 |
| 17F | Water and coarse porcine gelatin carrier | | translucent white w/yellow cast lumpy looking paste in syr; clear/white granules/beads extruded | y | | 380 | 0.03 | 0.01 |
| 17G | Water and fine porcine gelatin carrier | | translucent off-white-yellow slightly-lumpy looking paste in syr; fluffy-white granules extruded | y | | 410 | 0.08 | DNS |
| 17H | DBM, water and carrier made at 100° C. for 90 minutes | x | mottled light/med tan paste in syr; no extr | n | | 270; 590 | n/a | n/a |
| 17HX | DBM, water and carrier made at 100° C. for 90 minutes with additional 2 mL water and extrabag | x | extra bag w/mottled light/med tan clumpy granules; no extr | n/a | | n/a | 1.00 | 0.00 |
| 17I | Water and carrier made at 100° C. for 90 minutes | | golden brown/honey color paste in syringe; no extr. | n | | 500 NE | n/a | n/a |
| 17IX | water and carrier made at 100° C. for 90 minutes, and extrabag | | extra bag w/mottled golden brown/honey colored rubbery spongy clumps; no extr; large clump used for irr test, still together at 5 min but starting to flake apart | n/a | | n/a | 5.00 | DNS |
| 17J | water and carrier made at 100° C. for 180 minutes | | golden brown/honey color paste in syringe; light tan, rough strong-semi-continuous bead | y | | 520 | 0.30 | DNS |
| 17K | water and carrier made at 120° C. for 60 minutes | | golden brown/honey color paste in syringe; no extr. | n | | 550 NE | n/a | n/a |

TABLE 2-continued

| # | Sample Description | DBM | Observations | Syringe Blow By | Moldable | Extrusion Load (N) | Dissolution Time (m · ss) | Irr. Time (m · ss) |
|---|---|---|---|---|---|---|---|---|
| 17KX | water and carrier made at 120° C. for 60 minutes-extrabag | | extra bag w/mottled golden brown/honey colored rubbery spongy clumps; no extr; large clump used for irr test, still together at 5 min but starting to flake apart | n/a | | n/a | 5.00 | DNS |
| 17L | DBM, water and carrier made at 100° C. for 180 minutes | x | golden brown/honey color paste in syringe; no extr. | n | | 550 NE | n/a | n/a |
| 17LX | DBM, water and carrier made at 100° C. for 180 minutes-extrabag | x | extra bag w/mottled light/med tan spongy granules; no extr | n/a | | n/a | 0.45 | DNS |
| 17M | DBM, water and carrier made at 120° C. for 60 minutes | x | slightly mottled golden brown/honey color paste in syringe; no extr. | n | | 550 NE | n/a | n/a |
| 17MX1 | DBM, water and carrier made at 120° C. for 60 minutes-extrabag | x | extra bag w/mottled light/med tan spongy granules; no extr | n/a | | n/a | 0.30 | DNS |
| 17MX2 | DBM, water and carrier made at 120° C. for 60 minutes, with unknown volume of additional water | x | v. light tan dense paste in syringe; off-white-tan-yellow discontinuous bead extr.; | y | | 420 | 0.08 | 0.00 |
| 17N | DBM, water and coarse porcine gelatin carrier | x | off-white-yellow mottled paste in syr; fluffy white small spongy granules extr; IRR sample left some sticky residual on glass | n | | 190 | 0.00 | 0.00 |
| 17O | DBM, water and carrier made at 100° C. for 90 minutes with additional 16 mL water | x | off-white-tan dense paste in syringe; off-white-tan-yellow semi-smooth highly discontinuous bead extr.; | n | | 60 | 0.05 | 0.01 |
| 17P | DBM, water and carrier made at 120° C. for 60 minutes with additional 16 mL water | x | med tan dense paste in syringe; v. light tan smooth discontinuous bead extr.; | n | | 310 | 0.06 | 0.00 |
| 17A2 | DBM, water and carrier made at 120° C. for 90 minutes | x | med/light tan paste in syringe; smooth solid continuous extruded bead. mixed 13:30, tested 16:00 = 2:30 setup time | y | excellent | 293 | 2.30 | 12:00+ |
| 17C2 | Carrier made at 120° C. for 90 minutes | | dark tan/honey color with lumpy bead | y | yes, but sticky | 470 | 2.30 | 0.30 |
| 17C2X | Carrier made at 120° C. for 90 minutes with additional 1 mL water | | dark tan/honey color with rough lumpy bead | y | too sticky to mold well | 226 | 3.00 | 0.30 |
| 17Q2 | DBM, water and carrier made at 120° C. for 75 minutes with additional 16 mL water | x | light tan color with smooth solid continuous bead | n | yes | 339 | 3.00 | 0.05 |
| 17R2 | DBM, water and carrier made at 120° C. for 75 minutes with additional 16 mL water | x | light/med tan with lumpy irregular continuous bead | n | yes, clumpy, sticky | 278 | 3.00 | 0.03 |
| 17H2 | DBM, water and carrier made at 100° C. for 90 minutes | x | blotchy/mottled off-white & yellow stiff spongy paste in syr; rough, open-cell, highly broken tubes extr. | n | yes, spongy, crumbly | 371 | 0.08 | 0.02 |
| 17O2 | DBM, water and carrier made at 100° C. for 90 minutes with additional 16 mL water | x | smooth yellow paste makes puffy semi-continuous bead | n | yes, spongy | 55 | 0.06 | 0.02 |
| 17E2 | DBM, water and fine porcine gelatin carrier | x | off-white paste makes puffy semi-continuous bead | n | yes, but crumbly | 164 | 0.08 | 0.00 |
| 17G2 | Fine porcine gelatin carrier | | light-off-white paste makes very puffy, very irregular continuous bead mixed 15:30, tested 16:50 = ~1:20 setup time | y | no, too crumbly | 370 | 0.10 | 0.00 |
| 17A3 | DBM, water, and carrier made at 12°0C. for 90 minutes | x | | y | good | data not available | 2.00+ | 5.00+ |
| 17S3 | DBM, water, and carrier made at 135° C. for 90 minutes | x | Didn't extrude. | y | good | data not available | 0.30 | 5.00+ |
| 17T3 | DBM, water, and carrier made at 135° C. for 75 minutes | x | | n | Good, but tacky | data not available | 2.00+ | 5.00+ |
| 17U3 | DBM, water, and carrier made at 120° C. for 180 minutes | x | syringe failed during 3$^{rd}$ etxr. | y | good | .data not available | 2.00+ | 5.00+ |
| 17V3 | DBM, water, and carrier made at 115° C. for minutes | x | syringe failure. | n | hard to mold, not tacky | data not available | 2.00+ | DNS |

TABLE 2-continued

| # | Sample Description | DBM | Observations | Syringe Blow By | Moldable | Extrusion Load (N) | Dissolution Time (m · ss) | Irr. Time (m · ss) |
|---|---|---|---|---|---|---|---|---|
| 17V3X | DBM, water, and carrier made at 115° C. for 90 minutes @ 150% H2O | x | | | n | Fluffy, crumbly, hard to mold, not tacky | .data not available | 1.00 | 0.05 |
| 17W3 | DBM, water, and carrier made at 118° C. for 90 minutes | x | Didn't extrude. | n | yes | data not available | 2.00 | DNS |
| 17W3X | DBM, water, and carrier made at 118° C. for 90 minutes @ 150% H20 | x | | n | Fluffy but moldable with effort | data not available | 1.00 | 0.10 |
| 17I3 | DBM, water, and carrier made at 100° C. for 90 minutes (NEG CONTROL) | x | No extrusion. | n | no, like gel | data not available | 2.00+ | DNS |
| 17A4 | DBM, water, and carrier made at 120° C. for 90 minutes + NEW H2O CONC. | x | | n | yes | 119 | not tested | not tested |
| 17I4 | DBM, water, and carrier made at 100° C. for 90 minutes + NEW H2O CONC. | x | lighter in color than 17A4 | n | No, crumbly and fluffy | 593 | not tested | not tested |
| 17S4 | DBM, water, and carrier made at 135° C. for 90 minutes + NEW H2O CONC. | x | darker shade than17A4 | n | Very well | 25 | not tested | not tested |
| 17X4 | DBM, water, and carrier made at 110° C. for 90 minutes + NEW H2O CONC. | x | lighter in color than 17A4 | n | Somewhat, with a lot of effort, although fluffy and crumbles | 368 | not tested | not tested |

EXAMPLE 20

In this example, the Bloom strength of a variety of carrier and putty samples were analyzed to determine whether there were differences in Bloom strength. The test was carried out as follows: Sample 20A was a putty made from 5.18 g of carrier, 4.0 g of active DBM, and 4.71 mL of water. The carrier was made in batches by mixing 1 part carrier DBM in mg to 10 parts 0.05 N HCl in mL, and heating the mixture at 120° C. in an autoclave for 90 minutes. Sample 20B was a putty made from 5.18 g of carrier, 4.0 g of active DBM, and 4.71 mL of water. The carrier was made in batches by mixing 1 part carrier DBM in mg to 10 parts 0.05 N HCl in mL, and heating the mixture at 55° C. in an autoclave for 90 minutes. Sample 20C was a wet carrier made from 9.18 g of carrier and 4.71 mL of water. The carrier was made in batches by mixing 1 part carrier DBM in mg to 10 parts 0.05 N HCl in mL, and heating the mixture at 120° C. in an autoclave for 90 minutes. Sample 20D was a wet carrier made from 9.18 g of carrier and 4.71 mL of water. The carrier was made in batches by mixing 1 part carrier DBM in mg to 10 parts 0.05 N HCl in mL, and heating the mixture at 55° C. in an autoclave for 90 minutes. Sample 20E was a putty made from 2.67 g of carrier, 4.23 g of active DBM, and 14 mL of water. The carrier was a commercially available fine porcine gelatin carrier. Sample 20F was a putty made from 2.67 g of carrier, 4.23 g of active DBM, and 14 mL of water. The carrier was a commercially available coarse porcine gelatin carrier. Sample 20G was a wet carrier made from 6.9 g of carrier and 14 mL of water. The carrier was a commercially available fine porcine gelatin carrier. Sample 20H was a putty made from 5.18 g of carrier, 4.0 g of active DBM, and 4.71 mL of water. The carrier was made in batches by mixing 1 part carrier DBM in mg to 10 parts 0.05 N HCl in mL, and heating the mixture at 100° C. in an autoclave for 90 minutes. Sample 20I was a wet carrier made from 9.18 g of carrier and 4.71 mL of water. The carrier was made in batches by mixing 1 part carrier DBM in mg to 10 parts 0.05 N HCl in mL, and heating the mixture at 100° C. in an autoclave for 90 minutes.

Dry material was weighed into water to create a 6.67% solution in standard Bloom bottles with stoppers. The mix was then stirred and left to hydrate for approximately 3 hours at room temperature. Once soaked, bottles were placed in a 65° C. bath for 20 minutes, stirring occasionally to assure that the composition was completely dissolved. After allowing the Bloom jars to cool for 15 minutes at room temperature, they were then conditioned for 16 hours in a 10° C. water bath. The Bloom jar was centered with the probe just above the sample surface. The probe is a 12.7 mm diameter flat face, cylindrical probe with a sharp edge. The test begins when the designated 4 g trigger force is reached.

The probe then penetrates the gelatin to a target depth of 4 mm at a speed of 0.5 mm/s, and then retracts. The peak force is accepted as the gel strength in grams Bloom, uncorrected for moisture.

Results are shown in Table 3 below. As can be seen from these results, the putty and carrier made by heating DBM at a temperature of 120° C. for 90 minutes (samples 20A and 20C) did not have a measurable Bloom strength, since they failed to trigger the initial 4 g force required for the Bloom measurement. The Bloom strength of samples 20B and 20D also could not be measured. These samples were a clear liquid with considerable solids settled at the bottom after stirring. In samples 20A and 20C, only a small amount of solids settled after stirring.

TABLE 3

| Sample No. | Bloom Strength |
|---|---|
| 20A | Not measurable |
| 20B | Not measurable |
| 20C | Not measurable |
| 20D | Not measurable |
| 20E | 65 g Bloom |
| 20F | 276 g Bloom |
| 20G | 144 g Bloom |

Samples 20A, 20B, 20C and 20 D did not form a gel. Samples 20E formed a soft gel and Samples 20 F and 20 G formed clear gels.

EXAMPLE 21

In this example, the dynamic viscosities of a variety of carrier and putty samples were analyzed to determine whether there were differences in dynamic viscosity. In this example, Sample 21A was a putty made from 5.18 g of carrier, 4.0 g of active DBM, and 4.71 mL of water. The carrier was made by mixing a 1:10 (g:mL) ratio of DBM and 0.05 N HCl, and heating the mixture at 120° C. in an autoclave for 90 minutes. Sample 21B was a putty made from 5.18 g of carrier, 4.0 g of active DBM, and 4.71 mL of water. The carrier was made by mixing a 1:10 ratio of DBM and 0.05 N HCl, and heating the mixture at 55° C. in an autoclave for 90 minutes. Sample 21C was a wet carrier made from 9.18 g of carrier and 4.71 mL of water. The carrier was made by mixing a 1:10 ratio of DBM and 0.05 N HCl, and heating the mixture at 120° C. in an autoclave for 90 minutes. Sample 21D was a wet carrier made from 9.18 g of carrier and 4.71 mL of water. The carrier was made by mixing a 1:10 ratio of DBM and 0.05 N HCl, and heating the mixture at 55° C. in an autoclave for 90 minutes. Sample 21E was a putty made from 2.67 g of carrier, 4.23 g of active DBM, and 14 mL of water. The carrier was a commercially available fine porcine gelatin carrier. Sample 21F was a putty made from 2.67 g of carrier, 4.23 g of active DBM, and 14 mL of water. The carrier was a commercially available coarse porcine gelatin carrier. Sample 21G was a wet carrier made from 6.9 g of carrier and 14 mL of water. The carrier was a commercially available fine porcine gelatin carrier. Sample 21H was a putty made from 5.18 g of carrier, 4.0 g of active DBM, and 4.71 mL of water. The carrier was made by mixing a 1:10 ratio of DBM and 0.05 N HCl, and heating the mixture at 100° C. in an autoclave for 90 minutes. Sample 21I was a wet carrier made from 9.18 g of carrier and 4.71 mL of water. The carrier was made by mixing a 1:10 ratio of DBM and 0.05 N HCl, and heating the mixture at 100° C. in an autoclave for 90 minutes.

The test was carried out as using a Brookfield SST 2000 Soft Solids Tester ("SST 2000"). Samples 21A-21I were placed in the SST 2000. The SST 2000 applied a constant, low stress to the samples. The SST 2000 maintained that stress for a period of 60 seconds and then released the stress. The samples' response to stress (how far and how fast it moves) was plotted as a function of time. Another plot was created by extrapolating the straight-line steady-shear portion down to the strain axis. This gave a certain strain value that describes the eventual equilibrium extension of the elastic elements present. The equilibrium strain was then compared to the total strain to obtain an elastic/viscous ratio or elasticity index for the samples.

Figure 4A:
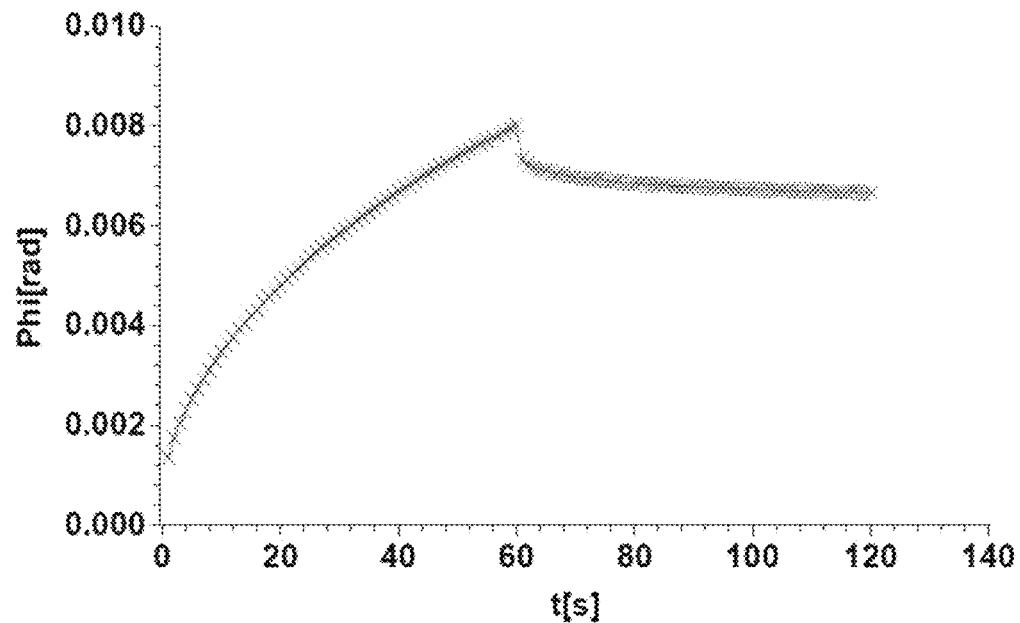
FIGS. 4A and 4D set forth dynamic viscosity analyses of putties and carriers prepared from demineralized bone matrix at different temperatures.
Figure 4B:
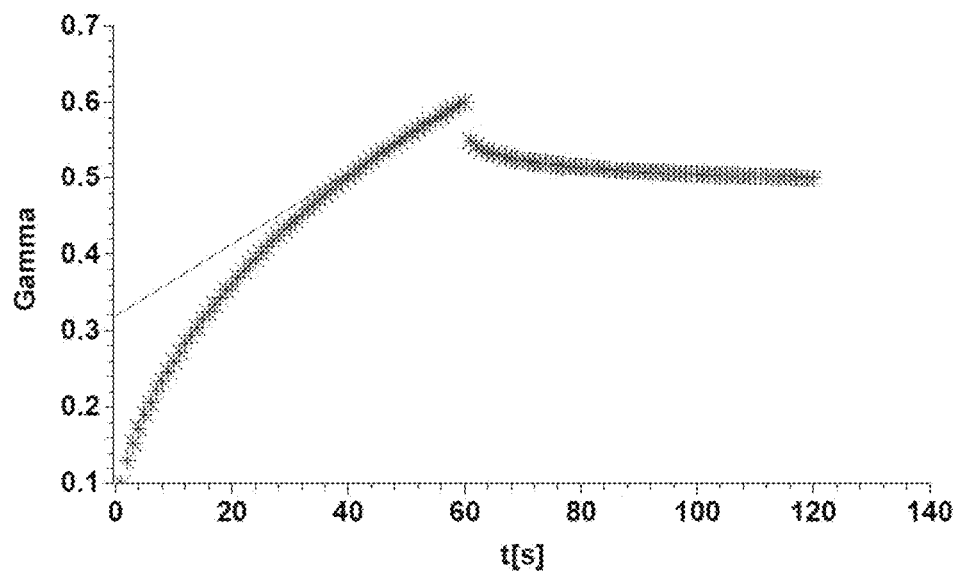
Figure 4C:
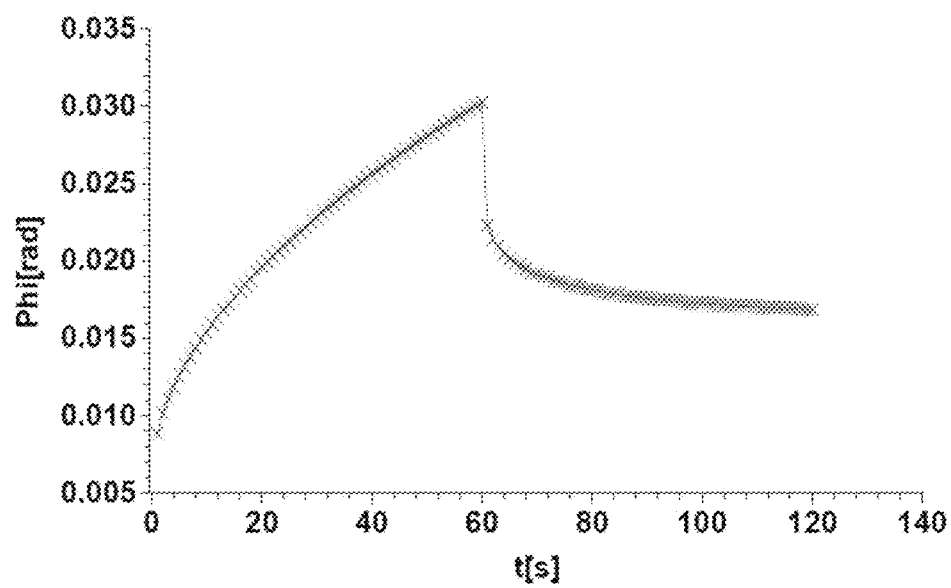
Figure 4D:
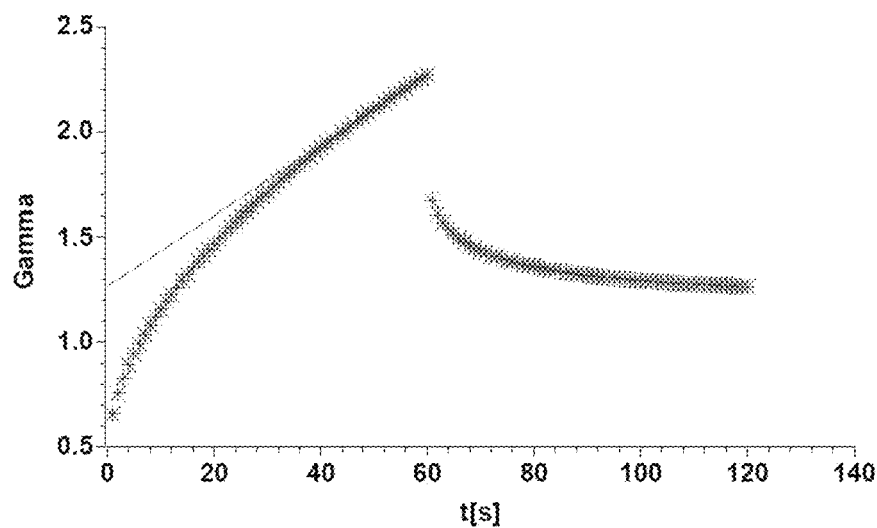

FIGS. 4A through 4D set forth dynamic viscosity analyses of Samples 21A and 21C prepared as described above. FIGS. 4A and 4B relate to Sample 21A. FIGS. 4C and 4D relate to Sample 21C. Results of dynamic viscosity testing are also shown in Table 4 below. As can be seen from these results, only the putty and carrier made by heating DBM at a temperature of 120° C. for 90 minutes (Samples 21A and 21C) resulted in a measurable dynamic viscosity. The dynamic viscosity of Samples 21B and 21D through 21I could not be measured using this test procedure because they formed gelatins and gelatins do not have a measurable dynamic viscosity.

TABLE 4

| Results of Dynamic Viscosity Testing | | | | |
|---|---|---|---|---|
| Sample | Creep Viscosity (Pas) | Shear Rate (1/s) | Creep Rate (rad/s) | Elastic Index |
| 21A | 38428.102 | 0.0047 | 0.00006 | 0.531 |
| 21B | No Result | No Result | No Result | No Result |
| 21C | 10826.62 | 0.0167 | 0.00022 | 0.5586 |
| 21D | No Result | No Result | No Result | No Result |
| 21E | No Result | No Result | No Result | No Result |
| 21F | No Result | No Result | No Result | No Result |
| 21G | No Result | No Result | No Result | No Result |
| 21H | No Result | No Result | No Result | No Result |
| 21I | No Result | No Result | No Result | No Result |

EXAMPLE 22

In this example, a kit comprising an osteoinductive putty was made. DBM was separated into two portions: "Carrier DBM" and "Active DBM". The "Carrier DBM" was used to make carrier according to Example 1 and is then lyophilized and stored.

Lyophilized carrier made according to Example 1 was removed from the container in which it was lyophilized. The carrier was placed in a blender pitcher being sure not to fill past the top of the black blade device. A lid was placed on the pitcher and tightly sealed all the way around. The blender was pulsed for 10 seconds at a speed of 7500 rpm. After pausing for 10 seconds, the blender was pulsed again for 10 seconds, followed by an additional 10 second pause and 10 second pulse.

The carrier from the pitcher was placed into a 850 μm sieve. Carrier passing through the sieve was collected. 10.4 g carrier was transferred from the collecting pan into a mixing bowl. 8.0 g of 'active DBM' was combined with the carrier in a mixing bowl and mixed with a spoonula until evenly mixed.

The syringes for the putty and the equipment for loading the putty into the syringes were prepared before combining the mixture with water. The plunger of the loading dispenser was removed, and the final product syringes were prepared for loading. This reduced the exposure of the putty to open air so as to avoid moisture loss.

14.31 ml sterile water was placed in a bowl, and the combination of DBM and carrier was poured into the bowl containing water. The water, DBM and carrier were mixed immediately using a spoonula. A firm steady kneading motion was used in order to fully press the water into the mixture. The water was spread evenly throughout the putty, with no dry pockets remaining in the putty. Once all powder was evenly wet (powder tends to darken visibly with wetting), the putty was gathered together into one large piece.

The spoonula was used to collect the putty and to place it into the loading dispenser barrel. The loading dispenser plunger was inserted back into the barrel of the loading dispenser. The loading dispenser bore tip was placed into the barrel of a syringe, and an amount of putty (0.5 cc, 1 cc, 2 cc, or 5 cc) was extruded into syringes of appropriate sizes (1 cc, 3 cc, and 5 cc), just above the 0.5 cc, 1 cc, 2 cc, or 5 cc volume indicator on the appropriate syringes. The product volume was assessed using the increments marked on the syringe. The loading dispenser was removed, and the syringe plunger was placed back into the syringe barrel. The syringe was checked to ensure that under the plunger there was still 0.5 cc, 1 cc, 2 cc, or 5 cc of putty. The 1 cc syringe was capped with a screw-on cap, and the 3 cc and 5 cc syringes were capped by pressing the silicone cap firmly on the syringe barrel until secure. The caps were firmly secured onto the syringe. The putties are sealed in the capped syringes.

The filled syringe was inserted into a clearfoil (inner) pouch. The clearfoil pouch was placed in an Accu-Seal Model 730 Medical Sealer. Once the sealing cycle was complete, the pouch was removed from the sealer, and a barcode was added for product tracking. The clearfoil pouch was placed in a tyvek (outer) pouch with chevron seals on the same side.

EXAMPLE 23

In this example, the osteoinductive potential of several embodiments of the present osteoinductive putty was evaluated in a Urist (rat ectopic pouch) model, as well as the inflammatory response of the rats to these putties. The osteoinductivity and inflammation scores of the putties were compared to scores from implanting DBM alone.

As a starting material, four DBM samples were provided which had been obtained from four different donors. These DBM samples had been previously scored for osteoinductivity and inflammation by an athymic nude rat assay. Previous scoring was completed on these samples of DBM plus porcine gelatin. These previous scores were used to select the treatment groups for this example. For example, one treatment group was to be implanted with DBM sample that scored a 2 for osteoinductivity and a 1 for inflammation when tested with a porcine gelatin. DBM sample from one donor that previously scored 2.1, and three donors that previously scored 3.1 were selected for use in this example. Samples that had previously scored 0.1 and 4.1 were also used in this example as controls.

Carrier was prepared from the starting DBM as described in Example 1. The final formulations of the putties were prepared as described in Example 8. All donor material was processed in a controlled production environment by bone paste processors using conventional methods of DBM preparation. Samples were prepared in accordance with Table 5. Putty samples were packed into 1 cc sterile syringes. The DBM controls were packed in sterile vials. All samples were packaged in foil-foil pouches and were sent for irradiation at a dosage of 25-31 kGy.

After irradiation, the samples were implanted in athymic nude rats in accordance with the following procedures. Each rat was implanted with a different sample at six different sites in the ventral abdominal muscle (sites A through F on each rat). The rat subjects were anesthetized with ketamine/xylazine. A mid-ventral incision (1 inch) was made from below the sternum to just above the groin area. The skin was lifted and bluntly dissected from the fascia. Any remaining fascia was snipped away. The skin was clamped on one side, exposing the muscle. The abdominal muscle was picked up 1-1.5 cm to the side of the midline (in the recti abdomini). A 1-2 mm incision was made in the muscle pinched by a forceps. The tip of scissors was inserted laterally into the incision in the muscle, and gently opened and closed to make a small pocket for the sample. The peritoneal cavity was not penentrated.

The putty or DBM was dispensed directly into the appropriate muscle pocket site. The muscle incision was sutured, and the procedure was repeated to implant putty or DBM in the other five sites in the ventral admonimal muscle of the rat. All six implant sites were visually checked to see that the implant was still in place, the stitch was secure, and there were no visible problems relating to the surgery. The incision in the rat's abdomen was then closed.

Each treatment was implanted in triplicate in three separate rats. Six samples were implanted per rat. The rats were sacrificed and the implants were extracted after 28 days and the samples were prepared for histological evaluation. All implanted material was carefully retrieved, and if no implant was visible, the muscle portion was removed where suture indicated implant was placed. The histological slides were scored for osteoinductivity and inflammatory responses as follows.

Each slide was examined under the microscope and rated for osteoinductivity. There were five slices per explant, and each slice was individually scored as follows: It was scored "0" if there was no sign of new bone formation in any of the five slices of the explant. It was scored "1" if up to 25% of the area of the explant slice was involved in bone formation. It was scored "2" if between 25 and 50% of the area of the explant slice is involved in bone formation. It was scored "3" if between 50 and 75% of the area of the explant slice is involved in bone formation. It was scored "4" if between 75 and 100% of the area of the explant slice is involved in bone formation. Areas were considered to be involved in bone formation where they demonstrated evidence of new bone formation including chondrocytes, cartilage, marrow, and new bone.

Each slide to be rated for inflammation was examined under the microscope. There were five slices per explant. Each slice was individually scored as follows. It was scored "1" if no multi-nucleated giant cell (MNGCs) were present, minimal fibrous connective tissue was largely in the periphery of explant, and residual allograft (un-remodeled implant material) appeared intact or involved in remodeling. It was scored "2" if occasional MNGCs were observed, moderate fibrous connective tissue was present in the periphery and interstitially, and residual allograft appeared intact or involved in remodeling. It was scored "3" if 50% or more of explant area demonstrated cellular infiltration largely characterized by MNGCs, dense fibrous connective tissue filled the majority of the explant area, and residual allograft was being resorbed and/or absent.

TABLE 5

Sample Categories and Treatments

| Sample | Starting DBM | Implanted Material | Rat-Implant Location | | |
|---|---|---|---|---|---|
| 23A | Donor 1 | Carrier & Active DBM | 1-A | 4-B | 3-C |
| 23B | Donor 1 | Active DBM Only | 2-F | 1-D | 5-A |
| 23C | Donor 2 | Carrier & Active DBM | 3-E | 2-C | 1-C |
| 23D | Donor 2 | Active DBM Only | 4-A | 5-F | 5-B |
| 23E | Donor 3 | Carrier & Active DBM | 4-C | 2-B | 3-A |
| 23F | Donor 3 | Active DBM Only | 2-D | 1-E | 5-E |
| 23G | Donor 4 | Carrier & Active DBM | 5-C | 1-B | 2-E |
| 23H | Donor 4 | Active DBM Only | 3-B | 3-D | 4-D |
| 23I | Donor 5 | DBM Only | 4-F | 2-A | 3-F |
| 23J | Donor 6 | DBM Only | 1-F | 5-D | 4-E |

Table 6 sets forth the raw histology scores from each implant sample.

TABLE 6

| | | Rat 1 | | | Rat 2 | | | Rat 3 | | |
|---|---|---|---|---|---|---|---|---|---|---|
| Sample | Treatment | OI (% bone) | Maturity | Inf | OI (% bone) | Maturity | Inf | OI (% bone) | Maturity | Inf |
| 23A | D1 Putty | 2 (38) | 7 | 1 | 2 (40) | 8 | 1 | 3 (51) | 8 | 1 |
| 23B | D1 DBM alone | 2 (45) | 8 | 1 | 2 (42) | 7 | 1 | 2 (43) | 8 | 2 |
| 23C | D2 Putty | 3 (52) | 8 | 1 | 2 (49) | 8 | 1 | 2 (37) | 7 | 1 |
| 23D | D2 DBM alone | 2 (43) | 8 | 2 | 3 (57) | 9 | 1 | 2 (38) | 8 | 1 |
| 23E | D3 Putty | 2 (32) | 8 | 2 | 3 (61) | 9 | 2 | 3 (60) | 9 | 2 |
| 23F | D3 DBM alone | 4 (76) | 9 | 1 | 3 (59) | 9 | 1 | 3 (68) | 9 | 2 |
| 23G | D4 Putty | 1 (15) | 7 | 1 | 1 (22) | 5 | 1 | 1 (20) | 7 | 1 |
| 23H | D4 DBM alone | 1 (22) | 7 | 1 | 2 (47) | 8 | 1 | 2 (29) | 8 | 1 |
| 23I | D5 control | 0 (0) | 0 | 2 | 0 (0) | 0 | 2 | 0 (0) | 0 | 3 |
| 23J | D6 DBM control | 4 (76) | 9 | 1 | 3 (58) | 9 | 1 | 3 (60) | 9 | 1 |

Table 7 sets forth the mean and the standard deviation of the histology scores:

TABLE 7

| Sample | Treatment | OI ± SD | % Bone ± SD | Maturity ± SD | Inflammation ± SD |
|---|---|---|---|---|---|
| 23A | D1 Putty | 2.3 ± 0.58 | 43 ± 7 | 7.7 ± 0.58 | 1 ± 0 |
| 23B | D1 DBM alone | 2 ± 0 | 43.3 ± 1.5 | 7.7 ± 0.58 | 1.3 ± 0.58 |
| 23C | D2 Putty | 2.3 ± 0.58 | 46 ± 7.9 | 7.7 ± 0.58 | 1 ± 0 |
| 23D | D2 DBM alone | 2.3 ± 0.58 | 46 ± 10 | 8.3 ± 0.58 | 1.3 ± 0.58 |
| 23E | D3 Putty | 2.7 ± 0.58 | 51 ± 16 | 8.7 ± 0.58 | 2 ± 0 |
| 23F | D3 DBM alone | 3.3 ± 0.58 | 67.7 ± 8.5 | 9 ± 0 | 1.3 ± 0.58 |
| 23G | D4 Putty | 1 ± 0 | 19 ± 3.6 | 6.3 ± 1.2 | 1 ± 0 |
| 23H | D4 DBM alone | 1.7 ± 0.58 | 32.7 ± 12.9 | 7.7 ± 0.58 | 1 ± 0 |
| 23I | D5 control | 0 ± 0 | 0 ± 0 | 0 ± 0 | 2.3 ± 0.58 |
| 23J | D6 control | 3.3 ± 0.58 | 64.7 ± 9.9 | 9 ± 0 | 1 ± 0 |

The addition of the carrier to the active DBM did not unduly affect the OI results of the putties compared to the DBM alone. In addition, there was no significant affect in the bone maturity scores of the putties relative to the DBM alone. Although the sample size was small (n=4 donors), this data suggests that there is no difference between individual donors in the fact that the addition of the carrier to the active DBM did not unduly affect the results. As expected, the OI score for the negative control (0.1 DBM) samples was zero as was the bone maturity score. The OI score for the positive control was in the 3-4 range with a bone maturity score of 9.

As shown in Tables 6 and 7, the putty samples (Samples 23A, 23C, 23E and 23G) compared favorably to the DBM alone samples (Samples 23B, 23D, 23F and 23H) with respect to inflammation scores. The addition of the carrier to the DBM did not result in inflammation scores that would be rejected (to avoid rejection, at least 2 of 3 samples from each donor must receive an inflammatory score equal to or less than 2).

Only one sample (Donor 3, Samples 23E and 23F) generated an inflammatory score of 2 in all three rats. One sample from Donor 1, Donor 2, and Donor 3 had an inflammatory score of 2. As noted above, all the samples tested would be passed by the relevant inflammatory scoring protocol. The other test samples within each of these treatment groups demonstrated inflammatory scores of 1. The deactivated DBM control (Donor 5, sample 23I) generated an inflammatory that would be rejected by the current RTI inflammatory scoring protocol and this has been observed in the past.

This example demonstrates that the present osteoinductive putty is effective at inducing new both growth in the subjects in which it was implanted. It also demonstrates that the present osteoinductive putties generally did not generate an excessive inflammatory response in the subjects.

In the present specification, use of the singular includes the plural except where specifically indicated. The use of the terms "a" and "an" and "the" and similar referents in the context of describing the invention (especially in the context of the following claims) are to be construed to cover both the singular and the plural, unless otherwise indicated herein or clearly contradicted by context. The terms "comprising," "having," "including," and "containing" are to be construed as open-ended terms (i.e., meaning "including, but not limited to,") unless otherwise noted. Whenever the term "about" appears before a value, it should be understood that the specification is also providing a description of that value apart from the term "about". Wherever an open-ended term is used to describe a feature or element of the invention, it is specifically contemplated that a closed-ended term can be used in place of the open-ended term without departing from the spirit and scope of the invention. Recitation of ranges of values herein are merely intended to serve as a shorthand method of referring individually to each separate value falling within the range, unless otherwise indicated herein, and each separate value is incorporated into the specification as if it were individually recited herein. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

In the present specification, any of the functions recited herein may be performed by one or more means for performing such functions. With respect to the methods described in the specification, it is intended that the specification also provides a description of the products of those methods. With respect to the compositions and combinations described in the specification, it is intended that the specification also provides a description of the components, parts, portions, of such compositions and combinations.

All of the references cited herein, including patents, patent applications, and publications, are hereby incorporated in their entireties by reference.

While particular elements, embodiments and applications of the present invention have been shown and described, it will be understood, of course, that the invention is not limited thereto since modifications can be made by those skilled in the art without departing from the scope of the present disclosure, particularly in light of the foregoing teachings.

Although the dependent claims have single dependencies in accordance with U.S. patent practice, each of the features in any of the dependent claims can be combined with each of the features of other dependent claims or the main claim.

We claim:

1. A carrier for use in an implantable composition comprising a mixture of thermally denatured collagen fragments,
    wherein said mixture of thermally denatured collagen fragments has a sodium dodecyl sulfate polyacrylamide gel electrophoresis (SDS-PAGE) profile, and said SDS-PAGE profile comprises a region between about 29 kDa and about 97 kDa,
    wherein said region is without prominent, intense, or discernable bands as compared to a Type-I collagen reference material, wherein
    said SDS-PAGE profile was obtained on standard 12 lane 8-16% gradient pre-made gels through analysis at constant voltage of 100 V for 2.5 h, transferred to nitrocellulose filter and stained with 0.1% ponceau red to confirm protein transfer and mark the position of molecular weight markers; and
    wherein said carrier is not a gelatin, does not have a measurable Bloom strength and wherein said SDS-PAGE profile also has a band between about 15 kDa and about 20 kDa; and
    wherein said carrier is made from demineralized bone matrix (DBM).

2. The carrier of claim 1, wherein said SDS-PAGE profile is substantially the same as shown in Lane C of any of FIG. 2A, 2B, 2C, or 2D.

3. An osteoinductive putty comprising an osteoinductive substance, and the carrier of claim 1 in an amount of from about 27 to about 38 percent, wherein the putty is extrudable, moldable, resistant to irrigation, and exhibits cohesiveness in solution at 37° C. for at least about 60 seconds; and wherein said osteoinductive substance is demineralized bone matrix (DBM).

4. The osteoinductive putty of claim 3, wherein the putty is adapted for packing into a bone defect.

5. The osteoinductive putty of claim 3, wherein the putty remains extrudable after extended storage in a sealed package.

6. A method of making the carrier of claim 1 comprising: providing a collagen source comprising demineralized bone matrix (DBM); combining the collagen source with a denaturing solution other than water or saline to create a collagen source mixture; and heating the collagen source mixture to a temperature greater than 100° C.

7. The method of claim 6 wherein the denaturing solution comprises 0.05 N HCl and the temperature is about 120° C., and the collagen source mixture is heated for about 90 minutes.

8. An osteoinductive putty comprising an osteoinductive substance, the carrier of claim 1 in an amount of from about 27 to about 38 percent, and a liquid medium; and a package, wherein the osteoinductive substance and carrier are sealed in the package, and wherein the putty is ready to use (RTU) upon removal from the package; and wherein said osteoinductive substance is demineralized bone matrix (DBM).

9. A method of treating a subject in need of treatment for a bone defect, the method comprising: implanting the osteoinductive putty of claim 8 into a bone defect.

* * * * *